United States Patent [19]

Bühlmayer et al.

[11] Patent Number: 4,914,129
[45] Date of Patent: Apr. 3, 1990

[54] ANTIHYPERTENSIVE 5-AMINO-4-HYDROXYVALERYL DERIVATIVES SUBSTITUTED BY SULPHUR-CONTAINING GROUPS

[75] Inventors: Peter Bühlmayer, Arlesheim, Switzerland; James L. Stanton, Lebanon, N.J.; Walter Fuhrer, Lupsingen, Switzerland; Richard Göschke, Bottmingen, Switzerland; Vittorio Rasetti, Basel, Switzerland; Heinrich Rüeger, Oberwil, Switzerland

[73] Assignee: Ciba-Geigy Corporation, Ardsley, N.Y.

[21] Appl. No.: 405,372

[22] Filed: Sep. 8, 1989

Related U.S. Application Data

[60] Division of Ser. No. 341,239, Apr. 19, 1989, which is a continuation of Ser. No. 187,608, Apr. 28, 1988, abandoned, which is a division of Ser. No. 11,183, Feb. 5, 1987, Pat. No. 4,758,584.

[30] Foreign Application Priority Data

Feb. 7, 1986 [CH] Switzerland ............... 486/86
Aug. 20, 1986 [CH] Switzerland ............... 3347/86

[51] Int. Cl.⁴ .................. A61K 31/165; C07C 147/05
[52] U.S. Cl. ........................ 514/616; 514/18; 530/331; 564/153
[58] Field of Search ............. 514/400, 18, 616; 530/331; 548/344; 564/153

[56] References Cited

U.S. PATENT DOCUMENTS

| | | | |
|---|---|---|---|
| 4,198,398 | 4/1980 | Hudson et al. | 514/16 |
| 4,372,974 | 2/1983 | Fish et al. | 514/557 |
| 4,424,207 | 1/1984 | Szelke et al. | 514/16 |
| 4,470,971 | 9/1984 | Boger et al. | 514/18 |
| 4,478,826 | 10/1984 | Veber et al. | 514/18 |
| 4,479,941 | 10/1984 | Veber et al. | 530/331 |
| 4,609,643 | 9/1986 | Szelke et al. | 514/16 |
| 4,613,676 | 9/1986 | Fuhrer et al. | 560/39 |
| 4,665,193 | 5/1987 | Ryono et al. | 548/344 |

FOREIGN PATENT DOCUMENTS 152255 8/1985 European Pat. Off. .
156322 10/1985 European Pat. Off. .
173481 3/1986 European Pat. Off. .
212903 3/1987 European Pat. Off. .
WO84/03044 8/1984 PCT Int'l Appl. .

OTHER PUBLICATIONS

B. Evans et al., *J. Org. Chem.*, vol. 50, pp. 4615–4625 (1985).
D. Rich et al., Peptides: "Structure and Function", 8th American Peptide Sympsium, pp. 511–520 (1983).
M. Szelke et al., "Peptides: Structure and Function", Proceedings of the 8th American Peptide Symposium, pp. 579–582 (1983).
M. Holladay et al., *Tetrahedron Letters*, vol. 24, p. 4401 (1983).
D. Rich, *J. Med. Chem.*, vol. 28, p. 263 (1985).

Primary Examiner—Richard A. Schwartz
Attorney, Agent, or Firm—JoAnn Villamizar

[57] ABSTRACT

Compounds of the formula

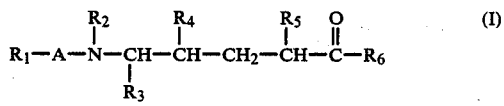

in which $R_1$ represents acyl substituted by a thio, sulphinyl or sulphonyl group, A represents an optionally N-alkylated α-amino acid residue that is bonded N-terminally to $R_1$ and C-terminally to the group $-NR_2-$, $R_2$ represents hydrogen or lower alkyl, $R_3$ represents hydrogen, lower alkyl, optionally etherified or esterified hydroxy-lower alkyl, cycloalkyl, cycloalkyl-lower alkyl, bicycloalkyl-lower alkyl, tricycloalkyl-lower alkyl, aryl or aryl-lower alkyl, $R_4$ represents hydroxy or etherified or esterified hydroxy, $R_5$ represents lower alkyl, optionally etherified or esterified hydroxy-lower alkyl, cycloalkyl, cycloalkyl-lower alkyl, bicycloalkyl, bicycloalkyl-lower alkyl, tricycloalkyl, tricycloalkyl-lower alkyl, aryl, aryl-lower alkyl, optionally substituted carbamoyl, optionally substituted amino, optionally substituted hydroxy, optionally substituted mercapto, sulphinyl or sulphonyl, and $R_6$ represents substituted amino, and salts of such compounds having salt-forming groups, inhibit the blood pressure-increasing action of the enzyme renin and can be used as antihypertensives.

10 Claims, No Drawings

ANTIHYPERTENSIVE 5-AMINO-4-HYDROXYVALERYL DERIVATIVES SUBSTITUTED BY SULPHUR-CONTAINING GROUPS

This is a divisional of application Ser. No. 341,239 filed on Apr. 19, 1989 which is a continuation of Ser. No. 187,608 filed on 4/28/88 abandoned, which is a divisional of Ser. No. 011,183 filed on 02/05/87 now U.S. Pat. No. 4,758,584.

The invention relates to compounds of the formula

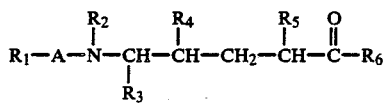

in which $R_1$ represents acyl substituted by a thio, sulphinyl or sulphonyl group, with the exception of an optionally N-substituted acyl radical of a natural amino acid, A represents an optionally N-alkylated α-amino acid residue that is bonded N-terminally to $R_1$ and C-terminally to the group $-NR_2-$, $R_2$ represents hydrogen or lower alkyl, $R_3$ represents hydrogen, lower alkyl, optionally etherified or esterified hydroxy-lower alkyl, cycloalkyl, cycloalkyl-lower alkyl, bicycloalkyl-lower alkyl, tricycloalkyl-lower alkyl, aryl or aryl-lower alkyl, $R_4$ represents hydroxy or etherified or esterified hydroxy, $R_5$ represents lower alkyl, optionally etherified or esterified hydroxy-lower alkyl, cycloalkyl, cycloalkyl-lower alkyl, bicycloalkyl, bicycloalkyl-lower alkyl, tricycloalkyl, tricycloalkyl-lower alkyl, aryl, aryl-lower alkyl, optionally substituted carbamoyl, optionally substituted amino, optionally substituted hydroxy, optionally substituted mercapto, sulphinyl or sulphonyl, and $R_6$ represents substituted amino with the exception of an amino radical derived from an α-amino acid, and to salts of such compounds having salt-forming groups, processes for their manufacture, pharmaceutical preparations containing these compounds and the use of these compounds as medicaments or for the manufacture of pharmaceutical preparations, and intermediates for the manufacture of compounds of the formula I.

In the description of the present invention the term "lower" used in the definition of groups or radicals, for example lower alkyl, lower alkoxy, lower alkanoyl, etc., denotes that those groups or radicals, unless expressly defined otherwise, contain up to and including 7, and preferably up to and including 4, carbon atoms.

The carbon atoms substituted by $R_3$, $R_4$ and $R_5$ may have the R-, S- or R,S-configuration. Compounds of the formula I in which the carbon atoms substituted by $R_3$ and $R_4$ have the S-configuration are preferred.

The general terms and expressions used in the description of the present invention preferably have the following meanings:

Acyl $R_1$ has, for example, up to 25 carbon atoms and is especially an acyl group of a saturated or unsaturated, aliphatic, cycloaliphatic, cycloaliphatic-aliphatic, aromatic, aromatic-aliphatic, heteroaromatic or heteroaromatic-aliphatic carboxylic acid, with the exception of the optionally N-substituted natural amino acid methionine, which acyl group is substituted by a thio, sulphinyl or sulphonyl group and optionally by other groups containing hetero atoms.

Preferred substituents $R_1$ are acyl groups of the formula

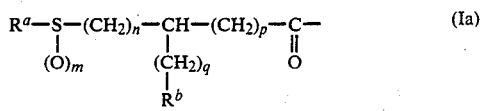

in which $R^a$ represents unsubstituted or substituted lower alkyl, lower alkenyl, lower alkynyl, mono-, bi- or tri-cycloalkyl, cycloalkyl-lower alkyl, unsubstituted or substituted aryl, aryl-lower alkyl, aryl-lower alkenyl, unsubstituted or substituted heteroaryl, heteroaryl-lower alkyl, unsubstituted or substituted hydroxy or unsubstituted or substituted amino, $R^b$ represents hydrogen, mono-, bi- or tri-cycloalkyl, unsubstituted or substituted aryl or unsubstituted or substituted heteroaryl, m represents 0, 1 or 2, n represents 0, 1 or 2, p represents 0, 1 or 2 and q represents 0, 1, 2, 3 or 4.

The methine carbon atom in the partial formula Ia and, if m is 1, also the sulphur atom, may be in the R-, S- or R,S-configuration.

Lower alkyl $R^a$ preferably has from 1 to 7 carbon atoms and is, for example, methyl, ethyl, n-propyl, iso-propyl, n-butyl or tert.-butyl, each of which may be substituted by one or more functional groups, for example hydroxy, etherified hydroxy, for example lower alkoxy, such as methoxy or ethoxy, or phenoxy, esterified hydroxy, for example lower alkanoyloxy, such as acetoxy, halogen, for example chlorine or bromine, hydroxysulphonyloxy, carboxy, esterified carboxy, for example lower alkoxycarbonyl, such as methoxy- or ethoxy-carbonyl, amidated carboxy, for example carbamoyl or mono- or di-lower alkylcarbamoyl, such as methyl- or dimethyl-carbamoyl, cyano, amino, substituted amino, for example mono-lower alkylamino, di-lower alkylamino, acylamino, or substituted amino in which the amino group is part of a five- or six-membered heterocycle containing one or two nitrogen atoms and, if desired, an oxygen or sulphur atom, or by oxo.

Substituted lower alkyl $R^a$ is, for example, hydroxy-lower alkyl, for example 2-hydroxyethyl, lower alkoxy-lower alkyl, for example lower alkoxyethyl, such as 2-methoxyethyl, phenoxy-lower alkyl, for example 2-phenoxyethyl, lower alkanoyloxy-lower alkyl, for example lower alkanoyloxyethyl, such as 2-acetoxyethyl, halo-lower alkyl, for example haloethyl, such as 2-chloro- or 2-bromo-ethyl, hydroxysulphonyloxy-lower alkyl, for example 2-hydroxysulphonyloxyethyl, carboxy-lower alkyl, for example carboxymethyl or 2-carboxyethyl, lower alkoxycarbonyl-lower alkyl, for example lower alkoxycarbonylmethyl or lower alkoxycarbonylethyl, such as methoxycarbonylmethyl, 2-methoxycarbonylethyl, ethoxycarbonylmethyl or 2-ethoxycarbonylethyl, carbamoyl-lower alkyl, for example carbamoylmethyl or 2-carbamoylethyl, lower alkylcarbamoyl-lower alkyl, for example methylcarbamoylmethyl, di-lower alkylcarbamoyllower alkyl, for example dimethylcarbamoylmethyl, cyanolower alkyl, for example 2-cyanoethyl, amino-lower alkyl, for example 2-aminoethyl, lower alkylamino-lower alkyl, for example 2-methylaminoethyl, di-lower alkylamino-lower alkyl, for example 2-dimethylaminoethyl, morpholino-lower alkyl, for example 2-morpholinoethyl, piperidino-lower alkyl, for example 2-piperidinoethyl, acylamino-lower alkyl, for example lower alkanoylamino-lower alkyl, such as 2-acetylaminoethyl, benzyloxycarbonylamino-lower alkyl, such as 2-benzyloxycarbonylaminoethyl, lower alkoxycarbonylamino-lower alkyl, such as 2-tert.-butoxycarbonylaminoethyl, or oxolower alkyl, for example 2-oxopropyl or 2-oxobutyl.

Lower alkenyl $R^a$ contains, for example, from 2 to 7, especially from 2 to 4, carbon atoms and is, for example, vinyl, allyl or 2- or 3-butenyl. Lower alkenyl $R^a$ may be substituted by the same substituents as may lower alkyl, for example by hydroxy, etherified hydroxy, for example methoxy, esterified hydroxy, for example acetoxy, halogen, for example chlorine or bromine, carboxy, esterified carboxy, for example methoxycarbonyl or ethoxycarbonyl, or by amidated carboxy, for example carbamoyl.

Lower alkynyl $R^a$ contains, for example, from 2 to 7, especially from 2 to 4, carbon atoms and is, for example, ethynyl, 1-propynyl or 2-propynyl.

Cycloalkyl $R^a$ or $R^b$ contains, for example, from 3 to 8, especially from 3 to 6, carbon atoms and is, for example, cyclopropyl, cyclobutyl, cyclopentyl or cyclohexyl.

Bicycloalkyl $R^a$ or $R^b$ contains, for example, from 5 to 10, especially from 6 to 9, carbon atoms and is, for example, bicyclo-hexyl, -heptyl, -octyl, -nonyl or -decyl, for example bicyclo[3.1.0]hex-1-, -2- or -3-yl, bicyclo[4.1.0]hept-1- or -7-yl, bicyclo[2.2.1]hept-2-yl, for example endo- or exo-norbornyl, bicyclo[3.2.1]oct-2-yl, bicyclo[3.3.0]oct-3-yl or bicyclo[3.3.1]non-9-yl, also α- or β-decahydronaphthyl.

Tricycloalkyl $R^a$ or $R^b$ contains, for example, from 8 to 10 carbon atoms and is, for example, tricyclo[5.2.1.0$^{2,6}$]dec-8-yl or adamantyl, such as 1-adamantyl.

Cycloalkyl-lower alkyl $R^a$ contains, for example, from 4 to 10, especially from 4 to 7, carbon atoms and is, for example, cyclopropylmethyl, cyclobutylmethyl, cyclopentylmethyl or cyclohexylmethyl.

The cycloaliphatic or cycloaliphatic-aliphatic radicals mentioned may be substituted by the same substituents as may lower alkyl $R^a$.

Aryl $R^a$ or $R^b$ contains, for example, from 6 to 14 carbon atoms and is, for example, phenyl, indenyl, for example 2- or 4-indenyl, 1- or 2-naphthyl, anthryl, for example 1- or 2-anthryl, phenanthryl, for example 9-phenanthryl, or acenaphthenyl, for example 1-acenaphthenyl. Aryl $R^a$ or $R^b$ is substituted, for example, by lower alkyl, for example methyl, hydroxy, lower alkoxy, for example methoxy, acyloxy, for example lower alkanoyloxy, such as acetoxy, amino, lower alkylamino, for example methylamino, di-lower alkylamino, for example dimethylamino, acylamino, for example tert.-butoxycarbonylamino, or halogen, for example chlorine, bromine or iodine, it being possible for the substituent to be in any position in the aryl radical, for example in the o-, m- or p-position of the phenyl radical, and it also being possible for the aryl radical to be polysubstituted by the same or different substituents.

Aryl-lower alkyl $R^a$ has, for example, from 7 to 15 carbon atoms and contains, for example, an unsubstituted or substituted, optionally branched radical mentioned under lower alkyl $R^a$ and an unsubstituted or substituted radical mentioned under aryl $R^a$ or $R^b$. Such an aryl-lower alkyl radical is, for example, benzyl, lower alkylbenzyl, such as 4-methylbenzyl, lower alkoxybenzyl, such as 4-methoxybenzyl, 2-phenylethyl, 2-(p-hydroxyphenyl)-ethyl, diphenylmethyl, di-(4-methoxyphenyl)-methyl, trityl or α- or β-nphthylmethyl.

Aryl-lower alkenyl $R^a$ has, for example, from 8 to 16 carbon atoms and contains, for example, an unsubstituted or substituted radical mentioned under lower alkenyl $R^a$ and an unsubstituted or substituted radical mentioned under aryl $R^a$ or $R^b$. Such an aryl-lower alkenyl radical is, for example, styryl, 3-phenylallyl, 2-(α-naphthyl)-vinyl or 2-(β-naphthyl)vinyl.

Unsubstituted qr substituted heteroaryl $R^a$ or $R^b$ is mono-, bi- or tri-cyclic and contains one or two nitrogen atoms and/or an oxygen or sulphur atom. $R^a$ or $R^b$ is, for example, pyrrolyl, furyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl or a benzo-fused or cyclopenta-, cyclohexa- or cyclohepta-fused derivative of those radicals. This hetero-cycle may be partially saturated and, at a nitrogen atom, it may be substituted by oxido, lower alkyl, for example methyl or ethyl, phenyl, or phenyl-lower alkyl, for example benzyl, and/or, at one or more carbon atoms, it may be substituted by lower alkyl, for example methyl, phenyl, phenyl-lower alkyl, for example benzyl, halogen, for example chlorine, hydroxy, lower alkoxy, for example methoxy, phenyl-lower alkoxy, for example benzyloxy, or by oxo, and is, for example, 2- or 3-pyrrolyl, phenylpyrrolyl, for example 4- or 5-phenyl-2-pyrrolyl, 2-furyl, 2-thienyl, 4-imidazolyl, methyl-imidazolyl, for example 1-methyl-2-, -4- or -5-imidazolyl, 1,3-thiazol-2-yl, 2-, 3- or 4-pyridyl, 1-oxido-2-, -3- or -4-pyridinio, 2-pyrazinyl, 2-, 4- or 5-pyrimidinyl, 2-, 3- or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or -3-indolyl, 4,5,6,7-tetrahydro-2-indolyl, cyclohepta-[b]-5-pyrrolyl, 2-, 3- or 4-quinolyl, 4-hydroxy-2-quinolyl, 10, 3- or 4-isoquinolyl, 1-oxo-1,2-dihydro-3-isoquinolyl, 2-quinoxalinyl, 2-benzofuranyl, 2-benzoxazolyl, 2-benzothiazolyl, benz[e]indol-2-yl or β-carbolin-3-yl.

Heteroaryl-lower alkyl $R^1$ contains, for example, an unsubstituted or substituted radical mentioned under lower alkyl $R^a$ and an unsubstituted or substituted radical mentioned under heteroaryl $R^a$ or $R^b$ and is, for example, 2- or 3-pyrrolylmethyl, 2-, 3- or 4-pyridylmethyl, 2-(2-, 3- or 4-pyridyl)-ethyl, 4-imidazolylmethyl, 2-(4-imidazolyl)-ethyl, 2- or 3-indolylmethyl, 2-(3-indolyl)-ethyl or 2-quinolylmethyl.

Hydroxy $R^a$ is unsubstituted or substituted, for example, by lower alkyl or aryl and is, for example, hydroxy, methoxy, ethoxy, n-butoxy, phenoxy, 4-hydroxyphenoxy or 3,4-methylenedioxyphenoxy.

Amino $R^a$ is unsubstituted or substituted by one or two lower alkyl groups or by aryl-loser alkyl, lower alkanoyl, lower alkoxycarbonyl or arylmethoxycarbonyl or is part of a five- or six-membered heterocycle containing one or two nitrogen atoms and, if desired, an oxygen or sulphur atom and is, for example, amino, methylamino, ethylamino, isopropylamino, n-butylamino, dimethylamino, diethylamino, benzylamino, acetylamino, pivaloylamino, methoxy-, ethoxy- or tert.-butoxycarbonylamino, benzyloxycarbonylamino, 1-pyrrolidinyl, 1-piperidinyl, 1-methyl-4-pyridazinyl, 4-morpholinyl or 4-thiomorpholinyl.

A is a bivalent residue of an α-amino acid, for example of a natural α-amino acid having the L-configuration, as is normal in proteins, of a homologue of such an amino acid, for example in which the amino acid side chain is lengthened or shortened by one or two methylene groups and/or a methyl group has been replaced by hydrogen, of a substituted aromatic α-amino acid, for example a substituted phenylalanine or phenylglycine, in which the substituent(s) may be lower alkyl, for example methyl, halogen, for example fluorine, chlorine, bromine or iodine, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert.-butoxycarbonylamino, arylmethoxycarbonylamino, for example benzyloxycarbonylamino, and/or nitro and occur(s) one or more times, of a benzo-fused phenylalanine or phenylglycine, such as α-naphthylalanine, or of a hydrogenated phenylalanine or phenylglycine, such as cyclohexylalanine or cyclohexylglycine, of a five- or six-membered cyclic, benzo-fused α-amino acid, for example indoline-2-carboxylic acid or 1,2,3,4-tetrahydroisoquinoline-3-carboxylic acid, of a natural or homologous α-amino acid in which a carboxy group of the side chain is in esterified or amidated form, for example in the form of a lower alkyl ester group, such as methoxycarbonyl or tert.-butoxycarbonyl, or in the form of a carbamoyl group, a lower alkylcarbamoyl group, such as methylcarbamoyl, or a di-lower alkylcarbamoyl group, such as dimethylcarbamoyl, in which an amino group of the side chain is in acylated form, for example in the form of a lower alkanoylamino group, such as acetylamino or pivaloylamino, in the form of a lower alkoxycarbonylamino group, such as tert.-butoxycarbonylamino, or in the form of an arylmethoxycarbonylamino group, such as benzyloxycarbonylamino, or in which a hydroxy group of the side chain is in etherified or esterified form, for example in the form of a lower alkoxy group, such as methoxy, in the form of an aryl-lower alkoxy group, such as benzyloxy, or in the form of a lower alkanoyloxy group, such as acetoxy, or A is a bivalent residue of an epimer of such an amino acid, that is to say having the non-naturally occurring D-configuration.

Such amino acids are, for example, glycine (H-Gly-OH), alanine (H-Ala-OH), valine (H-Val-OH), norvaline (α-aminovaleric acid), leucine, (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), proline (H-Pro-OH), trans-3- and trans-4-hydroxyproline, phenylalanine (H-Phe-OH), tyrosine (H-Tyr-OH), 4-nitrophenylalanine, 4-aminophenylalanine, 4-chlorophenylalanine, β-phenylserine (β-hydroxyphenylalanine), phenylglycine, α-naphthylalanine, cyclohexylalanine (H-Cha-OH), cyclohexylglycine, tryptophan (H-Trp-OH), indoline-2-carboxylic acid, 1,2,3,4-tetrahydroisoquinoline-3-carboxylic acid, aspartic acid (H-AspOH), asparagine (H-Asn-OH), aminomalonic acid, aminomalonic acid monoamide, glutamic acid (H-Glu-OH), glutamic acid mono-tert.-butyl ester, glutamine (H-Gln-OH), N$^\sigma$-dimethylglutamine, histidine (H-His-OH), arginine (H-Arg-OH), lysine (H-Lys-OH), N$^\epsilon$-tert.-butoxycarbonyl-lysine, δ-hydroxylysine, ornithine (α,δ-diaminovaleric acid), N$^\delta$-pivaloyl-ornithine, α,γ-diaminobutyric acid or α,β-diaminopropionic acid.

In order to increase the stability of the compound of the formula I towards enzymatic degradation, the amino acid residue A can be substituted N-terminally by lower alkyl, for example methyl or ethyl.

A is preferably the bivalent residue of alanine, valine, norvaline, leucine, norleucine, serine, etherified serine, proline, phenylalanine, β-phenylserine, α-naphthylalanine, cyclohexylalanine, indoline-2-carboxylic acid, 1,2,3,4-tetrahydroisoquinoline-3-carboxylic acid, aspartic acid, esterified aspartic acid, asparagine, aminomalonic acid, aminomalonic acid monoamide, glutamic acid, esterified glutamic acid, glutamine, di-lower alkylglutamine, histidine, lysine, acylated lysine, ornithine or acylated ornithine, if desired substituted N-terminally by lower alkyl, for example methyl. Very especially preferred as the group A is the bivalent residue of histidine, and also of serine and alanine.

Lower alkyl $R_2$ or $R_3$ has the meanings mentioned hereinbefore for lower alkyl $R^a$. Lower alkyl $R_2$ is preferably methyl or ethyl. Lower alkyl $R_3$ is preferably isopropyl, isobutyl, tert.-butyl, isopentyl, 2-methylbutyl or 2-ethylbutyl.

Hydroxy-lower alkyl $R_3$ or $R_5$ is preferably hydroxymethyl or hydroxyethyl and is optionally etherified or esterified by one of the groups indicated hereinafter for etherified or esterified hydroxy $R_4$.

Cycloalkyl $R_3$ or $R_5$ has the meanings mentioned hereinbefore for cycloalkyl $R^a$ or $R^b$ and is preferably cyclopentyl or cyclohexyl.

Cycloalkyl-lower alkyl $R_3$ or $R_5$ has the meanings mentioned hereinbefore for cycloalkyl-lower alkyl $R^a$ and is preferably cyclohexylmethyl.

Bicycloalkyl-lower alkyl $R_3$ or $R_5$ contains, for example, from 6 to 14, especially from 7 to 12, carbon atoms and is, for example, methyl or ethyl substituted by the radicals mentioned hereinbefore for bicycloalkyl $R^a$ or $R^b$, for example bicyclo[2.2.1]-hept-2-ylmethyl.

Tricycloalkyl-lower alkyl $R_3$ or $R_5$ contains, for example, from 9 to 14, especially from 10 to 12, carbon atoms and is, for example, methyl or ethyl substituted by the radicals mentioned hereinbefore for tricycloalkyl $R^a$ or $R^b$, preferably 1-adamantylmethyl.

Aryl $R_3$ or $R_5$ has the meanings mentioned hereinbefore for aryl $R^a$ or $R^b$ and is preferably phenyl.

Aryl-lower alkyl $R_3$ or $R_5$ has the meanings mentioned hereinbefore for aryl-lower alkyl $R^a$ and is preferably benzyl.

An etherified hydroxy group $R_4$ is preferably etherified by organic radicals that can be removed under physiological conditions and that, after removal, produce cleavage products that are pharmacologically harmless in the concentration concerned.

Etherified hydroxy $R_4$ is, for example, acyloxy-lower alkoxy in which acyl is the acyl group of an optionally branched lower alkanecarboxylic acid or of carbonic acid mono-esterified by optionally branched lower alkyl, for example lower alkanoyloxy-lower alkoxy, such as acetoxymethoxy, 1-acetoxyethoxy, pivaloyloxymethoxy or 1-pivaloyloxyethoxy, or lower alkoxycarbonyloxy-lower alkoxy, such as ethoxycarbonyloxymethoxy, 1-ethoxycarbonyloxyethoxy, tert.-butoxycarbonyloxymethoxy or 1-tert.-butoxycarbonyloxyethoxy.

Etherified hydroxy $R_4$ is also lower alkoxy, for example methoxy or ethoxy, aryloxy, for example phenoxy, or aryl-lower alkoxy, for example benzyloxy.

Esterified hydroxy $R_4$ is, for example, aliphatic acyloxy, for example lower alkanoyloxy, such as acetoxy or pivaloyloxy, cycloaliphatic acyloxy, for example cycloalkylcarbonyloxy, such as cyclohexylcarbonyloxy, or aromatic acyloxy, for example benzoyloxy.

Lower alkyl $R_5$ has from 1 to 7 carbon atoms and is, for example, methyl, ethyl, n-propyl, isopropyl, n-butyl, isobutyl, tert.-butyl or isopentyl. Methyl, isopropyl, isobutyl and tert.-butyl are especially preferred.

Bicycloalkyl $R_5$ has the meanings mentioned hereinbefore for bicycloalkyl $R^a$ or $R^b$ and is preferably α-decahydronaphthyl.

Tricycloalkyl $R_5$ has the meanings mentioned hereinbefore for tricycloalkyl $R^a$ or $R^b$ and is preferably 1-adamantyl.

Optionally substituted carbamoyl $R_5$ is unsubstituted or substituted by one or two lower alkyl or hydroxy-lower alkyl groups and is, for example, carbamoyl, methylcarbamoyl, ethylcarbamoyl, n-propylcarbamoyl, isopropylcarbamoyl, n-butylcarbamoyl, dimethylcarbamoyl, 2-hydroxyethylcarbamoyl or di(2-hydroxyethyl)-carbamoyl.

Optionally substituted amino $R_5$ is unsubstituted or substituted by one or two lower alkyl groups or by aryl-lower alkyl, lower alkanoyl, lower alkoxycarbonyl or arylmethoxycarbonyl or is part of a five- or six membered heterocycle containing one or two nitrogen atoms and, if desired, an oxygen or sulphur atom and is, for example, amino, methylamino, ethylamino, isopropylamino, n-butylamino, dimethylamino, diethylamino, benzylamino, acetylamino, pivaloylamino, methoxy-, ethoxy- or tert.-butoxy-carbonylamino, benzyloxycarbonylamino, 1-pyrrolidinyl, 1-piperidinyl, 1-methyl-4-pyridazinyl, 4-morpholinyl or 4-thiomorpholinyl, preferably dimethylamino.

Optionally substituted hydroxy $R_5$ is unsubstituted or etherified or esterified by one of the groups mentioned hereinbefore for etherified or esterified hydroxy $R_4$ and is, for example, hydroxy, methoxy, ethoxy, acetoxymethoxy, phenoxy, benzyloxy, acetoxy, pivaloyloxy or benzoyloxy.

Optionally substituted mercapto $R_5$ is unsubstituted or substituted by lower alkyl, for example methyl or ethyl, aryl, for example phenyl, aryl-lower alkyl, for example benzyl, lower alkanoyl, for example acetyl, or arylcarbonyl, for example benzoyl, and is, for example, mercapto, methylthio, ethylthio, phenylthio, benzylthio, acetylthio or benzoylthio.

Sulphinyl $R_5$ carries a lower alkyl group, for example methyl or ethyl, an aryl group, for example phenyl, or an aryl-lower alkyl group, for example benzyl, and is, for example, methylsulphinyl, ethylsulphinyl, phenylsulphinyl or benzylsulphinyl.

Sulphonyl $R_5$ carries a lower alkyl group, for example methyl or ethyl, an aryl group, for example phenyl, or an aryl-lower alkyl group, for example benzyl, and is, for example, methylsulphonyl, ethylsulphonyl, phenylsulphonyl or benzylsulphonyl, preferably methylsulphonyl.

Substituted amino $R_6$ is, for example, an amino group that is substituted by one or optionally two unsubstituted or substituted, saturated or unsaturated, aliphatic hydrocarbon radicals having up to and including 18, preferably up to and including 10, carbon atoms or by an unsubstituted or substituted, aromatic, heteroaromatic, aromatic-aliphatic or heteroaromaticaliphatic hydrocarbon radical having up to 18, preferably up to and including 10, carbon atoms.

Excluded as substituted amino $R_6$ is the radical of an α-amino acid or its N-substituted, esterified or amidated derivatives.

An unsubstituted or substituted, saturated or unsaturated, aliphatic hydrocarbon radical that substitutes the amino group $R_6$ is, for example, optionally substituted alkyl having up to 10 carbon atoms, lower alkenyl or lower alkynyl having up to and including 7 carbon atoms, or cycloalkyl-lower alkyl having from 4 to 10 carbon atoms. These radicals can be substituted, like lower alkyl $R^a$, by one or more of the functional groups mentioned hereinbefore, and by sulpho.

Preferred substituents are hydroxy, lower alkoxy, for example methoxy, lower alkanoyloxy, for example acetoxy, substituted or unsubstituted phenoxy, for example carbamoylphenoxy or carbamoyl-hydroxyphenoxy, carboxy, esterified carboxy, for example lower alkoxycarbonyl, such as methoxycarbonyl or tert.-butoxycarbonyl, or a physiologically cleavable esterified carboxy, for example 1-(lower alkanoyloxy)lower alkoxycarbonyl, such as acetoxymethoxycarbonyl, pivaloyloxymethoxycarbonyl or 1-propionyloxyethoxycarbonyl, 1-(lower alkoxycarbonyloxy)-lower alkoxycarbonyl, such as 1-(ethoxycarbonyloxy)-ethoxycarbonyl, or α-amino-lower alkanoyloxymethoxycarbonyl, such as α-aminoacetoxymethoxycarbonyl or (S)-α-amino-β-methylbutyryloxymethoxycarbonyl, carbamoyl, substituted or unsubstituted lower alkylcarbamoyl, for example hydroxy-lower alkylcarbamoyl, such as 2-hydroxyethylcarbamoyl or tris-(hydroxymethyl)-methylcarbamoyl, amino, lower alkylamino, for example methylamino, dilower alkylamino, for example dimethylamino, lower alkoxycarbonylamino, for example tert.-butoxycarbonylamino, guanidino, saturated five- or six-membered heterocyclyl that is bonded via a nitrogen atom and, if desired, substituted by oxo, for example 1-piperidinyl, 4-morpholinyl or 2-oxo-1-pyrrolidinyl, or sulpho.

An aromatic or aromatic-aliphatic hydrocarbon radical in a group $R_6$ preferably has the same meanings as those mentioned under aryl $R^a$ or $R^b$ or aryl-lower alkyl $R^a$ and is, for example, phenyl or phenyl-lower alkyl.

These radicals may be substituted in the aromatic moiety, for example by lower alkyl, for example methyl or ethyl, hydroxy, etherified hydroxy, for example lower alkoxy, such as methoxy or tert.-butoxy, esterified hydroxy, for example lower alkanoyloxy, such as acetoxy, or halogen, for example fluorine or chlorine, carboxy, esterified carboxy, for example lower alkoxycarbonyl, such as tert.-butoxycarbonyl, carbamoyl, amino, lower alkylamino, for example methylamino, di-lower alkylamino, for example dimethylamino, acylated amino, for example lower alkoxycarbonylamino, such as tert.-butoxycarbonylamino, also by nitro.

Lower alkyl in a phenyl-lower alkyl radical may be substituted by the same substituents as may alkyl in a radical $R_6$.

A heteroaromatic or heteroaromatic-aliphatic hydrocarbon radical in a group $R_6$ preferably has the same meanings as those mentioned under heteroaryl $R^a$ and $R^b$ or heteroaryl-lower alkyl $R^a$ and is, for example, pyridyl-lower alkyl, for example 2-, 3- or 4-pyridylmethyl, imidazolyl-lower alkyl, for example 2-(4-imidazolyl)-ethyl or also 2-(2-[4-imidazolyl]-ethylamino)-ethyl, or indolyl-lower alkyl, for example 3-indolylmethyl or 2-(3-indolyl)-ethyl.

Substituted amino $R_6$ is preferably alkylamino, for example methyl-, ethyl-, n-propyl-, isopropyl-, n-butyl-, isobutyl-, tert.-butyl-, n-pentyl-, isopentyl-, n-hexyl-, n-octyl- or n-decyl-amino, di-lower alkylamino, for example dimethylamino or diethylamino, hydroxy-lower alkylamino, for example 2-hydroxyethylamino, 2-hydroxybut-2-ylamino, 5-hydroxypentylamino or tris(hydroxymethyl)-methylamino, di-(hydroxy-lower alkyl)-amino, for example di-(2-hydroxyethyl)-amino, lower alkoxy-lower alkylamino, for example 2-methoxyethylamino, lower alkanoyloxy-lower alkylamino, for example 2-acetoxyethylamino, phenoxylower alkylamino or phenoxy-hydroxy-lower alkylamino in which phenoxy is optionally substituted by lower alkyl, lower alkoxy, hydroxy, carboxy, lower alkoxycarbonyl or by carbamoyl, for example 2-phenoxyethylamino, 2-(3-carbamoyl-4-hydroxyphenoxy)-ethylamino or 3-(3-carbamoylphenoxy)-2-hydroxypropylamino, carboxyalkylamino or amino-carboxy-alkylamino in which the carboxy radical is not in the 1-position of the alkyl radical, for example 4-carboxy-n-butylamino, 5-carboxy-n-pentylamino, 5-amino-5-carboxy-n-pentylamino, 6-carboxy-n-hexylamino, 7-carboxy-n-heptylamino or 8-carboxy-n-octylamino, also dicarboxymethylamino, lower alkoxycarbonylalkylamino or acylamino-lower alkoxycarbonylalkylamino in which the carbonyl radical is not in the 1-position of the alkyl radical, for example 4-tert.-butoxycarbonyl-n-butylamino, 5-tert.-butoxycarbonylamino-5-methoxycarbonyl-n-pentylamino, 7-tert.-butoxycarbonyl-n-heptylamino or 8-tert.-butoxycarbonyl-n-octylamino, also di-lower alkoxycarbonylmethylamino, for example di-methoxycarbonylmethylamino, physiologically cleavable esterified carboxyalkylamino in which the ester function is not in the 1-position of the alkyl radical, for example 4-pivaloyloxymethoxycarbonyl-n-butylamino, 7-(1-ethoxycarbonyloxyethoxycarbonyl)-n-heptylamino or 7-pivaloyloxymethoxycarbonyl-n-heptylamino, carbamoylalkylamino or hydroxy-lower alkylcarbamoylalkylamino in which the carbamoyl radical is not in the 1-position of the alkyl radical, for example 4-carbamoyl-n-butylamino, 7-carbamoyl-n-heptylamino or 4-(tris[hydroxymethyl]-methyl)-carbamoyl-n-butylamino, also dicarbamoyl-methylamino, di-(lower alkylcarbamoyl)-methylamino, for example di-(methylcarbamoyl)-methylamino, di-(hydroxy-lower alkylcarbamoyl)-methylamino, for example di-(2-hydroxyethylcarbamoyl)-methylamino, or bis-(di-lower alkylcarbamoyl)-methylamino, for example bis-(dimethylaminocarbamoyl)-methylamino, amino-lower alkylamino, for example 2-aminoethylamino or 4-aminobutylamino, lower alkylamino-lower alkylamino, for example 2-methylaminoethylamino, di-lower alkylamino-lower alkylamino, for example 2-dimethylaminoethylamino or 3-dimethylaminopropylamino, lower alkoxycarbonylamino-lower alkylamino, for example 2-(tert.-butoxycarbonylamino)-ethylamino, guanidino-lower alkylamino, for example 2-guanidinoethylamino, saturated five- or six-membered heterocyclyl-lower alkylamino that is bonded via a nitrogen atom, for example 2-(4-morpholinyl)ethylamino, 3-(4-morpholinyl)-propylamino or 3-(2-oxo-1-pyrrolidinyl)-propylamino, lower alkenylamino, for example allylamino or 2- or 3-butenylamino, lower alkynylamino, for example propargylamino, cycloalkyl lower alkylamino, for example cyclopropylmethylamino or cyclohexylmethylamino, phenylamino or phenyl-lower alkylamino in which phenyl is optionally mono- or polysubstituted by lower alkyl, for example methyl, hydroxy, lower alkoxy, for example methoxy or tert.-butoxy, lower alkanoyloxy, for example acetoxy, halogen, for example fluorine or chlorine, carboxy, lower alkoxycarbonyl, for example tert.-butoxycarbonyl, carbamoyl, amino, lower alkylamino for example methylamino, di-lower alkylamino, for example dimethylamino, acylamino, for example tert.-butoxycarbonylamino and/or by nitro, for example phenylamino, 2-, 3- or 4-methylphenylamino, 4-hydroxyphenylamino, 4-methoxyphenylamino, 2,3-, 2,4- or 2,5-dimethoxyphenylamino, 4-chlorophenylamino, 2-, 3- or 4-carboxyphenylamino, 2-, 3- or 4-methoxy- or tert.-butoxycarbonylphenylamino, 2-, 3- or 4-carbamoylphenylamino, 4-aminophenylamino, 4-tert.-butoxycarbonylaminophenylamino or 4-nitrophenylamino, also, for example, benzylamino, 4-methylbenzylamino, 4-methoxybenzylamino, 2-, 3- or 4-carboxybenzylamino, 2-, 3- or 4-tert.-butoxycarbonylbenzylamino, 2-, 3- or 4-carbamoylbenzylamino, 2-phenylethylamino or 3-phenylpropylamino, pyridyl-lower alkylamino, for example 2-, 3- or 4-pyridylmethylamino, 2-(2-, 3- or 4-pyridyl)-ethylamino or 3-(2-, 3- or 4-pyridyl)-propylamino, imidazolyllower alkylamino, for example 4-imidazolylmethylamino, 2-(4-imidazolyl)-ethylamino or 2-(2-[4-imidazolyl]-ethylamino)-ethylamino, indolyl-lower alkylamino, for example 3-indolylmethylamino or 2-(3-indolyl)-ethylamino, or sulpho-lower alkylamino, for example 2-sulphoethylamino.

Salts are especially the pharmaceutically acceptable non-toxic salts of compounds of the formula I.

Such salts are formed, for example, by compounds of the formula I having an acidic group, for example a carboxy group, and are, especially, suitable alkali metal salts, for example sodium or potassium salts, or suitable alkaline earth metal salts, for example magnesium or calcium salts, and also zinc salts or ammonium salts, and also those salts which are formed with organic amines, such as optionally hydroxysubstituted mono-, di- or tri-alkylamines, for example diethylamine, di-(2-hydroxyethyl)-amine, triethylamine, N,N-dimethyl-N-(2-hydroxyethyl)-amine, tri-(2-hydroxyethyl)-amine or N-methyl-D-glucamine. The compounds of the formula I having a basic group, for example an amino group, can form acid addition salts, for example with inorganic acids, for example hydrochloric acid, sulphuric acid or phosphoric acid, or with organic carboxylic, sulphonic or sulpho acids, for example acetic acid, propionic acid, glycolic acid, succinic acid, maleic acid, hydroxymaleic acid, methylmaleic acid, fumaric acid, malic acid, tartaric acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and with amino acids, such as, for example, the α-amino acids mentioned hereinbefore, and also with methanesulphonic acid, ethanesulphonic acid, 2-hydroxyethanesulphonic acid, ethane-1,2-disulphonic acid, benzenesulphonic acid, 4-methylbenzenesulphonic acid or naphthalene-2-sulphonic acid, or with other acidic organic compounds, such as ascorbic acid. Compounds of the formula I having acidic and basic groups can also form internal salts.

For the purposes of isolation or purification it is also possible to use pharmaceutically unsuitable salts.

The compounds of the present invention exhibit enzyme-inhibiting activity; in particular, they inhibit the action of the natural enzyme resin. The latter passes from the kidneys into the blood and there brings about the cleavage of angiotensinogen to form the decapeptide angiotensin I which is then cleaved in the lungs, the kidneys and other organs to form the octapeptide angiotensin II. The latter raises the blood pressure both directly through arterial constriction and indirectly through releasing from the adrenal glands the hormone aldosterone which retains sodium ions, thereby involving an increase in the extracellular fluid volume. This increase is to be attributed to the action of angiotensin II itself or of the heptapeptide angiotensin III formed therefrom as a cleavage product. Inhibitors of the enzymatic activity of resin bring about a reduction in the formation of angiotensin I. As a consequence of this, less angiotensin II is produced The reduced concentration of this active peptide hormone is the direct cause of the blood pressure-reducing action of renin-inhibitors.

The action of resin-inhibitors is demonstrated experimentally inter alia by means of in vitro tests, the reduction in the formation of angiotensin I being measured in various systems (human plasma, purified human resin together with synthetic or natural resin substrate). The following in vitro test inter alia is used: An extract of human resin from the kidney (0.5 mGU [milli-Goldblatt units]/ml) is incubated for one hour at 37° C. and pH 7.2 in 1 molar aqueous 2-N-(tris-hydroxymethylmethyl)-amino-ethanesulphonic acid buffe solution with 23 μg/ml of synthetic resin substrate, the tetradecapeptide H-Asp-Arg-Val-Tyr-Ile-His-Pro-Phe-His-Leu-Leu-Val-Tyr-Ser-OH. The amount of angiotensin I formed is ascertained in a radioimmunoassay. The inhibiting substances according to the invention are each added to the incubation mixture in different concentrations. $IC_{50}$ denotes that concentration of the particular inhibiting substance which reduces the formation of angiotensin I by 50%. In the in vitro systems, the compounds of the present invention exhibit inhibiting actions at minimum concentrations of from approximately $10^{-7}$ to approximately $10^{-10}$ mol/liter.

In animals depleted of salt the renin-inhibitors bring about a fall in blood pressure Human renin differs from renin of other species Primates (marmosets, *Callithrix jacchus*) are used for testing inhibitors of human renin since human renin and primate renin are to a great extent homologous in the enzymatically active range. The following in vivo test inter alia is used: The test compounds are tested in conscious normotensive marmosets of both sexes having a body weight of approximately 300 g. Blood pressure and heart rate are measured by means of a catheter in the femoral artery. The endogenous release of renin is stimulated by intravenous injection of furosemide (5 mg/kg). 30 minutes after the injection of furosemide, the test substances are either administered via a catheter in the lateral caudal vein by a single injection or by continuous infusion or they are administered perorally directly into the stomach in the form of a solution or suspension, and their effect on the blood pressure and heart rate is evaluated. The compounds of the present invention are effective in the described in vivo test in doses of from approximately 0.1 to approximately 1.0 mg/kg i.v. and in doses of from approximately 1.0 to approximately 10 mg/kg p.o.

The compounds of the present invention can be used as antihypertensives and also for the treatment of cardiac insufficiency.

The invention relates especially to compounds of the formula I in which $R_1$ represents an acyl group of a saturated or unsaturated, aliphatic, cycloaliphatic, cycloaliphatic-aliphatic, aromatic, aromaticaliphatic, heteroaromatic or heteroaromatic-aliphatic carboxylic acid, with the exception of the optionally N-substituted natural amino acid methionine, which acyl group is substituted by a thio, sulphinyl or sulphonyl group and optionally by other groups containing hetero atoms, A represents an optionally N-alkylated α-amino acid residue that is bonded N-terminally to $R_1$ and C-terminally to the group —$NR_2$—, $R_2$ represents hydrogen or lower alkyl, $R_3$ represents hydrogen, lower alkyl, hydroxy-lower alkyl, cycloalkyl, cycloalkyl-lower alkyl, bicycloalkyl-lower alkyl, tricycloalkyl-lower alkyl, aryl or aryl-lower alkyl, $R_4$ represents hydroxy, $R_5$ represents lower alkyl having 2 or more carbon atoms, hydroxy-lower alkyl, cycloalkyl, cycloalkyl-lower alkyl, bicycloalkyl, bicycloalkyl-lower alkyl, tricycloalkyl, tricycloalkyllower alkyl, carbamoyl, lower alkylcarbamoyl, di-lower alkylamino, aryl or aryl-lower alkyl, and $R_6$ represents an amino group that is substituted by one or optionally two unsubstituted or substituted, saturated or unsaturated aliphatic hydrocarbon radical(s) having up to and including 18, preferably up to and including 10, carbon atoms, or by an unsubstituted or substituted aromatic, heteroaromatic, aromatic-aliphatic or heteroaromatic-aliphatic hydrocarbon radical having up to and including 18, preferably up to and including 10, carbon atoms, with the exception of an amino radical derived from an α-amino acid, and to pharmaceutically acceptable salts of such compounds having salt-forming groups.

The invention relates more especially to compounds of the formula I in which $R_1$ represents a radical of the formula

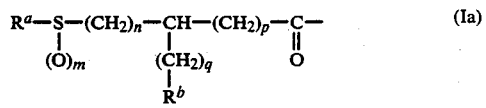

(Ia)

in which $R^a$ represents unsubstituted or substituted lower alkyl, for example methyl, ethyl, isopropyl, tert.-butyl, 2-hydroxyethyl, 2-methoxyethyl, 2-phenoxyethyl, 2-acetoxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl, 2-carbamoylethyl, 2-aminoethyl, 2-dimethylaminoethyl, 2-morpholinoethyl, 2-piperidinoethyl, 2-benzyloxycarbonylaminoethyl, 2-tert.-butoxycarbonylaminoethyl, 2-oxopropyl or 2-oxobutyl, lower alkenyl, for example vinyl, allyl or 2- or 3-butenyl, lower alkynyl, for example ethynyl, 1-propynyl or 2-propynyl, cycloalkyl, for example cyclopropyl, cyclobutyl, cyclopentyl or cyclohexyl, bicycloalkyl, for example bicyclo[2.2.1]-hept-2-yl, tricycloalkyl, for example 1-adamantyl, cycloalkyl-lower alkyl, for example cyclopropylmethyl, cyclobutylmethyl, cyclopentylmethyl or cyclohexylmethyl, unsubstituted or substituted aryl, for example phenyl, 1- or 2-naphthyl, o-, m- or p-methylphenyl, o-, m or p-hydroxyphenyl or o-, m- or p-aminophenyl, aryl-lower alkyl, for example benzyl, 2-phenylethyl or α- or β-naphthylmethyl, aryl-lower alkenyl, for example styryl or 3-phenylallyl, unsubstituted or substituted heteroaryl, for example 2- or 3-pyrrolyl, 2-furyl, 2-thienyl, 2- or 4-imidazolyl, 1-methyl-2-, -4- or -5-imidazolyl, 1,3-thiazol-2-yl, 2,-3- or 4-pyridyl, 1-oxido-2-, -3- or -4-pyridinio, 2-pyrazinyl, 2-, 4- or 5-pyrimidinyl, 2-, 3- or 4-quinolyl, 1-, 3- or 4-isoquinolyl or 2-benzoxazolyl, heteroaryl-lower alkyl, for example 2-, 3- or 4-pyridylmethyl, 2-(2-, 3- or 4-pyridyl)-ethyl, 4-imidazolylmethyl or 2-(4-imidazolyl)-ethyl, hydroxy, substituted hydroxy, for example lower alkoxy, for example methoxy, ethoxy or n-butoxy, or aryloxy, for example phenoxy, 4-hydroxyphenoxy or 3,4-methylenedioxyphenoxy, amino or substituted amino, for example lower alkylamino, for example methylamino, ethylamino, isopropylamino, n- or tert.-butylamino, di-lower alkylamino, for example dimethylamino or diethylamino, or amino as part of a five- or six-membered ring containing a nitrogen atom and, if desired, an oxygen atom, for example 1-pyrrolidinyl, 1-piperidinyl or 4-morpholinyl, $R^b$ represents hydrogen, cycloalkyl, for example cyclopentyl or cyclohexyl, bicycloalkyl, for example bicyclo[2.2.1]hept-2-yl, tricycloalkyl, for example 1-adamantyl, unsubstituted or substituted aryl, for example phenyl, 1- or 2-naphthyl, o-, m- or p-methylphenyl, o-, m- or p-hydroxyphenyl or o-, m- or p-aminophenyl, or unsubstituted or substituted heteroaryl, for example 2- or 4-imidazolyl, 2-, 3- or 4-pyridyl, 1-oxido-2-, -3- or -4-pyridinio or 2-, 4- or 5-pyrimidinyl, m represents 0, 1 or 2, preferably 2, n represents 0, 1 or 2, preferably 1, p represents 0, 1 or 2, preferably 0, and q represents 0, 1, 2, 3 or 4, preferably 1 or 2, A is a bivalent residue of an α-amino acid, for example of a natural α-amino acid having the L-configuration, as is normal in proteins, of a homologue of such an amino acid, for example in which the amino acid side chain is lengthened or shortened by one or two methylene groups and/or a methyl group has been replaced by hydrogen, of a substituted aromatic α-amino acid, for example a substituted phenylalanine or phenylglycine, in which the substituent(s) may be lower alkyl, for example methyl, halogen, for example fluorine, chlorine, bromine or iodine, hydroxy, lower alkoxy, for example methoxy, lower alkanoyloxy, for example acetoxy, amino, lower alkylamino, for example methylamino, di-lower alkylamino, for example dimethylamino, lower alkanoylamino, for example acetylamino or pivaloylamino, lower alkoxycarbonylamino, for example tert.-butoxycarbonylamino, arylmethoxycarbonylamino, for example benzyloxycarbonylamino, and/or nitro and occur(s) one or more times, of a benzo-fused phenylalanine or phenylglycine, such as α-naphthylalanine, or of a hydrogenated phenylalanine or phenylglycine, such as cyclohexylalanine or cyclohexylglycine, of a five- or six membered cyclic, benzofused α-amino acid, for example indoline-2-carboxylic acid or 1,2,3,4-tetrahydroisoquinoline-3-carboxylic acid, of a natural or homologous α-amino acid in which a carboxy group of the side chain is in esterified or amidated form, for example in the form of a lower alkyl ester group, such as methoxycarbonyl or tert.-butoxycarbonyl, or in the form of a carbamoyl group, a lower alkylcarbamoyl group, such as methylcarbamoyl, or a di-lower alkylcarbamoyl group, such as dimethylcarbamoyl, in which an amino group of the side chain is in acylated form, for example in the form of a lower alkanoylamino group, such as acetylamino or pivaloylamino, in the form of a lower alkoxycarbonylamino group, such as tert.-butoxycarbonylamino, or in the form of an arylmethoxycarbonylamino group, such as benzyloxycarbonylamino, or in which a hydroxy group of the side chain is in etherified or esterified form, for example in the form of a lower alkoxy group, such as methoxy, in the form of an aryl-lower alkoxy group, such as benzyloxy, or in the form of a lower alkanoyloxy group, such as acetoxy, or A is a bivalent residue of an epimer of such an amino acid, that is to say having the non-naturally occurring D-configuration, optionally substituted at the nitrogen atom by lower alkyl, for example methyl, $R_2$ represents hydrogen or lower alkyl, for example methyl, $R_3$ represents lower alkyl, for example isopropyl or isobutyl, cycloalkyl, for example cyclohexyl, cycloalkyl-lower alkyl, for example cyclopentylmethyl, cyclohexylmethyl, 2-cyclohexylethyl or cycloheptylmethyl, tricycloalkyl-lower alkyl, for example 1-adamantylmethyl, phenyl-lower alkyl, for example benzyl, or phenyl, $R_4$ represents hydroxy, $R_5$ represents lower alkyl, for example methyl, isopropyl, isobutyl or tert.-butyl, cycloalkyl, for example cyclopentyl or cyclohexyl, cycloalkyl-lower alkyl, for example cyclohexylmethyl, bicycloalkyl, for example α-decahydronaphthyl, tricycloalkyl, for example 1-adamantyl, phenyl, ohenyl-lower alkyl, for example benzyl, carbamoyl or lower alkylcarbamoyl, for example methylcarbamoyl, di-lower alkylamino, for example dimethylamino, hydroxy, lower alkoxy, for example methoxy, lower alkylthio, for example methylthio, or lower alkylsulphonyl, for example methylsulphonyl, and $R_6$ represents alkylamino having from 1 to 10 carbon atoms, for example methyl-, ethyl-, n-propyl-, isopropyl-, n-butyl-, isobutyl-, tert.-butyl-, n-pentyl-, isopentyl-, n-hexyl-, n-octyl- or n-decylamino, dilower alkylamino, for example dimethylamino or diethylamino, hydroxy-lower alkylamino, for example 2-hydroxyethylamino, 1-hydroxybut-2-ylamino, 5-hydroxypentylamino or tris-(hydroxymethyl)-methylamino, di-(hydroxy-lower alkyl)-amino, for example di-(2-hydroxyethyl)-amino, lower alkoxy-lower alkylamino, for example 2-methoxyethylamino, lower alkanoyloxy-lower alkylamino, for example 2-acetoxyethylamino, phenoxy-lower alkylamino or phenoxy-hydroxy-lower alkylamino in which phenoxy is optionally substituted by lower alkyl, lower alkoxy, hydroxy, carboxy, lower alkoxycarbonyl or by carbamoyl, for example 2-phenoxyethylamino, 2-(3-carbamoyl-4-hydroxyphenoxy)-ethylamino or 3-(3-carbamoylphenoxy)-2-hydroxypropylamino, carboxyalkylamino or amino-carboxyalkylamino in which the carboxy radical is not in the 1-position of the alkyl radical, for example 4-carboxy-n-butyl-, 5-carboxy-n-pentyl-, 6-carboxy-n-hexyl- 7-carboxy-n-heptyl- or 8-carboxy-n-octyl-amino or 5-amino-5-carboxy-n-pentylamino, also dicarboxymethylamino, lower alkoxycarbonylalkylamino or acylamino-lower alkoxycarbonyl-alkylamino in which the carbonyl radical is not in the 1-position of the alkyl radical, for example 4-tert.-butoxycarbonyl-n-butyl-, 7-tert.-butoxycarbonyl-n-heptyl- or 8-tert.-butoxycarbonyl-n-octyl-amino or 5-tert.-butoxycarbonylamino-5-methoxycarbonyl-n-pentylamino, also di-lower alkoxycarbonylmethylamino, for example dimethoxycarbonylmethylamino, physiologically cleavable esterified carboxyalkylamino in which the ester function is not in the 1-position of the alkyl radical, for example 4-pivaloyloxymethoxycarbonyl-n-butylamino, 7-(1-ethoxycarbonyloxyethoxycarbonyl)-n-heptylamino or 7-pivaloylox-mevthoxycarbonyln-heptylamino, carbamoyl- or hydroxy-lower alkylcarbamoyl-alkylamino in which the carbamoyl radical is not in the 1-position of the alkyl radical, for example 4-carbamoyl-n-butylamino, 7-carbamoyl-n-heptylamino or 4-(tris-[hydroxymethyl]-methyl)-carbamoyl-n-butylamino, also dicarbamoyl-methylamino, di-(lower alkylcarbamoyl)-methylamino, for example di-(methylcarbamoyl)-methylamino, di-(hydroxy-lower alkylcarbamoyl)-methylamino, for example di-(2-hydroxyethylcarbamoyl)-methylamino, or bis-(di-lower alkylcarbamoyl)-methylamino, for example bis-(dimethylcarbamoyl)-methylamino, aminolower alkylamino, for example 2-aminoethylamino or 4-aminobutylamino, lower alkylamino-lower alkylamino, for example 2-methylaminoethylamino, di-lower alkylamino-lower alkylamino, for example 2-dimethylaminoethylamino or 3-dimethylaminopropylamino, lower alkoxycarbonylamino-lower alkylamino, for example 2-(tert.-butoxycarbonylamino)-ethylamino, guanidino-lower alkylamino, for example 2-guanidinoethylamino, saturated five- or six-membered heterocyclyl-lower alkylamino that is bonded via a nitrogen atom, for example 2-(4-morpholinyl)-ethylamino, 3-(4-morpholinyl)propylamino or 3-(2-oxopyrrolidin-1-yl)-propylamino, lower alkenylamino, for example allylamino or 2- or 3-butenylamino, lower alkynylamino, for example propargylamino, cycloalkyl-lower alkylamino, for example cyclopropylmethylamino or cyclohexylmethylamino, phenylamino or phenyl-lower alkylamino in which phenyl is optionally mono- or polysubstituted by lower alkyl, for example methyl, hydroxy, lower alkoxy, for example methoxy or tert.-butoxy, lower alkanoyloxy, for example acetoxy, halogen, for example fluorine or chlorine, carboxy, lower alkoxycarbonyl, for example tert.-butoxycarbonyl, carbamoyl, amino, lower alkylamino, for example methylamino, di-lower alkylamino, for example dimethylamino, acylamino, for example tert.-butoxycarbonylamino and/or by nitro, for example phenyl-, 2-, 3- or 4-methylphenyl-, 4-hydroxyphenyl-, 4-methoxyphenyl-, 2,3-, 2,4- or 2,5-dimethoxyphenyl-, 4-chlorophenyl-, 2-, 3- or 4-carboxyphenyl-, 2-, 3- or 4-methoxy- or -tert.-butoxycarbonylphenyl-, 2-, 3- or 4-carbamoylphenyl-, 4-aminophenyl-, 4-tert.-butoxycarbonylaminophenyl- or 4-nitrophenyl-amino, also, for example, benzylamino, 4-methylbenzylamino, 4-methoxybenzylamino, 2-, 3- or 4-carboxybenzylamino, 2-, 3- or 4-tert.-butoxycarbonyl-benzylamino, 2-, 3- or 4-carbamoylbenzylamino, 2-phenylethylamino or 3-phenylpropylamino, pyridyl-lower alkylamino, for example 2-, 3- or 4-pyridylmethyl-, 2-(2-, 3- or 4-pyridyl)-ethyl- or 3-(2-, 3- or 4-pyridyl)-propyl-amino, imidazolyl-lower alkylamino, for example 4-imidazolylmethylamino, 2-(4-imidazolyl)-ethylamino or 2-(2-[4-imidazolyl]-ethylamino)-ethylamino, indolyl-lower alkylamino, for example 3-indolylmethylamino or 2-(3-indolyl)-ethylamino, or sulpho-lower alkylamino, for example 2-sulphoethylamino, and to pharmaceutically acceptable salts of these compounds having salt-forming groups.

The invention relates more especially to compounds of the formula I in which $R_1$ represents a radical of the formula

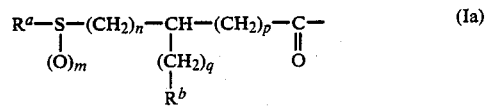

in which $R^a$ represents lower alkyl that is unsubstituted or substituted by hydroxy, lower alkoxy, phenoxy, lower alkanoyloxy, carboxy, lower alkoxycarbonyl or carbamoyl, for example methyl, ethyl, isopropyl, tert.-butyl, 2-hydroxyethyl, 2-methoxyethyl, 2-phenoxyethyl, 2-acetoxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl or 2-carbamoylethyl, cycloalkyl, for example cyclopentyl or cyclohexyl, cycloalkyl-lower alkyl, for example cyclopropylmethyl, cyclopentylmethyl or cyclohexylmethyl, aryl that is unsubstituted or substituted by lower alkyl, hydroxy or amino, for example phenyl, 1- or 2-naphthyl, o-, m or p-methylphenyl, m- or p-hydroxyphenyl or m- or p-aminophenyl, aryl-lower alkyl, for example benzyl, 2-phenylethyl or α- or β-naphthylmethyl, heteroaryl that is unsubstituted or substituted by oxido, lower alkyl or phenyl, for example 2- or 4-imidazolyl, 1-methyl-2-, -4- or -5-imidazolyl, 1,3-thiazol-2-yl, 2-, 3- or 4-pyridyl, 1-oxido-2-, -3- or -4-pyridinio, 2-pyrazinyl, 2-, 4- or 5-pyrimidinyl or 2-benzoxazolyl, heteroaryllower alkyl, for example 2-, 3- or 4-pyridylmethyl or 4-imidazolylmethyl, hydroxy, substituted hydroxy, for example lower alkoxy, for example methoxy, ethoxy or n-butoxy, or aryloxy, for example phenoxy, 4-hydroxyphenoxy or 3,4-methylenedioxyphenoxy, amino or substituted amino, for example lower alkylamino, for example methylamino, ethylamino, isopropylamino, n- or tert.-butylamino, di-lower alkylamino, for example dimethylamino or diethylamino, or amino as part of a five- or six-membered ring containing a nitrogen atom and, if desired, an oxygen atom, for example 1-pyrrolidinyl, 1-piperidinyl or 4-morpholinyl, $R^b$ represents hydrogen, cycloalkyl, for example cyclohexyl, aryl, for example phenyl or 1- or 2-naphthyl, or heteroaryl, for example 4-imidazolyl or 2-, 3- or 4-pyridyl, m represents 0, 1 or 2, n represents 0, 1 or 2, p represents 0, 1 or 2 and q represents 0, 1, 2 or 3, A represents the bivalent residue of the amino acids alanine, valine, norvaline, leucine, norleucine, serine proline, phenylalanine, β-phenylserine, α-naphthylalanine, cyclohexylalanine, indoline-2-carboxylic acid, 1,2,3,4-tetrahydroisoquinoline-3-carboxylic acid, aspartic acid, asparagine, aminomalonic acid, aminomalonic acid monoamide, glutamic acid, glutamine, dilower alkylglutamine, histidine, lysine or ornithine, it being possible for the carboxy group in the side chain of aspartic acid or glutamic acid to be esterified by a lower alkanol, for example methanol or tert.-butanol, for the hydroxy group in serine to be etherified by lower alkyl, for example methyl, or by benzyl, for the amino group in the side chain of lysine or ornithine to be acylated by lower alkanoyl, for example pivaloyl, by lower alkoxycarbonyl, for example tert.-butoxycarbonyl, or by arylmethoxycarbonyl, for example benzyloxycarbonyl, and/or for the o-nitrogen atom of the amino acids to be substituted by lower alkyl, for example methyl, R<sub>2</sub> represents hydrogen or lower alkyl, for example methyl, R<sub>3</sub> represents lower alkyl, for example isopropyl or isobutyl, cycloalkyl-lower alkyl, for example cyclopentylmethyl, cyclohexylmethyl, 2-cyclohexylethyl or cycloheptylmethyl, or tricycloalkyl-lower alkyl, for example 1-adamantylmethyl, R<sub>4</sub> represents hydroxy and R<sub>5</sub> represents lower alkyl, for example methyl, isopropyl or tert.-butyl, cycloalkyl, for example cyclopentyl or cyclohexyl, cycloalkyl-lower alkyl, for example cyclohexylmethyl, 1-adamantyl, benzyl, carbamoyl or lower alkylcarbamoyl, for example methylcarbamoyl, di-lower alkylamino, for example dimethylamino, hydroxy, lower alkoxy, for example methoxy, lower alkylthio, for example methylthio, or lower alkylsulphonyl, for example methylsulphonyl, and R<sub>6</sub> represents alkylamino having from 1 to 10 carbon atoms, for example methyl-, ethyl-, n-propyl-, isopropyl-, n-butyl-, isobutyl-, tert.-butyl-, n-pentyl-, isopentyl-, n-hexyl-, n-octyl- or n-decylamino, di-lower alkylamino, for example dimethylamino, hydroxy-lower alkylamino, for example 2-hydroxyethylamino, 1-hydroxybut-2-ylamino or tris(hydroxymethyl)methylamino, carboxyalkylamino or amino-carboxyalkylamino in which the carboxy radical is not in the 1-position of the alkyl radical for example 4-carboxy-n-butyl-, 5-carboxy-n-pentyl-, 6-carboxy-n-hexyl-, 7-carboxy-n-heptyl- or 8-carboxy-n-octyl-amino or 5-amino-5-carboxy-n-pentylamino, also dicarboxy-methylamino, lower alkoxycarbonylalkylamino or acylamino-lower alkoxycarbonyl-alkylamino in which the carbonyl radical is not in the 1-position of the alkyl radical, for example 4-tert.-butoxycarbonyl-n-butyl-, 7-tert.-butoxycarbonyl-n-heptyl- or 8-tert.-butoxycarbonyl-n-octyl-amino or 5-tert.-butoxycarbonylamino-5-methoxycarbonyl-n-pentylamino, also di-lower alkoxycarbonylmethylamino, for example dimethoxycarbonyl-methylamino, physiologically cleavable esterified carboxyalkylamino in which the ester function is not in the 1-position of the alkyl radical, for example 4-pivaloyloxymethoxycarbonyl-n-butylamino, 7-(1-ethoxycarbonyloxyethoxycarbonyl)-n-heptylamino or 7-pivaloyloxymethoxycarbonyln-heptylamino, carbamoyl- or hydroxy-lower alkylcarbamoyl-alkylamino in which the carbamoyl radical is not in the 1-position of the alkyl radical, for example 4-carbamoyl-n-butylamino, 7-carbamoyl-n-heptylamino or 4-(tris[hydroxymethyl]-methyl)-carbamoyl-n-butylamino, also dicarbamoyl-methylamino, di-(lower alkylcarbamoyl)methylamino, for example di-(methylcarbamoyl)-methylamino, di-(hydroxy-lower alkylcarbamoyl)-methylamino, for example di-(2-hydroxyethylcarbamoyl)-methylamino, or bis-(di-lower alkylcarbamoyl)-methylamino, for example bis-(dimethylcarbamoyl)-methylamino, aminolower alkylamino, for example 2-aminoethylamino or 4-aminobutylamino, lower alkylamino-lower alkylamino, for example 2-methylaminoethylamino, di-lower alkylaminolower alkylamino, for example 2-dimethylaminoethylamino, lower alkoxycarbonylamino-lower alkylamino, for example 2-(tert.-butoxycarbonylamino)-ethylamino, guanidino-lower alkylamino, for example 2-guanidinoethylamino, cycloalkyl-lower alkylamino, for example cyclopropylmethylamino, benzylamino, pyridyl-lower alkylamino, for example 2-, 3- or 4-pyridylmethylamino, 2-(2-, 3- or 4-pyridyl)-ethylamino or 3-(2-, 3- or 4-pyridyl)-propyl-amino, imidazolyl-lower alkylamino, for example 4-imidazolylmethylamino or 2-(4-imidazolyl)-ethylamino, indolyl-lower alkylamino, for example 3-indolylmethylamino or 2-(3-indolyl)-ethylamino, or sulpho-lower alkylamino, for example 2-sulphoethylamino, and to pharmaceutically acceptable salts of these compounds having salt-forming groups.

More especially preferred are compounds of the formula I in which R<sub>1</sub> represents a radical of the formula

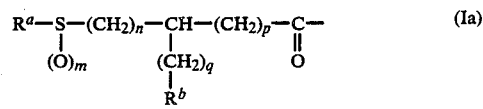

in which R<sup>a</sup> represents lower alkyl that is unsubstituted or substituted by hydroxy, lower alkoxy, phenoxy, lower alkanoyloxy, carboxy, lower alkoxycarbonyl or carbamoyl, for example methyl, ethyl, isopropyl, tert.-butyl, 2-hydroxyethyl, 2-methoxyethyl, 2-phenoxyethyl, 2-acetoxyethyl, carboxymethyl, 2-carboxyethyl, methoxycarbonylmethyl, 2-methoxycarbonylethyl, ethoxycarbonylmethyl, 2-ethoxycarbonylethyl, carbamoylmethyl or 2-carbamoylethyl, cycloalkyl, for example cyclopentyl or cyclohexyl, cycloalkyl-lower alkyl, for example cyclopropylmethyl, cyclopentylmethyl or cyclohexylmethyl, aryl that is unsubstituted or substituted by lower alkyl, hydroxy or amino, for example phenyl, 1- or 2-naphthyl, o-, m- or p-methylphenyl, m- or p-hydroxyphenyl or m-, or p-aminophenyl, aryl-lower alkyl, for example benzyl, 2-phenylethyl or α- or β-naphthylmethyl, heteroaryl that is unsubstituted or substituted by oxido, lower alkyl or phenyl, for example 2- or 4-imidazolyl, 1-methyl-2-, -4- or -5-imidazolyl, 1,3-thiazol-2-yl, 2-, 3- or 4-pyridyl, 1-oxido-2-, -3- or -4-pyridinio, 2-pyrazinyl, 2-, 4- or 5-pyrimidinyl, or 2-benzoxazolyl, or heteroaryl-lower alkyl, for example 2-, 3- or 4-pyridylmethyl or 4-imidazolylmethyl, hydroxy, substituted hydroxy, for example lower alkoxy, for example methoxy or ethoxy, amino or substituted amino, for example lower alkylamino, for example methylamino, ethylamino, isopropylamino, n- or tert.-butylamino, di-lower alkylamino, for example dimethylamino or diethylamino, or amino as part of a five- or six-membered ring containing a nitrogen atom and, if desired, an oxygen atom, for example 1-pyrrolidinyl, 1-piperidinyl or 4-morpholinyl, R<sup>b</sup> represents hydrogen, cycloalkyl, for example cyclohexyl, aryl, for example phenyl or 1-or 2-naphthyl, or heteroaryl, for example 4-imidazolyl or 2-, 3- or 4-pyridyl, m represents 0, 1 or 2, n represents 0 or 1, p represents 0, and q represents 1 or 2, A represents the bivalent residue of the amino acids alanine, serine, phenylalanine, N-methylphenylalanine, cyclohexylalanine, histidine or N-methyl-histidine, R<sub>2</sub> represents hydrogen, R<sub>3</sub> represents lower alkyl, for example isobutyl, or cycloalkyl-lower alkyl, for example cyclopentylmethyl, cyclohexylmethyl, 2-cyclohexylethyl or cycloheptylmethyl, R<sub>4</sub> represents hydroxy, R<sub>5</sub> represents lower alkyl, for example isopropyl, hydroxy, lower alkoxy, for example methoxy, lower alkylthio, for example methylthio, or lower alkylsulphonyl, for example methylsulphonyl, and R$_6$ represents lower alkylamino having from 1 to 7 carbon atoms, for example methyl-, ethyl-, n-propyl-, isopropyl-, n-butyl-, isobutyl-, n-pentyl- or isopentylamino, di-lower alkylamino, for example dimethylamino, hydroxy-lower alkylamino, for example 2-hydroxyethylamino, 1-hydroxybut-2-ylamino or 5-hydroxypentylamino, carboxyalkylamino or amino-carboxy-alkylamino in which the carboxy radical is not in the 1-position of the alkyl radical, for example 4-carboxy-n-butylamino, 7-carboxy-n-heptylamino or 8-carboxy-n-octylamino or 5-amino-5-carboxy-n-pentylamino, lower alkoxycarbonylalkylamino or acylamino-lower alkoxycarbonyl-alkylamino in which the carbonyl radical is not in the 1-position of the alkyl radical, for example 4-tert.-butoxycarbonyl-n-butylamino- or 7-tert -butoxycarbonyl-nheptylamino, or 5-tert.-butoxycarbonylamino-5-methoxycarbonyl-n-pentylamino, amino-lower alkylamino, for example 2-aminoethylamino or 4-aminobutylamino, di-lower alkylamino-lower alkylamino, for example 2-dimethylaminoethylamino or 3-dimethylaminopropylamino, lower alkoxycarbonylamino-lower alkylamino, for example 2-tert.-butoxycarbonylamino-ethylamino, morpholino-lower alkylamino, for example 2-morpholinoethylamino, pyridyl-lower alkylamino, for example 2-pyridylmethylamino, imidazolyl-lower alkylamino, for example 2-(4-imidazolyl)-ethylamino, or sulpho-lower alkylamino, for example 2-sulphoethylamino, and pharmaceutically acceptable salts of these compounds having salt-forming groups.

The invention relates especially to compounds of the formula I in which R$_1$ represents a radical of the formula

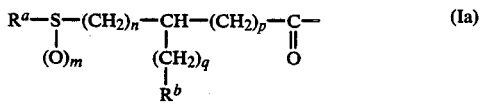 (Ia)

in which R$^a$ represents lower alkyl that is unsubstituted or substituted by hydroxy or lower alkoxy, for example methyl, ethyl, isopropyl, tert.-butyl, 2-hydroxyethyl or 2-methoxyethyl, phenyl, benzyl, or heteroaryl that has 1 or 2 nitrogen atoms and is unsubstituted or substituted by oxido or lower alkyl, for example 2- or 4-imidazolyl, 1-methyl-2-imidazolyl, 2-, 3- or 4-pyridyl, 1-oxido-2-, -3- or -4-pyridinio or 2-pyrimidinyl, R$^b$ represents cyclohexyl or phenyl, m represents 0, 1 or 2, n represents 1, p represents 0 and q represents 1 or 2, A represents the bivalent residue of the amino acid histidine, R$_2$ represents hydrogen, R$_3$ represents cyclohexylmethyl, R$_4$ represents hydroxy, R$_5$ represents isopropyl and R$_6$ represents lower alkylamino having from 1 to 7 carbon atoms, for example methyl-, ethyl-, n-propyl-, isopropyl-, n-butyl-, isobutyl-, n-pentyl- or isopentylamino, dimethylamino or 2-hydroxyethylamino, and to pharmaceutically acceptable salts of these compounds.

The invention relates more especially to compounds of the formula I in which R$_1$ represents a radical of the formula

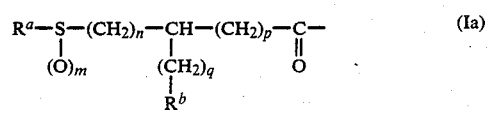 (Ia)

in which R$^a$ represents lower alkyl, for example methyl, ethyl, isopropyl or tert.-butyl, phenyl, 2-pyridyl, hydroxy, lower alkylamino, for example methylamino or isopropylamino, di-lower alkylamino, for example dimethylamino or diethylamino, or pyrrolidino, R$^b$ represents phenyl, m represents 2, n represents 1, o represents 0 and q represents 1, A represents the bivalent residue of the amino acid alanine, serine or histidine, R$_2$ represents hydrogen, R$_3$ represents cycloalkyl-lower alkyl, for example cyclopentylmethyl, cyclohexylmethyl, 2-cyclohexylethyl or cycloheptylmethyl, R$_4$ represents hydroxy, R$_5$ represents methyl, isopropyl, hydroxy, methoxy, methylthio or methylsulphonyl and R$_6$ represents lower alkylamino having from 1 to 4 carbon atoms, for example methylamino, ethylamino, n-propylamino or n-butylamino, 5-amino-5-carboxy-n-pentylamino, 4-aminobutylamino, 2-(4-imidazolyl)-ethylamino or 2-sulphoethylamino, and the carbon atoms carrying the radicals R$_3$ and R$_4$ have the S-configuration, and to pharmaceutically acceptable salts of these compounds.

The invention relates first and foremost to the compounds mentioned in the Examples and to their pharmaceutically acceptable salts, especially to the compound of the formula I in which R$_1$ represents a radical of the partial formula Ia in which R$^a$ represents tert.-butyl, R$^b$ represents phenyl, m represents 2, n represents 1, p represents 0 and q represents 1, A represents the..bivalent residue of the amino acid L-histidine, R$_2$ represents hydrogen, R$_3$ represents cyclohexylmethyl, R$_4$ represents hydroxy, R$_5$ represents isopropyl and R$_6$ represents n-butylamino, and the carbon atoms carrying the radicals R$_3$, R$_4$ and R$_5$, and the methine carbon atom in the partial formula Ia, have the S-configuration, and its pharmaceutically acceptable salts, the compound of the formula I in which R$_1$ represents a radical of the partial formula Ia in which R$^a$ represents tert.-butyl, R$^b$ represents phenyl, m represents 2, n represents 1, p represents 0 and q represents 1, A represents the bivalent residue of the amino acid L-histidine, R$_2$ represents hydrogen, R$_3$ represents cyclohexylmethyl, R$_4$ represents hydroxy, R$_5$ represents methyl and R$_6$ represents methylamino, and the carbon atoms carrying the radicals R$_3$ and R$_4$, and the methine carbon atom in the partial formula Ia, have the S-configuration and the carbon atom carrying the radical R$_5$ has the R-configuration, and its pharmaceutically acceptable salts, the compound of the formula I in which R$_1$ represents a radical of the partial formula Ia in which R$^a$ represents tert.-butyl, R$^b$ represents phenyl, m represents 2, n represents 1, p represents 0 and q represents 1, A represents the bivalent residue of the amino acid L-alanine, R$_2$ represents hydrogen, R$_3$ represents cyclohexylmethyl, R$_4$ represents hydroxy, R$_5$ represents isopropyl and R$_6$ represents n-butylamino, and the carbon atoms carrying the radicals R$_3$, R$_4$ and R$_5$, and the methine carbon atom in the partial formula Ia, have the S-configuration, and its pharmaceutically acceptable salts, the compound of the formula I in which $R_1$ represents a radical of the partial formula Ia in which $R^a$ represents tert.-butyl, $R^b$ represents phenyl, m represents 2, n represents 1, p represents 0 and q represents 1, A represents the bivalent residue of the amino acid L-histidine, $R_2$ represents hydrogen, $R_3$ represents cycloheptylmethyl, $R_4$ represents hydroxy, $R_5$ represents isopropyl and $R_6$ represents n-butylamino and the carbon atoms carrying the radicals $R_3$, $R_4$ and $R_5$, and the methine carbon atom in the partial formula Ia, have the S-configuration, and its pharmaceutically acceptable salts, and the compound of the formula I in which $R_1$ represents a radical of the partial formula Ia in which $R^a$ represents tert.-butyl, $R^b$ represents phenyl, m represents 2, n represents 1, p represents 0 and q represents 1, A represents the bivalent residue of the amino acid L-histidine, $R_2$ represents hydrogen, $R_3$ represents cyclohexylmethyl, $R_4$ represents hydroxy, $R_5$ represents isopropyl and $R_6$ represents methylamino, and the carbon atoms carrying the radicals $R_3$, $R_4$ and $R_5$, and the methine carbon atom in the partial formula Ia, have the S-configuration, and its pharmaceutically acceptable salts.

Processes

The compounds of the formula I according to the invention and salts of such compounds having at least one salt-forming group are obtained according to processes that are known per se, for example as follows:

(a) a fragment of a compound of the formula I having a terminal carboxy group or a reactive acid derivative of that fragment is condensed with a fragment that is complementary to the compound of the formula I and has a free amino group or with a reactive derivative thereof having an activated amino group to form an amide bond, any free functional groups present in the reactants, with the exception of the groups participating in the reaction, optionally being in protected form, or (b) for the manufacture of a compound of the formula I in which $R_4$ represents hydroxy, the keto group in a compound of the formula

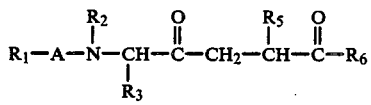

in which the substituents have the meanings mentioned and free functional groups, with the exception of the keto group participating in the reaction, are optionally in protected form, is reduced to a hydroxy group by reaction with a suitable reducing agent, or (c) for the manufacture of a compound of the formula I in which $R_4$ represents hydroxy, an aldehyde compound of the formula

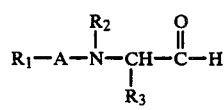

in which the substituents have the meanings mentioned and free functional groups, with the exception of the aldehyde group, are optionally in protected form, is reacted with an organometal compound of the formula

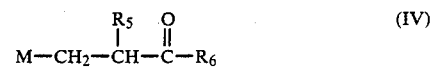

in which the substituents have the meanings mentioned and M represents a metal radical, and the resulting addition product is hydrolysed, or (d) in a compound of the formula

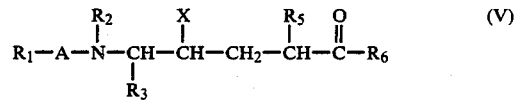

in which X represents a nucleofugal leaving group, the other substituents have the meanings mentioned above and free functional groups are optionally in protected form, the substituent X is exchanged for $R_4$ using a reagent that introduces the substituent $R_4$ in nucleophilic form, or (e) in a compound of the formula

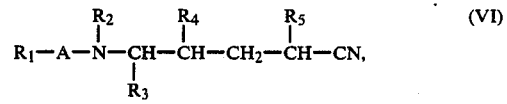

in which the substituents have the meanings mentioned and any functional groups present are optionally in protected form, the cyano group is converted into an N-substituted carboxamido group $-(C=O)R_6$, or (f) for the manufacture of a compound of the formula I in which $R_4$ represents free hydroxy, an epoxide of the formula

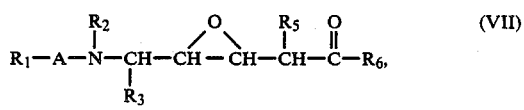

in which the substituents have the meanings mentioned and free functional groups are optionally in protected form, is reduced to the corresponding alcohol with a region selective reducing agent, or (g) for the manufacture of a compound of the formula I in which $R_1$ represents a radical of the formula

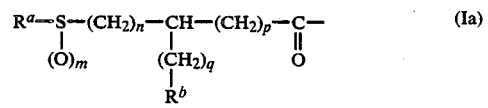

and m represents 0 or 2, n represents 1 and p represents 0, a compound of the formula $R^a\text{-}S(O)_mH$ or a salt thereof is added to a compound of the formula

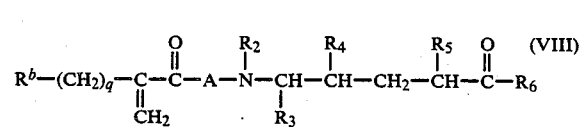

in which the substituents have the meanings mentioned and free functional groups are optionally in protected form, or (h) for the manufacture of a compound of the formula I in which $R_1$ represents a radical of the formula

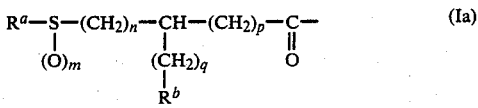

and p represents 0, a compound of the formula

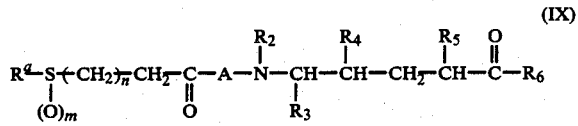

in which the substituents have the meanings mentioned and free functional groups are optionally in protected form, is alkylated with a compound that introduces the radical $R^b\text{-}(CH_2)q\text{-}$, and, if desired, (i) any protecting groups present in a resulting compound are removed and/or, if desired, after carrying out one of the processes (a)–(h) mentioned above or any other process for the manufacture of a compound of the formula I, a resulting compound of the formula I having a salt-forming group is converted into its salt or a resulting salt is converted into the free compound or into a different salt and/or resulting isomeric mixtures are optionally separated and/or, in a resulting compound of the formula I, the configuration of a chiral carbon atom is reversed and/or a compound of the formula I according to the invention is converted into a different compound of the formula I according to the invention.

The invention relates also to the compounds other than compounds of the formula I, obtainable according to any one of the processes mentioned above (by-product), and to compounds of the formula I and salts thereof that have been manufactured by a process other than one of those mentioned hereinbefore.

Process (a) (Production of an amide bond)

Fragments of a compound of the formula I having a terminal carboxy group that can be condensed with a fragment complementary to a compound of the formula I to form an amide bond are, for example, compounds of the formulae: $R_1$-OH, $R_1$-A-OH or

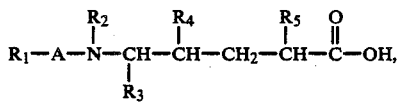

the activated esters or reactive anhydrides derived from these compounds, and also reactive cyclic amides. The reactive acid derivatives can also be formed in situ.

Activated esters are especially esters that are unsaturated at the linking carbon atom of the esterifying radical, for example of the vinyl ester type, such as vinyl esters (obtainable, for example, by transesterifying a corresponding ester with vinyl acetate; activated vinyl ester method), carbamoylvinyl esters (obtainable, for example, by treating the corresponding acid with an isoxazolium reagent; 1,2-oxazolium or Woodward method), or 1-lower alkoxyvinyl esters (obtainable, for example, by treating the corresponding acid with a lower alkoxyacetylene; ethoxyacetylene method), or esters of the amidino type, such as N,N'-disubstituted amidino esters (obtainable, for example, by treating the corresponding acid with a suitable N,N'-disubstituted carbodiimide, for example N,N'-dicyclohexylcarbodiimide; carbodiimide method), or N,N-disubstituted amidino esters (obtainable, for example, by treating the corresponding acid with an N,N-disubstituted cyanamide; cyanamide method), suitable aryl esters, especially phenyl esters substituted by electron-attracting substituents (obtainable, for example, by treating the corresponding acid with a suitably substituted phenol, for example 4-nitrophenol, 4-methylsulphonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treating the corresponding acid with chloroacetonitrile in the presence of a base; cyanomethyl esters method), thio esters, especially phenylthio esters optionally substituted, for example, by nitro (obtainable, for example, by treating the corresponding acid with thiophenols that are optionally substituted, for example, by nitro, inter alia with the aid of the anhydride or carbodiimide method; activated thio esters method), or especially amino or amido esters (obtainable, for example, by treating the corresponding acid with an N-hydroxyamino or N-hydroxyamido compound, for example N-hydroxysuccinimide, N-hydroxypiperidine, N-hydroxyphthalimide, N-hydroxy-5-norbornene- or -norbornane-2,3-dicarboxylic acid imide, 1-hydroxybenzotriazole or 3-hydroxy-3,4-dihydro-1,2,3-benzotriazin-4-one, for example according to the anhydride or carbodiimide method; activated N-hydroxyesters method).

Anhydrides of acids may be symmetric or preferably mixed anhydrides of these acids, for example anhydrides with inorganic acids, such as acid halides, especially acid chlorides (obtainable, for example, by treating the corresponding acid with thionyl chloride, phosphorus pentachloride or oxalyl chloride; acid chloride method), azides (obtainable, for example, from a corresponding acid ester by way of the corresponding hydrazide and the treatment of the latter with nitrous acid; azide method), anhydrides with carbonic acid semi-esters, for example carbonic acid lower alkyl semi-esters (obtainable, for example, by treating the corresponding acid with chloroformic acid lower alkyl esters, or with a 1-lower alkoxycarbonyl-2-lower alkoxy-1,2-dihydroquinoline, for example 1-ethoxycarbonyl-2-ethoxy-1,2-dihydroquinoline; mixed O-alkylcarbonic acid anhydrides method), anhydrides with dihalogenated, especially dichlorinated, phosphoric acid (obtainable, for example, by treating the corresponding acid with phosphorus oxychloride; phosphorus oxychloride method), anhydrides with other phosphoric acid derivatives (for example those which can be obtained with phenyl-N-phenylphosphoramidochloridate) or with phosphorous acid derivatives, or anhydrides with organic acids, such as mixed anhydrides with organic carboxylic acids (obtainable, for example, by treating the corresponding acid with an optionally substituted lower alkanecarboxylic acid halide or phenyl-lower alkanecarboxylic acid halide, for example phenylacetic acid chloride, pivalic acid chloride or trifluoroacetic acid chloride; mixed carboxylic acid anhydrides method) or with organic sulphonic acids (obtainable, for example, by treating a salt, such as an alkali metal salt, of the corresponding acid with a suitable organic sulphonic acid halide, such as a lower alkanesulphonic acid chloride or aryl-sulphonic acid chloride, for example methane- or p-toluene-sulphonic acid chloride; mixed sulphonic acid anhydrides method), and symmetric anhydrides (obtainable, for example, by condensing the corresponding acid in the presence of a carbodiimide or of 1-diethylaminopropyne; symmetric anhydrides method).

Suitable cyclic amides are especially amides having five-membered diazacycles of aromatic character, such as amides with imidazoles, for example imidazole (obtainable, for example, by treating the corresponding acid with N,N'-carbonyldiimidazole; imidazole method), or pyrazoles, for example 3,5-dimethylpyrazole (obtainable, for example, by way of the acid hydrazide by treatment with acetylacetone; pyrazolide method).

Fragments having a free amino group that are complementary to the compound of the formula I are, for example, depending on the meaning of $R_6$, a primary or secondary amine, or also compounds of the formula:

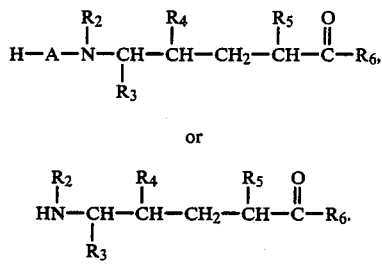

The amino group that participates in the reaction and is present in a fragment complementary to a compound of the formula I is preferably in free form, especially if the carboxy group reacting therewith is in reactive form; it can also, however, itself be derivatised, for example by reaction with a phosphite, such as diethyl chlorophosphite, 1,2-phenylene chlorophosphite, ethyl dichlorophosphite, ethylene chlorophosphite or tetraethyl pyrophosphite. A derivative of such a complementary fragment having an amino group is, for example, also a carbamic acid halide or an isocyanate, the amino group participating in the reaction being substituted by halocarbonyl, for example chlorocarbonyl, or modified in the form of an isocyanate group, it being possible in the latter case to obtain only compounds of the formula I that have a hydrogen atom at the nitrogen atom of the amide group formed by the reaction.

If the complementary fragment having an amino group is an amine mono- or di-substituted by lower alkyl or aryl-lower alkyl then a corresponding urea compound also constitutes a reactive derivative. For example, on heating equimolar amounts of this urea compound and the component having a free carboxy group, corresponding compounds of the formula I are obtained. If the complementary fragment is dimethylamine, then dimethylformamide is also a reactive derivative.

Functional groups in starting materials, the reaction of which is to be avoided, especially carboxy, amino, hydroxy, mercapto and sulpho groups, can be protected by suitable protecting groups that are customarily used in the synthesis of peptide compounds but also in the synthesis of cephalosporins and penicillins. These protecting groups may already be present in the precursors and are intended to protect the functional groups in question against undesired side-reactions, such as acylation, etherification, esterification, oxidation, solvolysis, etc. Protecting groups may, however, also be present in the end products. Compounds of the formula I having protected functional groups can have a higher metabolic stability than can the corresponding compounds having free functional groups.

The protection of functional groups by such protecting groups, the protecting groups themselves and the reactions by means of which they are removed are described, for example, in standard works, such as in J. F. W. McOmie, "Protective Groups in Organic Chemistry", Plenum Press, London and New York 1973, in Th. W. Greene, "Protective Groups in Organic Synthesis", Wiley, New York 1981, in "The Peptides", volume 3 (edited by E. Gross and J. Meienhofer), Academic Press, London and New York 1981, and in "Methoden der organischen Chemie", Houben-Weyl, 4th edition, vol. 15/I, Georg Thieme Verlag, Stuttgart 1974.

A carboxy group is protected, for example, in the form of an ester group that is selectively cleavable under mild conditions. A carboxy group protected in esterified form is esterified especially by a lower alkyl group that is branched in the 1-position of the lower alkyl group or substituted by suitable substituents in the 1- or 2-position of the lower alkyl group.

A protected carboxy group esterified by a lower alkyl group that is branched in the 1-position of the lower alkyl group is, for example, tert.-lower alkoxycarbonyl, for example tert.-butoxycarbonyl, or arylmethoxycarbonyl having one or two aryl radicals in which aryl is unsubstituted phenyl or phenyl mono-, di- or tri-substituted, for example, by lower alkyl, for example tert.-lower alkyl, such as tert.-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di-(4-methoxyphenyl)-methoxycarbonyl.

A protected carboxy group esterified by a lower alkyl group that is substituted by suitable substituents in the 1- or 2-position of the lower alkyl group is, for example, 1-lower alkoxy-lower alkoxycarbonyl, for example methoxymethoxycarbonyl, 1-methoxyethoxycarbonyl or 1-ethoxyethoxycarbonyl, 1-lower alkylthiolower alkoxycarbonyl, for example 1-methylthiomethoxycarbonyl or 1-ethylthioethoxycarbonyl, aroylmethoxycarbonyl, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, and also 2-tri-lower alkylsilyl-lower alkoxycarbonyl, for example 2-trimethylsilylethoxycarbonyl.

A carboxy group can also be protected in the form of an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonyl group may also be substituted by two lower alkyl groups, for example methyl groups, and by the amino group or the carboxy group of a second molecule of the formula I. Compounds having such protecting groups can be manufactured, for example, with dimethylchlorosilane as the silylating agent.

A protected carboxy group is preferably tert.-lower alkoxycarbonyl, for example tert.-butoxycarbonyl, benzyloxycarbonyl, 4-nitrobenzyloxycarbonyl or diphenylmethoxycarbonyl.

An amino group can be protected, for example, in the form of an acylamino, arylmethylamino, etherified mercaptoamino or silylamino group or in the form of an azido group.

In a corresponding acylamino group, acyl is, for example, the acyl radical of an organic carboxylic acid having, for example, up to 18 carbon atoms, especially of a lower alkanecarboxylic acid that is optionally substituted, for example, by halogen or aryl, or of benzoic acid that is optionally substituted, for example, by halogen, lower alkoxy or nitro, or preferably of a carbonic acid semi-ester. Such acyl groups are, for example, lower alkanoyl, such as formyl, acetyl, propionyl or pivaloyl, halo-lower alkanoyl, for example 2-haloacetyl, such as 2-chloro-, 2-bromo-, 2-iodo-, 2,2,2-trifluoro- or 2,2,2-trichloroacetyl, benzoyl optionally substituted, for example, by halogen, lower alkoxy or nitro, for example benzoyl, 4-chlorobenzoyl, 4-methoxybenzoyl or 4-nitrobenzoyl, or lower alkoxycarbonyl that is branched in the 1-position of the lower alkyl radical or suitably substituted in the 1- or 2-position, for example tert.-lower alkoxycarbonyl, such as tert.-butoxycarbonyl, arylmethoxycarbonyl having one or two aryl radicals which are phenyl optionally mono- or poly-substituted, for example, by lower alkyl, for example tert.-lower alkyl, such as tert.-butyl, lower alkoxy, such as methoxy, hydroxy, halogen, such as chlorine, and/or by nitro, for example benzyloxycarbonyl, 4-nitrobenzyloxycarbonyl, diphenylmethoxycarbonyl or di-(4-methoxyphenyl)-methoxycarbonyl, aroylmethoxycarbonyl, for example phenacyloxycarbonyl, 2-halo-lower alkoxycarbonyl, for example 2-chloroethoxycarbonyl, 2,2,2-trichloroethoxycarbonyl, 2-bromoethoxycarbonyl or 2-iodoethoxycarbonyl, 2-tri-lower alkylsilyl-lower alkoxycarbonyl, for example 2-trimethylsilylethoxycarbonyl, or 2-triarylsilyl-lower alkoxycarbonyl, for example 2-triphenylsilylethoxycarbonyl.

An arylmethylamino group is, for example, mono-, di- or, especially, tri-phenylmethylamino, for example benzyl-, diphenylmethyl- or trityl-amino.

In an etherified mercaptoamino group, the etherified mercapto group is especially substituted arylthio, for example 4-nitrophenylthio.

A silylamino group is, for example, a tri-lower alkylsilylamino group, for example trimethylsilylamino. The silicon atom of the silylamino group can also be substituted by only two lower alkyl groups, for example methyl groups, and by the amino group or carboxy group of a second molecule of the formula I. Compounds having such protecting groups can be manufactured, for example, with dimethylchlorosilane as the silylating agent.

Preferred amino-protecting groups are acyl radicals of carbonic acid semi-esters, especially tert.-butoxycarbonyl, optionally substituted benzyloxycarbonyl, for example 4-nitrobenzyloxycarbonyl, diphenylmethoxycarbonyl, 2-halo-lower alkoxycarbonyl, for example 2,2,2-trichloroethoxycarbonyl, and also trityl and formyl.

A hydroxy group can be protected, for example, by a lower alkanoyl group substituted by halogen, for example chlorine, for example 2,2-dichloroacetyl, or especially by a carbonic acid semi-ester acyl radical mentioned for protected amino groups. A preferred hydroxy-protecting group is, for example, 2-chloroethoxycarbonyl, 2,2,2-trichloroethoxycarbonyl, 4-nitrobenzyloxycarbonyl or diphenylmethoxycarbonyl. A hydroxy group can also be protected by tri-lower alkylsilyl, for example trimethylsilyl or, preferably, dimethyltert.-butylsilyl, a readily removable alkyl group, such as tert.-lower alkyl, for example tert.butyl, an oxa- or a thia-aliphatic or -cycloaliphatic hydrocarbon radical, for example 1-lower alkoxy-lower alkyl or 1-lower alkylthio-lower alkyl, for example methoxymethyl, 1-methoxyethyl, 1-ethoxyethyl, methylthiomethyl, 1-methylthioethyl or 1-ethylthioethyl, or 2-oxa- or 2-thiacycloalkyl having from 5 to 7 ring atoms, for example 2-tetrahydrofuryl or 2-tetrahydropyranyl, or a corresponding thia analogue, or also by 1-phenyl-lower alkyl, for example benzyl, diphenylmethyl or trityl, it being possible for the phenyl radicals to be substituted, for example, by halogen, for example chlorine, lower alkoxy, for example methoxy, and/or by nitro.

Two adjacent hydroxy groups can be protected, for example, by a preferably substituted methylene group, for example by lower alkylidene, for example isopropylidene, cycloalkylidene, for example cyclohexylidene, or benzylidene.

A mercapto group, such as, for example, in cysteine, can be protected especially by S-alkylation with optionally substituted alkyl radicals, silylation, thioacetal formation, S-acylation or by the formation of asymmetric disulphide groupings. Preferred mercapto-protecting groups are, for example, benzyl optionally substituted in the phenyl radical, for example by methoxy or nitro, such as 4-methoxybenzyl, diphenylmethyl optionally substituted in the phenyl radical, for example by methoxy, such as 4,4'-dimethoxydiphenylmethyl, triphenylmethyl, trimethylsilyl, benzylthiomethyl, 2-tetrahydropyranyl, acylaminomethyl, benzoyl, benzyloxycarbonyl, lower alkylaminocarbonyl, such as ethylaminocarbonyl, or also lower alkylthio, for example methylthio.

A sulpho group can be protected, for example, by lower alkyl, for example methyl or ethyl, or by phenyl, or it can be protected in the form of a sulphonamide, for example in the form of an imidazolide.

The condensation for the production of the amide bond can be carried out in a manner known per se, for example as described in standard works, such as Houben-Weyl, "Methoden der organischen Chemie", 4th edition, vol. 15/II, Georg Thieme Verlag, Stuttgart 1974, "The Peptides" (edited by E. Gross and J. Meienhofer), volumes 1 and 2, Academic Press, London and New York 1979/1980, or M. Bodanszky, "Principles of Peptide Synthesis", Springer-Verlag, Berlin 1984.

The condensation can be carried out in the presence of one of the customary condensation agents. Customary condensation agents are, for example, carbodiimides, for example diethyl-, dipropyl- or N-ethyl-N'-(3-dimethylaminopropyl)-carbodiimide or especially dicyclohexylcarbodiimide, also suitable carbonyl compounds, for example carbonyldiimidazole, 1,2-oxazolium compounds, for example 2-ethyl-5-phenyl-1,2-oxazolium 3'-sulphonate and 2-tert.-butyl-5-methylisoxazolium perchlorate, or a suitable acylamino compound, for example 2-ethoxy-1-ethoxycarbonyl-1,2-dihydroquinoline, or activated phosphoric acid derivatives, for example diphenylphosphoryl azide, diethylphosphoryl cyanide, phenyl-N-phenylphosphoramidochloridate, bis-(2-oxo-3-oxazolidinyl)-phosphinic acid chloride or 1-benzotriazolyloxy-tris-(dimethylamino)-phosphonium hexafluorophosphate.

If desired, an organic base is added, for example a tri-lower alkylamine having bulky radicals, for example ethyldiisopropylamine, or a heterocyclic base, for example pyridine, 4-dimethylaminopyridine or, preferably, N-methylmorpholine.

The condensation of acid anhydrides with amines can be effected, for example, in the presence of inorganic carbonates, for example alkali metal carbonates or hydrogen carbonates, such as sodium or potassium carbonate or sodium or potassium hydrogen carbonate (customarily together with a sulphate).

The condensation is preferably carried out in an inert, polar, aprotic, preferably anhydrous solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in mixtures thereof, optionally at reduced or elevated temperature, for example within a temperature range of from approximately −40° C. to approximately +100° C., preferably from approximately −10° C. to approximately +50° C., and optionally under an inert gas atmosphere, for example a nitrogen atmosphere.

Reactive acid derivatives can also be formed in situ. Thus, for example, N,N'-disubstituted amidino esters can be formed in situ by reacting the mixture of the fragment having a free carboxy group and the complementary fragment having an amino group in the presence of a suitable disubstituted carbodiimide, for example dicyclohexylcarbodiimide. Amino or amido esters of such acids can also be formed in the presence of the amino component to be acylated, by reacting the mixture of the corresponding acid and amino starting materials in the presence of a disubstituted carbodiimide, for example dicyclohexylcarbodiimide, and an N-hydroxylamine or N-hydroxyamide, for example N-hydroxybenzotriazole, N-hydroxysuccinimide or N-hydroxynorbornane-2,3-dicarboxylic acid imide, optionally in the presence of a suitable base, for example 4-dimethylaminopyridine, N-methylmorpholine or ethyldiisopropylamine.

The condensation of a carboxylic acid $R_1$-A-OH with the corresponding fragment that is complementary to the compound of the formula I and has a free amino group can also be achieved in a manner known per se using enzymes, for example as described by H.-D. Jakubke et al. in Angew. Chem. Int. Ed. Engl. 24. 85 (1985). Suitable enzymes are, for example, thermolysine, carboxypeptidase Y, papain, chymotrypsin, trypsin or pepsin. The reaction is preferably carried out in water or in mixtures of water with organic solvents, for example with lower alkanols, such as ethanol, dimethylformamide, dimethyl sulphoxide, ethers, such as tetrahydrofuran, dioxan or 1,2-dimethoxyethane, acetone acetonitrile or polyalcohols, for example ethylene glycol or di-, tri- or poly-ethylene glycol, but it can also be carried out with non-miscible organic solvents, for example methylene chloride or ethyl acetate, at a pH of from 5 to 8, preferably at approximately the neutral point, at temperatures of from 0° C. to 50° C. The solvents and the reaction conditions are preferably so chosen that the desired compound is formed or is extracted into the non-miscible organic phase and thus withdrawn from the reaction equilibrium. It is also possible to carry out the condensation with enzymes, such as those mentioned above, immobilised on a suitable carrier, in the mentioned organic solvents in admixture with a small amount of water.

Process (b) (Reduction of a keto group)

In a starting material of the formula II functional groups, with the exception of the keto group to be reduced, are optionally protected by one of the protecting groups mentioned under process (a).

For the reduction of the keto group in a compound of the formula II there are suitable those reducing agents which, under the reaction conditions of the process, reduce an isolated keto group selectively or more rapidly than the amide groups present in compounds of the formula I.

There are to be mentioned, especially, suitable borohydrides, such as alkali metal borohydrides, especially sodium borohydride, lithium borohydride or sodium cyanoborohydride, also zinc borohydride, or suitable aluminium hydrides, such as alkali metal lower alkoxyaluminium hydrides having bulky radicals, for example lithium tris-tert.-butoxyaluminium hydride.

The reduction can also be carried out with hydrogen in the presence of suitable heavy metal catalysts, for example Raney nickel or platinum or palladium catalysts, for example platinum on active carbon or palladium on active carbon, or according to the Meerwein-Ponndorf-Verley method with the aid of aluminium alkoxides, preferably aluminium 2propoxide or ethoxide.

The reduction can be carried out preferably with stoichiometric amounts or with a reasonably proportioned excess of the reducing agent, in an inert solvent at temperatures of from −80° C. to the boiling point of the solvent, preferably from −20° C. to 100° C., if necessary under a protective gas, for example nitrogen or argon. An excess of the reducing agent is necessary especially in cases where that agent also reacts with the solvent, for example with the protons of a protic solvent.

Suitable solvents when using sodium borohydride are polar, protic solvents, for example methanol, ethanol or isopropanol, and, when using the other reducing agents, the polar, aprotic solvents mentioned under process (a), for example tetrahydrofuran.

Process (c) (Addition of an organometal compound)

In a starting material of the formula III functional groups, with the exception of the aldehyde group, are optionally protected by the protecting groups mentioned under process (a). Functional groups present in a compound of the formula IV are likewise protected.

In a compound of the formula IV a metal radical -M is, for example, -Li or -MgHal, for example -MgCl, -MgBr or -MgI.

The reaction of a compound of the formula III with a compound of the formula IV is effected in customary manner in an anhydrous, inert, aprotic solvent, for example in an ether, such as diethyl ether or tetrahydrofuran, or a hydrocarbon, such as benzene or toluene, or mixtures thereof, optionally while cooling, especially after the beginning of the reaction, for example to approximately −30° C., or while heating, for example to the boiling temperature of the reaction mixture, optionally under an inert gas atmosphere, for example a nitrogen atmosphere. A preferred form of the process is the reaction of the aldehyde of the formula III with an excess of the lithium compound of the formula IV.

The hydrolysis of the addition product is effected with solvents that yield H+ ions, for example water (ice-water mixture) or dilute, aqueous acids, for example dilute mineral acids, such as dilute, aqueous sulphuric acid, or dilute organic acids, for example dilute, aqueous acetic acid.

The reaction of a compound of the formula III can also be effected with a compound of the formula IV that has been manufactured in situ and that is obtained, for example, from the corresponding halide, for example chloride, by reaction with a metallating agent, for example magnesium, lithium or tert.-butyllithium.

Process (d) (Nucleophilic substitution)

In a starting material of the formula V functional groups are optionally protected by the protecting groups mentioned under process (a).

In a compound of the formula V the nucleofugal leaving group X is especially hydroxy esterified by a strong inorganic or organic acid, such as a mineral acid, for example a hydrohalic acid, such as hydrochloric, hydrobromic or hydriodic acid, or sulphuric acid or halosulphuric acid, for example fluorosulphuric acid, or hydroxy esterified by a strong organic sulphonic acid, such as a lower alkanesulphonic acid optionally substituted, for example, by halogen, such as fluorine, or an aromatic sulphonic acid, for example a benzenesulphonic acid optionally substituted by lower alkyl, such as methyl, halogen, such as bromine, and/or by nitro, for example a methanesulphonic, trifluoromethanesulphonic or p-toluenesulphonic acid, or hydroxy esterified by hydrazoic acid.

A reagent that introduces the substituent $R_4$ in nucleophilic form is, depending on the meaning of $R_4$, a hydroxide-containing base, for example sodium or potassium hydroxide ($R_4$=OH), an alcohol, for example methanol or ethanol ($R_4$=etherified hydroxy) or the salt of a carboxylic acid, for example silver acetate ($R_4$=esterified hydroxy).

The reaction conditions are preferably so chosen that the reaction proceeds substantially as a second-order nucleophilic substitution ($S_N2$). For example, a compound of the formula V in which X represents a leaving group having high polarisability of the electron shell, for example iodine, can be reacted in a polar aprotic solvent, for example acetone, acetonitrile, nitromethane, dimethyl sulphoxide or dimethylformamide, with the silver salt of a carboxylic acid, for example silver acetate. The reaction with a hydroxide-containing base is preferably carried out in water to which there has optionally been added as solution aid an organic solvent, for example ethanol, tetrahydrofuran or acetone, and the reaction with an alcohol is preferably carried out in an excess of that alcohol, optionally in the presence of one of the polar aprotic solvents mentioned above. The substitution reaction is carried out optionally at reduced or elevated temperature, for example within a temperature range of from approximately −40° C. to approximately 100° C., preferably from approximately −10° C. to approximately +50° C., and optionally under an inert gas atmosphere, for example a nitrogen atmosphere.

Process (e) (Conversion of a cyano group into an amide group)

In a starting material of the formula VI functional groups are optionally protected by the protecting groups mentioned under (a).

The conversion of a compound of the formula VI into a compound of the formula I can be effected by a Ritter reaction or by way of carboxylic acid ester imide salts.

In the Ritter reaction, the nitriles are reacted in the presence of a strong acid, for example 85–90% sulphuric acid, or also polyphosphoric acid, hydrofluoric acid, formic acid, boron trifluoride or other Lewis acids, but not aluminium chloride, with compounds that are capable of forming carbenium ions in the acidic medium, that is to say, for example, with olefins, such as propylene, or alcohols, such as benzyl alcohol, in most cases without a solvent or, for example, in glacial acetic acid.

In a variant of the Ritter reaction, a nitrile of the formula VI is reacted with an olefin and mercury(II) nitrate and the organomercury compound is subsequently reduced with sodium borohydride to an N-substituted compound of the formula I.

By the acid-catalysed, preferably hydrochloric acid-catalysed, addition of alcohols to the nitriles of the formula VI, there are obtained carboxylic acid ester imides which yield amides of the formula I by thermal rearrangement at temperatures above approximately 80° C.

Process (f) (Reduction of the epoxide)

In a starting material of the formula VII functional groups are optionally protected by the protecting groups mentioned under process (a).

Those reducing agents may be used which, under the reaction conditions of the process, reduce the epoxy group selectively or more rapidly than the amide groups present and which open the epoxide in such a manner that a sufficient, and as large as possible, proportion of the reaction products carries the newly formed hydroxy group in the position corresponding to that of the formula I. Examples of such selective reducing agents are lithium borohydride or sodium cyanoborohydride/boron trifluoride etherate. Using the last-mentioned reagent the reaction can be carried out, for example, by adding a solution of boron trifluoride etherate, $BF_3.O(C_2H_5)_2$, in tetrahydrofuran to 1 mole of the compound of the formula VII and an excess, for example 1.4–3 moles, of sodium cyanoborohydride in tetrahydrofuran at elevated temperature, for example under reflux, in such a manner that the pH of the reaction solution is maintained close to the turning point of the indicator bromocresol green which has also been added. The reduction with lithium borohydride is preferably carried out in an ether, for example tetrahydrofuran, 1,2-dimethoxyethane or diethylene glycol dimethyl ether, at temperatures of from room temperature to the reflux temperature.

Process (g) (Addition to an acrylic amide)

A compound of the formula $R^a$-$S(O)_mH$ is either a thiol of the formula $R^a$-SH or a sulphinic acid of the formula $R^a$-$SO_2H$.

In a starting material of the formula VIII, functional groups are optionally protected by the protecting groups mentioned under process (a). Functional groups present in the compound of the formula $R^a$-$S(O)_mH$ are likewise optionally protected.

Suitable salts of the compound of the formula $R^a$-$S(O)_mH$ are, for example, alkali metal salts, for example sodium or potassium salts.

The addition of a compound of the formula $R^a$-$S(O)_mH$ or a suitable salt thereof to a compound of the formula VIII is carried out in customary manner in an inert polar solvent, for example in a polar ether, for example tetrahydrofuran, dioxan or dimethoxyethane, a lower alkanol, for example methanol, ethanol or isopropanol, or a dipolar aprotic solvent, for example dimethylformamide, dimethylacetamide, dimethyl sulphoxide, hexamethylphosphoric acid triamide, N-methylpyrrolidone or acetonitrile, or optionally in mixtures of the mentioned solvents with one another or with water, at temperatures of from approximately −30° C. to the boiling point of the particular solvent, for example at from 0° C. to +80° C., for example at approximately 50° C.

Instead of a sulphinic acid $R^a$-$SO_2H$, it is preferable to use its salts, for example the sodium or potassium salt.

A salt of a thiol of the formula $R^a$-SH can also be formed in situ, for example by adding a suitable base, for example an alkali metal hydroxide, such as sodium or potassium hydroxide, or an alkali metal hydride, for example sodium hydride, although only anhydrous solvents can be used. It is also possible to carry out the addition reaction with a free thiol of the formula $R^a$-SH in the presence of an organic base, for example a tertiary amine, for example triethylamine, N-methylmorpholine, dimethylaniline, diazabicyclo[5.4.0]undec-7-ene or diazabicyclo[4.3.0]non-5-ene.

Process (h) (Alkylation in the acyl radical)

In a starting material of the formula IX, functional groups are optionally protected by the protecting groups mentioned under process (a).

A compound that introduces the radical $R^b$-$(CH_2)_q$- is, for example, the corresponding halide, for example chloride, bromide or iodide, or a reactive ester of the corresponding alcohol, for example a sulphonic acid ester, such as the methanesulphonic acid ester or p-toluenesulphonic acid ester.

For the alkylation, the compound of the formula IX is preferably converted by customary methods with a strong non-nucleophilic base into the corresponding anion, for example with the lithium or potassium salt of a sterically hindered secondary amine, for example with lithium diisopropylamide, lithium cyclohexylisopropylamide, lithium-2,2,6,6-tetramethylpiperidide, lithium or potassium bis-(trimethylsilyl)-amide or the like. The deprotonation with the base is preferably carried out at low temperatures, for example at from −100° C. to −50° C., in an inert polar solvent, for example in a polar ether, for example tetrahydrofuran, dioxan or dimethoxyethane, optionally mixed with a hydrocarbon, for example hexane or toluene, and/or hexamethylphosphoric acid triamide or N,N'-dimethyl-N,N'-propyleneurea If the compound of the formula IX contains other methylene or methine groups from which the protons are more readily removed, for example next to the sulphinyl or sulphonyl group, then preferably two or more equivalents of the base are used in order to obtain the corresponding di- or poly-anion.

The compound of the formula IX so deprotonated is reacted with the alkylating agent introducing the radical $R^b$-$(CH_2)_q$- preferably in situ at low temperatures, for example at from −78° C. to −30° C., and with subsequent heating to room temperature or slightly elevated temperature, for example to 50° C., in the same solvent or solvent mixture.

If in a compound of the formula IX n represents 0, then the alkylation can be carried out under considerably milder conditions, for example in one of the above-mentioned solvents or in other polar solvents, for example dimethyl sulphoxide, dimethylformamide or acetonitrile, with the alkylating agent that introduces the radical $R^b(CH_2)q$- at temperatures of from −30° C. to approximately room temperature and with a tertiary amine, for example triethylamine, N-methylmorpholine, diazabicyclo[5.4.0]undec-7-ene or diazabicyclo[4.3.0]non-5-ene, or an insoluble inorganic base, for example potassium carbonate or sodium hydride, or an alcoholate, for example potassium tert.-butoxide. Also suitable is alkylation under phase transfer conditions, that is to say in a two-phase mixture comprising an aqueous base, for example sodium hydroxide solution, and an immiscible organic solvent, for example methylene chloride or toluene, and a phase transfer catalyst, for example an ammonium or phosphonium salt.

Process (i) (Subsequent operations)

In a resulting compound of the formula I in which $R_1$, A, $R_2$, $R_3$, $R_4$, $R_5$ and $R_6$ have the meanings mentioned, a carboxamide group can be substituted, a carboxy group present in free o reactive form can be esterified, and an esterified carboxy group can be converted into a carboxy group or into a carboxamide group.

Substitution of a carboxamide group or another amino group is effected, for example, by alkylation.

Suitable agents for alkylating a carboxamide group in a compound of the formula I are, for example, diazo compounds, for example diazomethane. Diazomethane can be decomposed in an inert solvent and the free methylene formed in so doing reacts with the carboxamide group in the compound of the formula I. The decomposition of diazomethane is preferably carried out by catalysis, for example in the presence of a noble metal in finely divided form, for example copper, or a noble metal salt, for example copper(I) chloride or copper(II) sulphate.

Further alkylating agents are those mentioned in German Offenlegungsschrift No. 2 331 133, for example alkyl halides, sulphonic acid esters, Meerwein salts or 1-substituted 3-aryltriazenes, which can be reacted with a compound of the formula I having a carboxamide group under the reaction conditions mentioned in that specification.

For the esterification of a carboxy group in a compound of the formula I the free acid can be used or the free acid can be converted into one of the reactive derivatives mentioned under process (a) and reacted with an alcohol, or the free acid or a reactive salt, for example the caesium salt, can be reacted with a reactive derivative of an alcohol. For example, the caesium salt of a carboxylic acid can be reacted with the halide of an alcohol.

The esterification of a carboxy group can be effected with the alkylating agents mentioned above for the substitution of the carboxamide group and under the same reaction conditions, for example with diazomethane, alkyl halides, sulphonic acid esters, Meerwein salts, 1-substituted 3-aryltriazenes, etc.

One of the methods described under process (a), removal of the carboxy-protecting groups, or, if desired, alkaline hydrolysis under the reaction conditions mentioned in "Organikum", 15th edition, VEB Deutscher Verlag der Wissenschaften, Berlin (East) 1976, can be used to convert an esterified carboxy group in a compound of the formula I into a free carboxy group.

In a compound of the formula I an esterified carboxy group can be converted into an optionally substituted carboxamide group by aminolysis with ammonia or a primary or secondary amine. The aminolysis can be effected under the reaction conditions mentioned for such reactions in "Organikum", 15th edition, VEB Deutscher Verlag der Wissenschaften, Berlin (East), 1976.

In a resulting compound of the formula I in which the substituents have the meanings mentioned and at least one free hydroxy group is present and the other functional groups are optionally in protected form, the free hydroxy group, for example the hydroxy group $R_4$, can be etherified or esterified.

The etherification of this hydroxy group can be effected with the alkylating agents mentioned above and under the same reaction conditions, for example with diazomethane, alkyl halides, sulphonic acid esters, Meerwein salts, 1-substituted 3-aryltriazenes, etc.

The esterification of the free hydroxy group can be effected with the customary acylating agents and the customary reaction conditions indicated in "Organikum", for example with acetic anhydride.

The mentioned alkylating reactions, etherifications, esterifications etc. can also be carried out in corresponding manner in a starting material instead of in the end product.

In a resulting compound of the formula I a thio group can be oxidised to a sulphinyl or sulphonyl group or a sulphinyl group can be oxidised to a sulphonyl group.

The oxidation to the sulphonyl group can be carried out with most of the customary oxidising agents. It is preferable to use those oxidising agents that oxidise the thio group or the sulphinyl group selectively in the presence of other functional groups, for example the amide function and the hydroxy group, of the compound of the formula I, for example aromatic or aliphatic peroxycarboxylic acids, for example perbenzoic acid, monoperphthalic acid, m-chloroperbenzoic acid, peracetic acid, performic acid or trifluoroperacetic acid. The oxidation with peroxycarboxylic acids is carried out in the customary solvents suitable for the purpose, for example chlorinated hydrocarbons, for example methylene chloride or chloroform, ether, ethyl acetate or the like, at temperatures of from −78° C. to room temperature, for example at from −20° C. to +10° C., preferably at approximately 0° C. The peroxycarboxylic acid can also be formed in situ, for example with hydrogen peroxide in acetic acid or formic acid, each of which optionally contains acetic anhydride, for example with 30% or 90% hydrogen peroxide in acetic acid/acetic anhydride. Other peroxo compounds are also suitable, for example potassium peroxomonosulphate in mixtures of lower alkanol and water, for example methanol and water or ethanol and water, or in aqueous acetic acid, at temperatures of from −70° C. to +30° C., for example from −20° C. to room temperature, also sodium metaperiodate in methanol or mixtures of methanol and water at temperatures of from 0° to 50° C., for example at approximately room temperature.

For the oxidation of the thio group to the sulphinyl group, selective oxidising agents are used in equimolar amounts or only a slight excess under controlled reaction conditions in order to prevent over-oxidation to the sulphonyl group. Suitable are, for example, sodium metaperiodate in methanol or mixtures of methanol and water at temperatures of from −15° C. to room temperature, for example at approximately 0° C., m-chloroperbenzoic acid in methylene chloride, chloroform or ethyl acetate at temperatures of from −78° C. to 10° C., preferably at from −30° C. to 0° C., also tert.-butyl hypochlorite in lower alkanols, for example methanol, or hydrogen peroxide in acetone or acetic acid at temperatures of approximately 0° C., or the above-mentioned potassium peroxomonosulphate at low temperatures.

In a resulting compound of the formula I having a sulphinyl group, this group can be reduced to a thio group. Selective reducing agents that leave other functional groups of the compound of the formula I, for example the amide function, unaltered are preferred Examples of such selective reducing agents are dichloroborane, which is preferably used in tetrahydrofuran or dimethoxyethane at temperatures of from −30° C. to +10° C., triphenylphosphine in boiling carbon tetrachloride, trichlorosilane or hexachlorodisilane, iron pentacarbonyl, also sodium hydrogen sulphite in aqueous-alcoholic solvents, for example water/methanol, water/ethanol or also water/tetrahydrofuran, at temperatures of from −10° C. to +50° C., also sodium borohydride in the presence of cobalt(II) chloride or also hydrogen in the presence of catalytic amounts of palladium, for example palladium-on-carbon in boiling ethanol.

If desired, a sulphonyl group in a resulting compound of the formula I can be reduced to a thio group, for example using diisobutylaluminium hydride in ether or tetrahydrofuran.

In a resulting compound of the formula I having a sulphonamide group, this group can be alkylated in the manner described for carboxamide groups or hydrolysed with an acid or an alkali to a sulpho group. For example, a sulphenamide group can be oxidised to the sulphonamide with one of the reagents mentioned under the oxidation of the thio group to the sulphonyl group, for example potassium peroxomonosulphate, and at the same time hydrolysed in situ. A sulphonic acid ester group can likewise be converted into a sulpho group by an acid or a base, for example as described above for the hydrolysis of a carboxylic acid ester group.

In a resulting compound of the formula I having a sulpho group, this group can be converted in known manner into a sulphonic acid ester group or a sulphonamide group, for example by conversion into a sulphonic acid halide group and reaction with an alcohol, phenol or amine. A sulphonic acid ester group is converted with an amine into the corresponding sulphonamide group analogously to the carboxylic acid ester group.

In a resulting compound of the formula I in which one or more functional groups are protected, these groups, for example carboxy, amino, hydroxy, mercapto and/or sulpho groups, can be freed in a manner known per se, optionally in stages or simultaneously, by means of solvolysis, especially hydrolysis, optionally enzymatic hydrolysis, alcoholysis or acidolysis, or by means of reduction, especially hydrogenolysis, or chemical reduction. The removal of the protecting groups is described in the standard works mentioned hereinbefore in the section "protecting groups".

For example, protected carboxy, for example tert. lower alkoxycarbonyl, lower alkoxycarbonyl substituted in the 2-position by an organic silyl group or in the 1-position by lower alkoxy or lower alkylthio, or optionally substituted diphenylmethoxycarbonyl, can be converted into free carboxy by treatment with a suitable acid, for example formic acid or trifluoroacetic acid, optionally with the addition of a nucleophilic compound, for example phenol or anisole. Optionally substituted benzyloxycarbonyl can be freed, for example, by means of hydrogenolysis, that is to say by treatment with hydrogen in the presence of a metallic hydrogenation catalyst, such as a palladium catalyst. Suitably substituted benzyloxycarbonyl, such as 4-nitrobenzyloxycarbonyl, can also be converted into free carboxy by reduction, for example by treatment with an alkali metal dithionite, for example sodium dithionite, or with a reducing metal, for example zinc, or a reducing metal salt, such as a chromium(II) salt, for example chromium(II) chloride, customarily in the presence of a hydrogen-yielding agent that together with the metal is capable of producing nascent hydrogen, such as an acid, especially a suitable carboxylic acid, such as an optionally substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or an alcohol or thiol, with water preferably being added. It is also possible to convert 2-halo-lower alkoxycarbonyl (optionally after converting a 2-bromo-lower alkoxycarbonyl group into a corresponding 2-iodo-lower alkoxycarbonyl group) or aroylmethoxycarbonyl into free carboxy by treatment with a reducing metal or a reducing metal salt, as described above. Aroylmethoxycarbonyl can also be cleaved by treatment with a nucleophilic, preferably salt-forming, reagent, such as sodium thiophenolate or sodium iodide. 2-tri-lower alkylsilyl-lower alkoxycarbonyl can also be converted into free carboxy by treatment with a salt of hydrofluoric acid yielding the fluoride anion, such as an alkali metal fluoride, for example sodium or potassium fluoride, optionally in the presence of a macrocyclic polyether ("Crown ether"), or with a fluoride of an organic quaternary base, such as tetra-lower alkylammonium fluoride or tri-lower alkylarylammonium fluoride, for example tetraethylammonium fluoride or tetrabutylammonium fluoride, in the presence of an aprotic, polar solvent, such as dimethyl sulphoxide or N,N-dimethylacetamide. Carboxy esterified by an organic silyl group, such as tri-lower alkylsilyl, for example trimethylsilyl, can be freed in customary manner by solvolysis, for example by treatment with water, an alcohol or an acid, or also a fluoride, as described above. Esterified carboxy can also be cleaved enzymatically, for example esterified arginine or lysine, such as lysine methyl ester, can be cleaved by means of trypsin.

A protected amino group is freed in a manner known per se and, depending on the nature of the protecting groups, by various methods, but preferably by solvolysis or reduction. 2-halo-lower alkoxycarbonylamino (optionally after converting a 2-bromo-lower alkoxycarbonylamino group into a 2-iodo-lower alkoxycarbonylamino group), aroylmethoxycarbonylamino or 4-nitrobenzyloxycarbonylamino can be cleaved, for example, by treatment with a suitable reducing agent, such as zinc in the presence of a suitable carboxylic acid, such as aqueous acetic acid. Aroylmethoxycarbonylamino can also be cleaved by treatment with a nucleophilic, preferably salt-forming, reagent, such as sodium thiophenolate, and 4-nitrobenzyloxycarbonylamino also by treatment with an alkali metal dithionite, for example sodium dithionite. Optionally substituted diphenylmethoxycarbonylamino, tert.-lower alkoxycarbonylamino or 2-tri-lower alkylsilyl-lower alkoxycarbonylamino can be freed by treatment with a suitable acid, for example formic acid or trifluoroacetic acid, optionally substituted benzyloxycarbonylamino can be freed, for example, by hydrogenolysis, i.e. by treatment with hydrogen in the presence of a suitable hydrogenation catalyst, such as a palladium catalyst, optionally substituted triarylmethylamino or formylamino can be freed, for example, by treatment with an acid, such as a mineral acid, for example hydrochloric acid, or an organic acid, for example formic acid, acetic acid or trifluoroacetic acid, optionally in the presence of water, and an amino group protected by an organic silyl group can be freed, for example, by hydrolysis or alcoholysis. An amino group protected by 2-haloacetyl, for example 2-chloroacetyl, can be freed by treatment with thiourea in the presence of a base, or with a thiolate salt, such as an alkali metal thiolate, of thiourea and by subsequent solvolysis, such as alcoholysis or hydrolysis, of the resulting substitution product. An amino group protected by 2-tri-lower alkylsilyl-lower alkoxycarbonyl can also be converted into the free amino group by treatment with a salt of hydrofluoric acid yielding fluoride anions, as indicated above in connection with the freeing of a correspondingly protected carboxy group. Silyl, such as trimethylsilyl, that is bonded directly to a hetero atom, such as nitrogen, can also be removed by means of fluoride ions.

Amino protected in the form of an azido group is converted into free amino, for example, by reduction, for example by catalytic hydrogenation with hydrogen in the presence of a hydrogenation catalyst, such as platinum oxide, palladium or Raney nickel, or also by treatment with zinc in the presence of an acid, such as acetic acid. The catalytic hydrogenation is preferably carried out in an inert solvent, such as a halogenated hydrocarbon, for example methylene chloride, or alternatively in water or a mixture of water and an organic solvent, such as an alcohol or dioxan, at approximately from 20° C. to 30° C., or alternatively while cooling or heating.

A hydroxy or mercapto group protected by a suitable acyl group, an organic silyl group or by optionally substituted 1-phenyl-lower alkyl is freed analogously to a correspondingly protected amino group. A hydroxy or mercapto group protected by 2,2-dichloroacetyl is freed, for example, by basic hydrolysis, while a hydroxy or mercapto group protected by tert.-lower alkyl or by a 2-oxa- or 2-thia-aliphatic or -cycloaliphatic hydrocarbon radical is freed by acidolysis, for example by treatment with a mineral acid or a strong carboxylic acid, for example trifluoroacetic acid. A silyl group, for example a trimethylsilyl or tert.-butyldimethylsilyl group, is likewise cleaved by acidolysis, for example by a mineral acid, preferably hydrofluoric acid, or a strong carboxylic acid 2-halo-lower alkoxycarbonyl is removed by the above-mentioned reducing agents, for example reducing metals, such as zinc, reducing metal salts, such as chromium(II) salts, or by sulphur compounds, for example sodium dithionite or, preferably, sodium sulphide and carbon disulphide.

Two hydroxy groups that are protected together by means of a preferably substituted methylene group, such as by lower alkylidene, for example isopropylidene, cycloalkylidene, for example cyclohexylidene, or benzylidene, can be freed by acid hydrolysis, for example in the presence of a mineral acid or a strong organic acid.

A sulpho group protected in the form of a sulphonic acid ester or sulphonamide is freed, for example, by acid hydrolysis, for example in the presence of a mineral acid, or preferably by basic hydrolysis, for example with alkali metal hydroxide or carbonate, for example sodium carbonate.

Salts of compounds of the formula I having salt-forming groups can be manufactured in a manner known per se. For example, salts f compounds of the formula I having acidic groups can be formed, for example, by treatment with metal compounds, such as alkali metal salts of suitable organic carboxylic acids, for example the sodium salt of 2-ethylhexanoic acid, or with inorganic alkali metal or alkaline earth metal salts, for example sodium hydrogen carbonate, or with ammonia or a suitable organic amine, preferably stoichiometric amounts or only a small excess of the salt-forming agent being used. Acid addition salts of compounds of the formula I are obtained in customary manner, for example by treatment with an acid or a suitable anion exchange reagent Internal salts of compounds of the formula I that contain, for example, a free carboxy group and a free amino group can be formed, for example, by neutralising salts, such as acid addition salts, to the isoelectric point, for example with weak bases, or by treatment with ion exchangers.

Salts can be converted in customary manner into the free compounds: metal and ammonium salts, for example, by treatment with suitable acids, and acid addition salts, for example, by treatment with a suitable basic agent.

Stereoisomeric mixtures, especially diastereoisomeric mixtures, can be separated into the individual isomers in a manner known per se, for example by fractional crystallisation, chromatography, etc.

Racemates can be split in a manner known per se, for example after converting the optical antipodes into diastereoisomers, for example by reaction with optically active acids or bases.

At individual chiral centres in a compound of the formula I, for example at the CH-$R_4$ C-atom, the configuration can be deliberately reversed For example, the configuration at the CH-$R_4$ C-atom can be reversed by second order nucleophilic substitution according to process (d) after converting the group $R_4$ into a nucleofugal leaving group X and reaction with a reagent that introduces the same substituent $R_4$.

The invention relates also to those forms of the process in which a compound obtainable as intermediate at any stage is used as starting material and the remaining steps are carried out or in which the process is discontinued at any stage or in which a compound obtainable in accordance with the process according to the invention is produced under the process conditions and further processed in situ.

Pharmaceutical preparations

The pharmacologically acceptable compounds of the present invention can be used, for example, for the manufacture of pharmaceutical preparations that contain an effective amount of the active ingredient together or in admixture with a significant amount of inorganic or organic, solid or liquid, pharmaceutically acceptable carriers.

The pharmaceutical preparations according to the invention are those for enteral, such as nasal, rectal or oral, administration or for parenteral, such as intramuscular or intravenous, administration to warm-blooded animals (humans and animals), which contain an effective dose of the pharmacological active ingredient on its own or together with a significant amount of a pharmaceutically acceptable carrier. The dosage of the active ingredient depends on the species of warm-blooded animal, the body weight, age and individual condition, on the disease to be treated and also on the mode of administration.

The dosages to be administered to warm-blooded animals, for example humans of approximately 70 kg body weight, are from approximately 3 mg to approximately 3 g, preferably from approximately 10 mg to approximately 1 g, for example approximately 300 mg per person per day, preferably divided into from 1 to 3 single doses which may, for example, be of equal size. Children usually receive half the adult dose.

The novel pharmaceutical preparations contain from approximately 1% to approximately 95%, preferably from approximately 20% to approximately 90%, active ingredient. Pharmaceutical preparations according to the invention may, for example, be in dosage unit form, such as ampoules, phials, suppositories, dragées, tablets or capsules.

The pharmaceutical preparations of the present invention are produced in a manner known per se, for example by means of conventional dissolving, lyophilising, mixing, granulating or confectioning processes.

There are preferably used solutions of the active ingredient, and also suspensions, especially isotonic aqueous solutions or suspensions, it being possible, for example in the case of lyophilised preparations which contain the active ingredient on its own or together with a carrier, for example mannitol, to prepare these before use. The pharmaceutical preparations may be sterilised and/or contain adjuncts, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The solutions or suspensions mentioned may contain substances that increase the viscosity, such as sodium carboxymethylcellulose, carboxymethylcellulose, dextran, polyvinylpyrrolidone or gelatine.

Suspensions in oil contain as oily component the vegetable, synthetic or semi-synthetic oils customary for injection purposes There may be mentioned as such especially liquid fatty acid esters that contain as acid component a long-chained fatty acid having from 8 to 22, especially from 12 to 22, carbon atoms, such as, for example, lauric acid, tridecylic acid, myristic acid, pentadecylic acid, palmitic acid, margaric acid, stearic acid, arachidic acid, behenic acid, or corresponding unsaturated acids, such as, for example, oleic acid, elaidic acid, erucic acid, brassidic acid or linoleic acid. The alcohol component of these fatty acid esters has at most 6 carbon atoms and is a mono-or poly-hydric, for example mono-, di- or tri-hydric, alcohol, for example methanol, ethanol, propanol, butanol or pentanol or their isomers, but above all glycol or glycerine. There may therefore be mentioned as examples of fatty acid esters: ethyl oleate, isopropyl myristate, isopropyl palmitate, "Labrafil M 2735" (polyoxyethylene glycerine trioleate manufactured by Gattefossé, Paris), "Myglyol 812" (triglyceride of saturated fatty acids of chain length $C_8$ to $C_{12}$, manufactured by Chemische Werke Witten/-

Ruhr, Germany), but especially vegetable oils, such as cotton seed oil, almond oil, olive oil, castor oil, sesame oil, soya bean oil and, above all, groundnut oil.

The manufacture of the injection preparations is effected in customary manner under sterile conditions, as is the introduction thereof into ampoules or phials and the sealing of the containers.

Pharmaceutical preparations for oral administration can be obtained by combining the active ingredient with solid carriers, optionally granulating a resulting mixture and, if desired or necessary after the addition of suitable adjuncts, processing the mixture or granulate into tablets or dragée cores. They can also be incorporated into plastics carriers which release the active ingredients, or allow them to diffuse, in a controlled manner.

Suitable carriers are especially fillers, such as sugars, for example lactose, saccharose, mannitol or sorbitol, cellulose preparations and/or calcium phosphates, for example tricalcium phosphate or calcium hydrogen phosphate, also binders, such as starch pastes using, for example, corn, wheat, rice or potato starch, gelatine, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, crosslinked polyvinylpyrrolidone, agar, alginic acid or a salt thereof, such as sodium alginate. Adjuncts are especially flow-regulating agents and lubricants, for example silica, talc, stearic acid or salts thereof, such as magnesium stearate or calcium stearate, and/or polyethylene glycol. Dragée cores are provided with suitable coatings that may be resistant to gastric juices, there being used, inter alia, concentrated sugar solutions which may contain gum arabic, talc, polyvinylpyrrolidone, polyethylene glycol and/or titanium dioxide, lacquer solutions in suitable organic solvents or solvent mixtures or, for the production of coatings that are resistant to gastric juices, solutions of suitable cellulose preparations, such as ethylcellulose phthalate or hydroxypropylmethylcellulose phthalate. Colourings or pigments can be added to the tablets or dragée coatings, for example for identification purposes or to indicate different doses of active ingredient.

Starting materials

The present invention relates also to novel starting materials and/or intermediates and to processes for the manufacture thereof. The starting materials and the reaction conditions are preferably so chosen that the compounds mentioned as being preferred are obtained.

The starting materials for carrying out process (a) can be manufactured according to processes that are known per se, for example from the relevant amino acids by condensation in a manner analogous to that of process (a) described hereinbefore.

For example, a compound of the formula

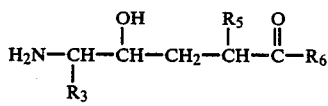  (X)

can be manufactured analogously to the process described in European Patent Application EP 143 746.

Compounds of the formula II are manufactured, for example, by reacting a carboxylic acid of the formula

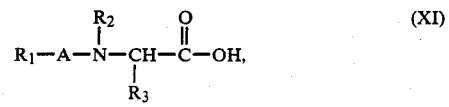  (XI)

or a suitable functional derivative thereof, in which the substituents have the meanings mentioned and free functional groups, with the exception of the optionally modified carboxy group, are optionally in protected form, with an organometal compound of the formula IV in which $R_5$ and $R_6$ have the meanings mentioned and M represents a metal radical, for example -Li or -MgHal, such as -MgCl, -MgBr or -MgI, and solvolysing the addition product formed.

Suitable functional derivatives of a carboxylic acid of the formula XI are, for example, the corresponding lithium salt of the carboxylic acid, a carboxylic acid halide, for example carboxylic acid chloride, an anhydride, for example the symmetrical carboxylic acid anhydride or a mixed carboxylic acid anhydride with a sterically hindered carboxylic acid, for example with pivalic acid, or a thio ester, for example 2-pyridylthio ester.

The reaction of a carboxylic acid of the formula XI or a suitable functional derivative thereof with a compound of the formula IV is carried out in the customary manner, for example under the reaction conditions indicated in process (c), but optionally while cooling, for example at temperatures of from approximately −50° C. to approximately 0° C. In a preferred form of the process, a 2-pyridylthio ester of the carboxylic acid of the formula XI is reacted with a bromomagnesium compound of the formula IV.

Compounds of the formula III can be manufactured according to processes that are known per se, for example by, in a compound of the formula XI in which the substituents have the meanings mentioned and free functional groups are optionally in protected form, reducing the carboxy group to the aldehyde function according to methods that are known per se, for example via the corresponding methyl or ethyl ester, via an imidazolide or via an N-methoxy-N-methylamide.

Compounds of the formula IV can be manufactured, for example, by reacting a known halide, or a halide that can be manufactured by methods known per se, of the formula

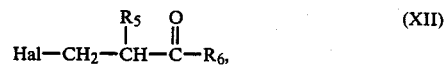  (XII)

for example the chloride, with a metallating agent, for example magnesium, lithium or tert.-butyllithium.

Compounds of the formula V are manufactured, for example, by reacting an aldehyde of the formula III with an organometal compound of the formula IV according to process (c) and esterifying the resulting hydroxy compound of the formula I, optionally after separating the isomers, with a strong organic or inorganic acid corresponding to the definition of X.

Nitriles of the formula VI are manufactured, for example, by reacting a compound of the formula

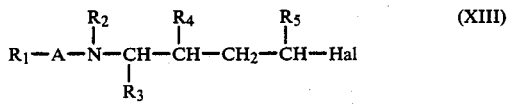

in which the substituents have the meanings mentioned, with a salt of hydrocyanic acid.

Suitable salts of hydrocyanic acid should be sufficiently soluble in the chosen inert solvent for a reaction to take place Such salts are, for example, ammonium cyanide, alkali metal cyanides or alkaline earth metal cyanides, for example sodium or potassium cyanide, or transition metal cyanides, for example copper cyanide. The transition metal cyanides are suitable owing to their lower basicity as compared with the alkali metal cyanides.

Depending on the nature of the cyanide used and the solvent, an equilibrium is established between the isomeric nitrile form and the isonitrile form. The nitrile form is formed preferentially if, for example, the reaction is effected with those metal cyanides of which the metal cations have a lower atomic weight than that of copper.

Suitable inert solvents are above all polar, aprotic solvents, for example carboxylic acid amides, for example dimethylformamide or dimethylacetamide, nitriles, for example acetonitrile or propionitrile, or di-lower alkyl sulphoxides, for example dimethyl sulphoxide.

The reaction is effected at room temperature, at reduced or at elevated temperature, for example within a temperature range of from approximately $-40°$ C. to approximately $+100°$ C., preferably from approximately $-10°$ C. to approximately $+50°$ C. and, if desired, under an inert gas atmosphere, for example a nitrogen atmosphere.

Epoxides of the formula VII are manufactured, for example, by reacting a compound of the formula

in which $Z_1$ is an amino-protecting group, with a phosphoranylidene compound of the formula

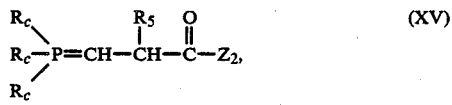

in which $R_c$ represents an optionally substituted hydrocarbon radical, $R_5$ has the meaning mentioned and $Z_2$ is a carboxy-protecting group, and converting a resulting compound of the formula

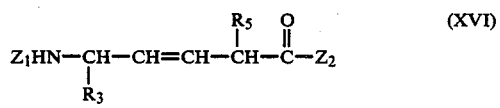

into an epoxide with an oxidising agent containing the peroxy group and, in a resulting compound, removing the protecting groups $Z_1$ and $Z_2$ and replacing them by the groups $R_1$-A- and $R_6$ in any desired sequence of the reaction steps.

$R_c$ is preferably phenyl. The reaction of a compound of the formula XIV with a phosphoranylidene compound of the formula XV is effected under the reaction conditions known for Wittig reactions and described, for example, in "Organikum". The olefin of the formula XVI which is obtainable in so doing is optionally reacted in situ with the oxidising agent, for example peracetic acid or michloroperbenzoic acid. The removal of the protecting groups $Z_1$ and $Z_2$ and the introduction of the groups $R_1$-A- and $R_6$ is described hereinbefore under process (a).

Compounds of the formula VIII are manufactured, for example, by reacting an acrylic acid of the formula

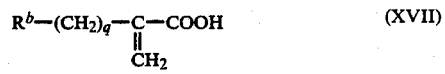

or a suitable functional derivative thereof, with a compound of the formula

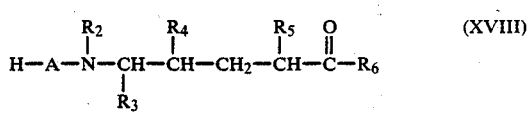

according to process (a). The compound of the formula XVIII is likewise manufactured according to process (a) from an amino acid of the formula H-A-OH, protected at the amino group, and a compound of the formula X and by subsequent removal of the protecting group, optionally before or after the introduction of the radicals $R_2$ and $R_4$.

The following Examples serve to illustrate the invention but do not limit the scope thereof in any way.

Temperatures are given in degrees Celsius. The $R_f$ values are determined on silica gel thin-layer plates in the following solvent systems:

| | | |
|---|---|---|
| A | ethyl acetate/n-hexane | 1:1 |
| B | ethyl acetate/n-hexane | 1:2 |
| C | ethyl acetate/n-hexane | 1:4 |
| D | ethyl acetate/n-hexane | 1:5 |
| E | ethyl acetate/n-hexane | 1:6 |
| F | ethyl acetate/n-hexane | 1:9 |
| G | ethyl acetate/n-hexane | 1:19 |
| H | methylene chloride/methanol | 19:1 |
| I | methylene chloride/methanol | 9:1 |
| J | methylene chloride/methanol | 4:1 |
| K | methylene chloride/methanol/water | 300:10:1 |
| L | methylene chloride/ether | 4:1 |
| M | methylene chloride/methanol/conc. ammonia | 400:10:1 |
| N | methylene chloride/methanol/conc. ammonia | 200:10:1 |
| O | methylene chloride/methanol/conc. ammonia | 100:10:1 |
| P | methylene chloride/methanol/conc. ammonia | 90:10:1 |
| Q | methylene chloride/methanol/conc. ammonia | 80:10:1 |
| R | methylene chloride/methanol/conc. ammonia | 40:10:1 |
| S | methylene chloride/methanol/conc. ammonia | 1000:50:1 |
| T | methylene chloride/methanol/conc. ammonia | 850:50:1 |
| U | methylene chloride/methanol/conc. ammonia | 700:50:1 |
| V | methylene chloride/methanol/conc. ammonia | 500:50:1 |
| W | methylene chloride/methanol/conc. ammonia | 350:50:1 |
| X | methylene chloride/methanol/conc. ammonia | 300:50:1 |
| Y | methylene chloride/methanol/water/-glacial acetic acid | 150:54:10:1 |
| Z | methylene chloride/methanol/conc. ammonia | 300:10:1 |
| AA | methylene chloride/methanol/conc. ammonia | 65:10:1 |
| BB | methylene chloride/methanol/conc. ammonia | 60:10:1 |
| CC | methylene chloride/methanol/conc. ammonia | 50:10:1 |
| DD | methylene chloride/methanol/water | 5:3:1 |
| EE | methylene chloride/methanol/water | 14:6:1 |

For example, the abbreviation "$R_f(A)$" denotes that the $R_f$ value has been determined in system A. The ratio of the solvents to one another is given in parts by volume.

The same abbreviations are used for the eluant systems in the flash chromatography and the medium-pressure chromatography.

Abbreviations for amino acids and amino acid derivatives:

| | |
|---|---|
| H—Ala—OH | L—alanine |
| H—Cha—OH | L—cyclohexylalanine |
| H—Gly—OH | glycine |
| H—His—OH | L—histidine |
| H—Ser—OH | L—serine |
| H—Val—OH | L—valine |

The values for proton nuclear magnetic resonance spectroscopy ($^1$H-NMR) are given in ppm (parts per million) with reference to tetramethylsilane as the internal standard. s=singlet, d=doublet, t=triplet, q=quartet, m=multiplet, dxd=double doublet. m/e=molecular ion of the designated mass in mass spectrometry.

The fragment referred to as

-Cha$^c$Val-denotes the bivalent radical of (2S,4S,5S)-5-amino-6-cyclohexyl-4-hydroxy-2-isopropylhexanoic acid and has the formula

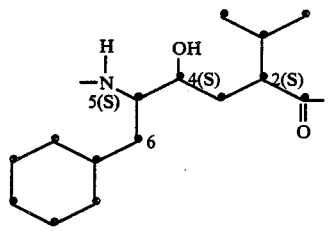

The fragment referred to as

-Leu$^{cx}$Valis derived from the fragment

-Cha$^c$Valby bridging NH and OH by an isopropylidene group and has the formula

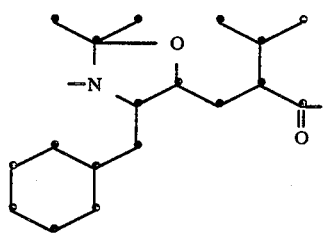

The fragment referred to as

Gly(R$_3$)$^c$Gly(R$_5$)

represents the bivalent residue of 2-R$_5$-4-(S)-hydroxy-5-amino-5-R$_3$-pentanoic acid having the (R)- or (S)-configuration at the C-atom 2 or 5 and has the formula

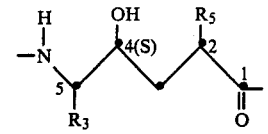

The fragment referred to as

-Gly(R$_3$)$^{cx}$Gly(R$_5$)- is derived from the fragment

-Gly(R$_3$)$^c$Gly(R$_5$)- by bridging NH and OH by an isopropylidene group. The fragment referred to as

-(S)-Gly(R$_3$)$^c$Valaccordingly represents the bivalent residue of 2(S)-isopropyl-4(S)-hydroxy-5(S)-amino-5-R$_3$-pentanoic acid.

| Other abbreviations: |
|---|
| abs. = absolute (anhydrous) |
| Ac = acetyl |
| BOC = tert.-butoxycarbonyl |
| DCCI = dicyclohexylcarbodiimide |
| DCU = dicyclohexylurea |
| DMF = dimethylformamide |
| DMSO = dimethyl sulphoxide |
| HOBt = 1-hydroxybenzotriazole |
| b.p. = boiling point |
| m.p. = melting point |
| THF = tetrahydrofuran |
| Z = benzyloxycarbonyl |

EXAMPLE 1

N-(2(R,S)-benzyl-3-tert.-butylsulphonyl-propionyl)-His-Cha$^c$Val-n-methylamide

A mixture of 50 mg of

H-His-Cha$^c$Val-methylamide, 37 mg of 2-benzyl-3-tert.-butylsulphonyl-propionic acid, 20 mg of HOBt, 32 mg of DCCI and 3 ml of DMF is stirred at room temperature for 50 hours. The crystallised DCU is filtered off and the filtrate is concentrated by evaporation. The crude product is purified by medium-pressure chromatography (1 Lobar ® column size B, eluant N). The fractions containing the title compound are combined and lyophilised from tert.-butanol. $R_f(Q)$=0.26 and 0.30 (2 diastereoisomers).

The starting materials are manufactured in the following manner:

(a) to (k)

H-His-Cha-Val-methylamide (a) 2(S)-benzyloxycarbonylamino-3-cyclohexyl-propionic acid ethyl ester:

243 g of 2(S)-benzyloxycarbonylamino-3-cyclohexyl-propionic acid (manufacture: Helvetica Chimica Acta 57, 2131(1974)) are placed in 600 ml of toluene and 900 ml of ethanol. The reaction mixture is cooled to 0° and 88.3 g of thionyl chloride are added dropwise within 30 minutes. The cooling is removed and the mixture is stirred for 18 hours. The reaction mixture is filtered and the filtrate is concentrated. The residue is separated by means of flash chromatography (2 kg of silica gel 60, 40–63 μm, eluant F). The product-containing fractions are combined, concentrated by evaporation and dried under a high vacuum. The title compound is obtained in the form of a slightly yellowish oil. $R_f(F)=0.2$; $R_f(B)=0.52$.

(b) 2(S)-benzyloxycarbonylamino-3-cyclohexyl-propanal:

116.1 g of 2(S)-benzyloxycarbonylamino-3-cyclohexyl-propionic acid ethyl ester are placed in 2.2 liters of toluene and cooled to −65°. 836 ml of diisobutylaluminium hydride are added dropwise at −65° within 30 minutes and the mixture is then stirred for 20 minutes. Then 84.2 ml of methanol are added dropwise within 10 minutes at −65° and subsequently 825 ml of aqueous potassium sodium tartrate solution without cooling. The reaction mixture is discharged onto 3 liters of potassim sodium tartrate solution/ice and extracted with 5 liters of ether. The ether phase is washed with 2 liters of water, then immediately poured into a solution consisting of 106 g of semicarbazide hydrochloride and 156.5 g of sodium acetate in 620 ml of water and 620 ml of ethanol. The reaction mixture is then stirred at room temperature for 1 hour and subsequently separated in a separating funnel, and the aqueous phase is extracted with 2×1.5 liters of ether. The organic phase is dried over magnesium sulphate and concentrated by evaporation. The crude product is purified by means of flash chromatography (2 kg of silica gel 60, 40–63 μm, eluant A). Concentration by evaporation of the combined product-containing fractions yields the semicarbazone of the title compound, $R_f(I)=0.51$. 130 g of this semicarbazone are dissolved in 1 liter of THF, and 282 ml of 37% formaldehyde solution and then, at 10°, 143 ml of 0.5N HCl are added thereto. The reaction mixture is stirred at room temperature for 2 hours and is filtered, and the filtrate is washed with 0.5 liter of water, 0.5 liter of NaHCO₃ and 0.5 liter of water. The aqueous phases are extracted with 600 ml of ether. The ether phases are dried over magnesium sulphate and concentrated by evaporation. 100 ml of toluene are added to the residue and the whole is concentrated by evaporation to yield the title compound. The latter is further processed immediately.

(c) (1(S)-benzyloxycarbonylamino-2-cyclohexyl-ethyl)oxirane:

18.9 g of sodium hydride dispersion (55% in oil) are freed of oil in a dry reaction flask under argon by stirring three times in 50 ml of petroleum ether (b.p. 40°–60°) and subsequently decanting off the solvent each time. After drying under a high vacuum, a grey powder is obtained which is placed in 500 ml of THF; 55.6 g of trimethylsulphoxonium iodide are added thereto, the temperature increasing to approximately 40°. The grey suspension is boiled under reflux for 1 hour and then, within a period of 50 minutes at −70°, a solution of 108.6 g of 2(S)-benzyloxycarbonylamino-3-cyclohexylpropanal in 250 ml of THF is added. The yellow suspension is stirred at 0° for 2 hours. The yellowish turbid solution is poured onto 500 g of ice. The aqueous solution is extracted with 2.5 liters of ether, and the organic phase is washed with water and, after being dried over sodium sulphate, concentrated by evaporation. The oily residue is separated by means of flash chromatography (2.5 kg of silica gel 60, 40–63 μm, eluant C). The product-containing fractions are combined, concentrated by evaporation and dried under a high vacuum. The title compound (diastereoisomeric mixture, approximately 4:1) is obtained in the form of a slightly yellowish oil. $R_f(K)=0.71$; $R_f(C)=0.16$.

(d) 3(S)-benzyloxycarbonylamino-4-cyclohexyl-1-iodobutane-2(R,S)-ol:

42.3 g of (1(S)- benzyloxycarbonylamino-2-cyclohexylethyl)-oxirane are taken up in 200 ml of acetonitrile and the resulting solution is cooled to 0°. After the addition of 20.9 g of sodium iodide, there are added dropwise at 0°, over a period of 30 minutes, 17.7 ml of trimethylchlorosilane. The mixture is stirred at 0°–3° for 40 minutes and then poured onto 700 ml of ice-cold water. The aqueous mixture is extracted with ether, and the organic phase is washed with 750 ml of 5% aqueous sodium thiosulphate solution and 750 ml of saturated, aqueous sodium chloride solution. After drying over sodium sulphate and concentrating by evaporation, an oily mixture of the title compound is obtained which is further processed directly.

(e) 3-benzyloxycarbonyl-4(S)-cyclohexylmethyl-2,2-dimethyl-5(R)-iodomethyl-1,3-oxazolidine:

49.3 g of the compound of Example (1d) and 1.07 g of p-toluenesulphonic acid monohydrate are stirred in 140 ml of 2,2-dimethoxypropane and 450 ml of methylene chloride for 3 hours at room temperature. The mixture is extracted by shaking between 1 liter of methylene chloride and 500 ml of saturated aqueous sodium bicarbonate solution. The organic phase is washed with water, dried over sodium sulphate and concentrated by evaporation. The crude product is purified by means of flash chromatography (3 kg of silica gel 60, 43–60 μm, eluant E). Concentration by evaporation of the combined product-containing fractions yields the title compound in the form of a slightly yellowish oil. $R_f(C)=0.55$; $R_f(E)=0.46$.

(f) 2(R,S)-(3-benzyloxycarbonyl-4(S)-cyclohexylmethyl-2,2-dimethyl-1,3-oxazolidinyl-5(S)-methyl)-3-methylbutyric acid methyl ester:

14.3 ml of diisopropylamine are dissolved under argon in 200 ml of absolute tetrahydrofuran and cooled to 0°. Then, at 0°–5°, 65.8 ml of a 1.6M solution of n-butyllithium in hexane are added dropwise to the mixture over a period of 20 minutes and the whole is stirred for 20 minutes. Then, at from −70° to −75°, 13.3 ml of isovaleric acid methyl ester are added dropwise and the mixture is stirred for 1.5 hours at −75°. At from −60° to −75°, 320 ml of hexamethylphosphoric acid triamide are added dropwise whole stirring. The resulting suspension is stirred for 10 minutes and, finally, at from −70° to −75°, a solution of 43.4 g of the compound of Example (1e) in 110 ml of tetrahydrofuran is added dropwise in 5 minutes. The reaction mixture is stirred at room temperature for 2.5 hours and finally poured onto a mixture of 1 liter of saturated aqueous ammonium chloride solution and 500 g of ice. The aqueous phase is extracted with 2 liters of ethyl acetate, and the organic phase is washed with water and dried over sodium sulphate. After concentration by evaporation, the diastereoisomeric mixture of the title compound is obtained in the form of a yellow oil. $R_f(C)=0.36$; $R_f(F)=0.21$ (values for the less polar component).

(g) 2(R,S)-(3-benzyloxycarbonyl-4(S)-cyclohexylmethyl-2,2-dimethyl-1,3-oxazolidinyl-5(S)-methyl)-3-methylbutyric acid:

1.77 ml of water are added at approximately 5° to 16.5 g of potassium tert.-butoxide in 250 ml of ether. The white suspension is stirred in an ice bath for a further 10 minutes and then 35.8 g of the compound of Example 1f) (diastereoisomeric mixture) in 250 ml of ether are added thereto, the temperature being maintained below 10°. The reaction mixture is then stirred at room temperature for 18 hours and finally poured onto 500 ml of saturated aqueous ammonium chloride solution. The aqueous phase is extracted with ethyl acetate and the organic phase is washed with saturated aqueous sodium chloride solution, dried over sodium sulphate and concentrated by evaporation. The oily crude product is separated by flash chromatography (2.5 kg of silica gel 60, 40–63 μm, eluant C).

Z-Cha$^{\alpha}$Val-OH;

the less polar component of the title compound having the desired configuration of the carbon atom bonded to the isopropyl group (S-configuration), is obtained in the form of a yellow oil. $R_f(K)=0.20$; $R_f(L)=0.35$.

(h)

Z-Cha$^{\alpha}$Val-methylamide:

A mixture of 311.9 mg of

Z-Cha$^c$Val-methylamide 6.4 ml of DMF, 138.2 mg of HOBt and 186.1 mg of DCCI is left to stand at 0° for 24 hours. An excess of methylamine is added to the mixture and the whole is stirred for 2 hours at 0° and for 2 hours at room temperature. The crystallised DCU is filtered off, and the filtrate is concentrated and dried under a high vacuum. Flash chromatography (eluant system A) of the residue yields the title compound in the form of a colourless oil. $R_f(A)=0.45$.

(i)

H-Cha$^c$Val-methylamide:

243 mg of

Z-Cha$^{\alpha}$Val-methylamide are hydrogenated under normal pressure and at room temperature in 10 ml of methanol/water 9:1 in the presence of 50 mg of palladum-on-carbon (10% Pd) until saturation is reached. The reaction mixture is filtered and the filtrate is stirred with 10 ml of water at room temperature. After evaporating off the solvent, the title compound is obtained in the form of a colourless oil. $R_f(W)=0.11$; $R_f(Y)=0.31$.

(j)

Z-His-Cha$^c$Val-methylamide:

A mixture of 150.8 mg of

H-Cha$^c$Val-methylamide, 6 ml of DMF, 81.1 mg of HOBt, 153.3 mg of Z-His-OH and 144.2 mg of DCCI is stirred for 48 hours at room temperature. The DCU is filtered off, and the filtrate is concentrated and dried under a high vacuum. The residue is separated by flash chromatography (145 g of 1-silica gel 60, 40–63 μm, eluant U). Concencentration by evaporation of the combined product-containing fractions yields the title compound. $R_f(W)=0.35$; $R_f(Y)=0.65$.

(k)

H-His-Cha$^c$Val-methylamide:

130 mg of

H-His-Cha$^c$Val-methylamide:

are hydrogenated under normal pressure at room temperature in 5 ml of methanol/water 9:1 in the presence of 20 mg of palladium-on-carbon (10% Pd) until saturation is reached. The reaction mixture is filtered and the filtrate is stirred with 5 ml of water at room temperature. After evaporating off the solvent, the title compound is obtained in the form of a colourless oil. $R_f(R)=0.38$.

(l) to (o) 2-benzyl-3-tert.-butylsulphonyl-propionic acid (l) α-benzylacrylic acid ethyl ester:

4.0 g of KOH in 50 ml of ethanol are added at room temperature to 20 g of benzylmalonic acid diethyl ester in 40 ml of ethanol and the whole is stirred overnight at room temperature, concentrated by evaporation, 7.1 ml of water are added and the whole is acidified in an ice bath with 6.3 ml of concentrated hydrochloric acid. Partitioning between water and ether is carried out, and the organic phase is dried and the ether is distilled off. 12.9 ml of pyridine, 0.61 g of piperidine and 1.78 g of paraformaldehyde are added to the residue. The mixture is heated in an oil bath (130°) for 90 minutes, cooled, 220 ml of water are added and extraction is carried out 3 times with 75 ml of n-hexane. The combined organic phases are washed with water, 1N HCl, water, saturated NaHCO$_3$ solution and brine. The title compound is obtained by distillation. $^1$H-NMR (DMSO-d$_6$): 1.2 ppm (t, 3H); 3.6 (d, 2H); 4.1 (q, 2H); 5.6 (m, 1H); 6.15 (m, 1H); 7.25 (m, 5H).

(m) 2-benzyl-3-tert.-butylthio-propionic acid ethyl ester:

4.0 g of α-benzylacrylic acid ethyl ester are dissolved in 40 ml of THF and reacted at room temperature with 2.39 ml of tert.-butylmercaptan and 459 mg of sodium hydride dispersion (55% in oil). The mixture is stirred at room temperature for 5 hours, poured onto 1N hydrochloric acid and extracted with ethyl acetate. The extracts are dried and concentrated by evaporation. The residue is purified by flash chromatography on 200 g of silica gel 60 (eluant G). Colourless oil, $^1$H-NMR (DMSO-d$_6$): 1.1 ppm (t, 3H); 1.2 (s, 9H), 2.4–3.0 (m, 5H); 4.05 (q, 2H); 7.2 (s, 5H).

(n) 2-benzyl-3-tert.-butylsulphonyl-propionic acid ethyl ester:

0.5 g of 2-benzyl-3-tert.-butylthio-propionic acid ethyl ester is dissolved in 8 ml of methanol and, while cooling with ice, 1.63 g of oxone ® (potassium peroxomonosulphate, 50% KHSO$_5$, Ventron GmbH, Karlsruhe) in 7 ml of water are added and the whole is stirred overnight at room temperature. The solution is diluted with water and extracted with methylene chloride, and the extracts are dried and concentrated by evaporation. $^1$H-NMR (DMSO-d$_6$): 1.0 ppm (t, 3H), 1.3 (s, 9H); 2.8–3.5 (m, 5H), 3.95 (q, 2H); 7.15–7.3 (m, 5H).

(o) 2-benzyl-3-tert.-butylsulphonyl-propionic acid:

550 mg of 2-benzyl-3-tert.-butylsulphonyl-propionic acid ethyl ester are dissolved in 8 ml of THF and then reacted with 5 ml of water and 0.88 ml of 2N potassium hydroxide solution. The mixture is stirred overnight at room temperature, neutralised with 0.88 ml of 2N hydrochloric acid and concentrated by evaporation. The residue is purified by flash chromatography on 30 g of silica gel 60 (eluant H). Yellow oil; m/e 284; $^1$H-NMR (DMSO-d$_6$): 1.27 ppm (s, 9H); 2.73–3.1 (m, 4H); 3.2–3.5 (m, 1H); 7.2–7.4 (m, 5H); 12.5 (s, 1H).

EXAMPLE 2

N-(2(R,S)-benzyl-3-tert.-butylsulphonyl-propionyl)-His-Cha$^c$Val-n-butylamide

Analogously to Example 1, the title compound is manufactured from 50 mg of

H-His-Cha$^c$Val-butylamide, 34 mg of 2-benxyl-3-tert.-butylsulphonylpropionic acid, 18 mg of HOBt and 29 mg of DCCI and is purified by flash chromatography on 30 g of silica gel 60 (eluant M). R$_f$(O)=0.30 and 0.35 (2 diastereoisomers).

The starting material is manufactured in the following manner:

(a)

H-His-Cha$^c$Val-n-butylamide is obtained by hydrogenating 1.6 g of

Z-His-Cha$^c$Val-n-butylamide in the presence of 200 mg of palladium-on-carbon (10%) analogously to Example 1(k). R$_f$(W)=0.05; R$_f$(Y)=0.16.

(b)

H-His-Cha$^c$Val-n-butylamide is obtained from 1.75 g of Z-H is —OH, 1,97 g of

H-Cha$^c$Val-n-butylamide, 930 mg of HOBt and 1.62 g of DCCI analogously to Example 1j) and is purified by flash chromatography with solvent system W. M.p. 208°–210°. R$_f$(W)=0.49; R$_f$(Y)=0.62.

(c)

H-Cha$^c$Val-n-butylamide is obtained by hydrogenating 4.2 g of

Z-His-Cha$^{cx}$Val-n-butylamide in the presence of 500 mg of palladium-on-carbon (10%) analogously to Example 1(i). R$_f$(W)=0.25.

(d)

Z-His-Cha$^{cx}$Val-n-butylamide is obtained from 4.01 g of

Z-His-Cha$^{cx}$Val-n-OH, 2.68 g of n-butylamine, 1.80 g of HOBt and 2.41 g of DCCI analogously to Example 1(h) and is purified by flash chromatography with solvent system C. R$_f$(A)=0.61.

EXAMPLE 3

N-(2(R,S)-benzyl-3-tert.-butylsulphinyl-propionyl)-His-Cha$^c$Val-n-butylamide

Analogously to Example 1, the title compound is obtained from 50 mg of

H-His-Cha$^c$Val-butylamide, 32 mg of 2-benzyl-3-tert.-butylsulphinyl-propionic acid, 18 mg of HOBt and 29 mg of DCCI and purified by medium-pressure chromatography (1 lobar ® column size B, eluant N). R$_f$(Q)=0.35 and 0.425 (at least 2 of 4 possible diastereoisomers).

The starting material is manufactured in the following manner:

(a) 2-benzyl-3-tert.-butylsulphinyl-propionic acid:

3.2 g of 2-benzyl-3-tert.-butylsulphinyl-propionic acid ethyl ester are dissolved in 30 ml of methanol, and 30 ml of water and 10.8 ml of 1N sodium hydroxide solution are added thereto. The mixture is stirred at room temperature for 16 hours, neutralised with 10.8 ml of 1N hydrochloric acid and concentrated in vacuo. The residue is purified by flash chromatography on 150 g of silica gel 60 (eluant J). R$_f$(J)=0.38.

(b) 2-benzyl-3-tert.-butylsulphinyl-propionic acid ethyl ester:

A solution of 3.67 mg of m-chloroperbenzoic acid in 40 ml of methylene chloride is added at −78° to 4.48 g of 2-benzyl-3-tert.-butylthio-propionic acid ethyl ester. The reaction solution is stirred for 2 hours at −78° and for 17 hours at room temperature, then washed with aqueous NaHCO$_3$ solution and water, dried and concentrated in vacuo. The residue is purified by flash chromatography on 150 g of silica gel 60 (eluant A). $^1$H-NMR (DMSO-d$_6$): 1.0–1.2 ppm (m, 15H); 2.6–3.2 (m, 5H); 4.0 (m, 2H); 7.2–7.4 (m, 5H) (2 diastereoisomers).

EXAMPLE 4

N-(2(R,S)-benzyl-3-tert.-butylthio-
propionyl)-His-Cha$^c$Val-n-butylamide

Analogously to Example 1, the title compound is manufactured from 50 mg of

H-His-Cha$^c$Val-n-butylamide, 30 mg of 2-benzyl-3-tert.-butylthio-propionic acid, 18 mg of HOBt and 29 mg of DCCI and is purified by flash chromatography on 30 g of silica gel 60 (eluant M). $R_f(O)=0.36$.

The starting material is manufactured in the following manner:

(a) 2-benzyl-3-tert.-butylthio-propionic acid:

0.5 g of 2-benzyl-3-tert.-butylthio-propionic acid ethyl ester is dissolved in 5 ml of THF, and 3.2 ml of water and 0.9 ml of 2N potassium hydroxide solution are added thereto. The mixture is stirred overnight at room temperature, neutralised with 0.9 ml of 2N hydrochloric acid and concentrated by evaporation. The residue is purified by flash chromatography on 30 g of silica gel 60 (eluant H). Yellow oil, $^1$H-NMR (DMSO-$d_6$): 1.23 ppm (s, 9H); 2.55–2.9 (m, 5H); 7.15–7.3 (m, 5H); 12.4 (s, 1H).

EXAMPLE 5

N-(2(R,S)-benzyl-3-methylsulphonyl-
propionyl)-His-Cha$^c$Val-n-methylamide

Analogously to Example 1, the title compound is manufactured from 50 mg of

H-His-Cha$^c$Val-methylamide, 32 mg of 2-benzyl-3-methylsulphonyl-propionic acid, 20 mg of HOBt and 32 mg of DCCI and purified by medium-pressure chromatography (1 Lobar ® column size B, eluant P). $R_f(Q)=0.14$ and 0.23 (2 diastereoisomers).

The starting material is manufactured in the following manner:

(a) 2-benzyl-3-methylsulphonyl-propionic acid:

1.74 g of 2-benzyl-3-methylsulphonyl-propionic acid ethyl ester in 35 ml of 4N hydrochloric acid are heated under reflux for 2 hours. The cooled solution is extracted with ethyl acetate, the extracts are dried and concentrated and the residue is purified by medium pressure chromatography (1 Lobar ® column size B, eluant A). $^1$H-NMR (DMSO-$d_6$): 2.95 ppm (s, 3H); 2.8–3.8 (m, 5H); 7.2 (s, 5H).

(b) 2-benzyl-3-methylsulphonyl-propionic acid ethyl ester:

2.198 g of 2-benzyl-3-methylthio-propionic acid ethyl ester are dissolved in 20 ml of methanol and, in an ice bath, 8.4 g of oxone ® (potassium peroxomonosulphate, 50% KHSO$_5$, Ventron) in 35 ml of water are added thereto and the whole is stirred overnight at room temperature. The mixture is diluted with water and extracted with ethyl acetate, the extracts are dried and concentrated by evaporation and the residue is purified by medium-pressure chromatography (1 Lobar ® column size B, eluant C). $^1$H-NMR (DMSO-$d_6$): 1.0 ppm (t, 3H); 3.0 (s, 3H), 3.05–3.6 (m, 5H); 4.0 (q, 2H); 7.2 (s, 5H).

(c) 2-benzyl-3-methylthio-propionic acid ethyl ester:

2.0 g of α-benzylacrylic acid ethyl ester are dissolved in 20 ml of ethanol and, in an ice bath, 1.474 g of sodium thiomethoxide are added thereto and the whole is stirred for 45 minutes at 0° C. The reaction mixture is poured into a solution of 18 g of sodium dihydrogen phosphate in water and extracted with ether. The extracts are dried and concentrated by evaporation to yield the title compound. $^1$H-NMR (DMSO-$d_6$): 1.65 ppm (t, 3H); 2.1 (s, 3H); 2.4–3.0 (m, 5H); 4.0 (q, 2H); 7.2 (s, 5H).

EXAMPLE 6

N-(2(R,S)-benzyl-3-tert.-methylsulphonyl-
propionyl)-His-Cha$^c$Val-n-butylamide Analogously to Example 1, the title compound is manufactured from 50 mg of H-His-Cha$^c$Val-butylamide, 29 mg of 2-benzyl-3-methylsulphonylpropionic acid, 18 mg of HOBt and 29 mg of DCCI and purified by medium-pressure chromatography (1 Lobar ® column size B, eluant N). $R_f(Q)=0.37$ and 0.44 (2 diastereoisomers).

EXAMPLE 7

N-(2(R)- and 2(S)-methylsulphonyl-4-phenyl-
butyryl)-His-Cha$^c$Val-n-butylamide Analogously to Example 1, the title compounds are manufactured from 46 mg of H-His-Cha$^c$Val-butylamide, 46 mg of 2-methylsulphonyl-4-phenylbutyric acid dicyclohexylammonium salt, 17 mg of HOBt and 27 mg of DCCI and are separated by flash chromatography on 110 g of silica gel 60 (eluant T). Diastereoisomer I: $R_f(V)=0.23$. Diastereoisomer II: $R_f(V)=0.125$.

The starting material is manufactured in the following manner:

(a) 2-methylsulphonyl-4-phenylbutyric acid dicyclohexylammonium salt:

2.09 g of 2-methylsulphonyl-4-phenylbutyric acid ethyl ester are dissolved at room temperature in 11.59 ml of 1N sodium hydroxide solution and 11.59 ml of ethanol and the whole is stirred overnight. The solution is neutralised with 11.59 ml of 1N hydrochloric acid, concentrated by evaporation, taken up in a small amount of acetonitrile and boiled up, and then filtered. 1.54 ml of dicyclohexylamine are added to the filtrate, and the crystalline product is filtered off and recrystallised from acetonitrile/diisopropyl ether. M.p. 184°–185°.

(b) 2-methylsulphonyl-4-phenylbutyric acid ethyl ester:

6.648 g of methylsulphonyl-acetic acid ethyl ester are added dropwise at −30°, within 30 minutes, to 1.745 g of sodium hydride dispersion (55% in oil) in 40 ml of DMF. The solution is subsequently stirred for 15 minutes, then heated and, within 150 minutes, under reflux, 7.4 g of 2-phenylethyl bromide in 10 ml of DMF are added dropwise thereto. The reaction mixture is then stirred for 20 minutes, acidified with 12 ml of glacial acetic acid and concentrated by evaporation. The residue is taken up in ethyl acetate, washed with water, dried over magnesium sulphate, concentrated by evaporation and purified by flash chromatography on 700 g of silica gel 60 (eluant D). $^1$H-NMR (DMSO-d$_6$): 1.35 ppm (t, 3H), 2.6–2.9 (m, 2H); 3.75 (dxd, 1H); 4.25 (q, 2H).

EXAMPLE 8

N-(2(R,S)-methylsulphonyl-3-phenyl-propionyl)-His-Cha$^c$Val-n-butylamide

Analogously to Example 1, the title compound is manufactured from 46 mg of

H-His-Cha$^c$Val-butylamide, 45 mg of 2-methylsulphonyl-3-phenylpropionic acid dicyclohexylammonium salt, 17 mg of HOBt and 27 mg of DCCI and is purified by flash chromatography on 50 g of silica gel 60 (eluant U). R$_f$(X)=0.46.

The starting material is manufactured in the following manner:
(a) 2-methylsulphonyl-3-phenylpropionic acid dicyclohexylammonium salt:

3.6 g of 2-methylsulphonyl-3-phenylpropionic acid ethyl ester are stirred overnight at room temperature in 21 ml of ethanol and 21 ml of 1N sodium hydroxide solution. The solidified reaction mixture is neutralised with 21 ml of 1N hydrochloric acid, concentrated by evaporation, boiled up in acetonitrile and filtered. 2.8 ml of dicyclohexylamine are added to the filtrate, and the crystalline product is filtered off and recrystallised from acetonitrile/diisopropyl ether. M.p. 187°–188°.

(b) 2-methylsulphonyl-3-phenylpropionic acid ethyl ester:

6.648 g of methylsulphonyl-acetic acid ethyl ester in 20 ml of DMF are added dropwise at −25°, within 25 minutes, to 1.745 g of sodium hydride dispersion (55% in oil) in 40 ml of DMF. The solution is subsequently stirred for 30 minutes at −25°, then 6.84 g of benzyl bromide in 40 ml of DMF are added dropwise. The reaction mixture is then stirred for 1 hour at room temperature, acidified with 12 ml of glacial acetic acid, left to stand overnight and concentrated by evaporation. The residue is taken up in ethyl acetate, washed with water, dried, concentrated by evaporation and purified by flash chromatography on 700 g of silica gel 60 (eluant E). $^1$H-NMR (DMSO-d$_6$): 1.1 ppm (t, 3H); 3.05 (s, 3H); 3.1–3.6 (m, 2H); 3.9–4.3 (m, 3H); 7.25 (m, 5H).

EXAMPLE 9

N-(2(S)-benzyl-3-tert.-methylsulphonyl-propionyl)-His-Cha$^c$Val-n-butylamide

Analogously to Example 2, the title compound is manufactured from 50 mg of

H-His-Cha$^c$Val-butylamide, 34 mg of 2(S)-benzyl-3-tert.-butylsulphonylpropionic acid, 18 mg of HOBt and 29 mg of DCCI and purified by flash chromatography on 30 g of silica gel 60 (eluant M). R$_f$(N)=0.09; R$_f$(Y)=0.57; R$_f$(O)=0.35.

The starting material is manufactured in the following manner:
(a) 2(S)-benzyl-3-tert.-butylsulphonyl-propionic acid:

5.00 g of 2(S)-benzyl-3-tert.-butylsulphonylpropionic acid 1'(S)-benzyl-2'-hydroxy-ethylamide are maintained at 90° for 5 hours in 25 ml of glacial acetic acid and 75 ml of 6N HCl. The reaction mixture is concentrated and extracted with methylene chloride. The organic phase is washed with 1N HCl, concentrated and chromatographed on silica gel with eluant M. The pure title compound is recrystallised from ethyl acetate/hexane. M.p. 99°–101°. R$_f$(A)=0.16; [α]$_D^{22}$=10.9° (c=0.91 in CH$_2$Cl$_2$); 1H-NMR and TLC elution behaviour identical with compound of Example 1o).

The pure title compound can be obtained also by fractional crystallisation of the (+)-dehydroabietylammonium salts of the racemic acid in isopropanol and splitting of the diastereoisomerically pure crystalline product.

(b) 2(R)- and 2(S)-benzyl-3-tert.-butylsulphonylpropionic acid 1'(S)-benzyl-2'-hydroxy-ethylamide Analogously to Example 1, the amides are manufactured from 12.5 g of racemic 2-benzyl-3-tert.-butylsulphonyl-propionic acid (Example 1o)), 7.32 g of 2(S)-amino-3-phenyl-propanol (L-phenylalaninol), 7.41 g of HOBt and 11.80 g of DCCI in 400 ml of DMF. The crystallised DCU is filtered off, the filtrate is concentrated and the residue is separated by flash chromatography on silica gel with eluant A.

Non-polar 2(S)-amide: R$_f$(C)=0.21; [α]$_D^{22}$=+0.4° (c=1.0 in CH$_3$OH), $^1$H-NMR (DMSO-d$_6$): 1.22 (s, 9H); 2.58–2.67 (m, 1H); 2.75–2.95 (m, 4H); 3.05–3.17 (m, 2H); 3.17–3.35 (m, 2H); 3.85–4.63 (t, 1H, OH); 7.11–7.32 (m, 10H); 7.95 (d, 1H, NH).

Polar 2(R)-amide: R$_f$(C)=0.11; [α]$_D^{22}$=−47.4° (c=1.0 in CH$_3$OH). $^1$H-NMR (DMSO-d$_6$): 1.20 (s, 9H); 2.45–2.58 (m, 2H); 2.62–2.97 (m, 3H); 3.03–3.13 (m, 1H); 3.20–3.31 (m, 1H); 3.35–3.48 (m, 2H); 3.88 (m, 1H); 4.66 (t, 1H, OH); 7.05–7.28 (m, 10H); 8.05 (d, 1H, NH).

EXAMPLE 10

N-(2(R)-benzyl-3-tert.-methylsulphonyl-propionyl)-His-Cha$^c$Val-n-butylamide

Analogously to Example 2, the title compound is manufactured from 50 mg of

H-His-Cha$^c$Val-butylamide, 34 mg of 2(R)-benzyl-3-tert.-butylsulphonylpropionic acid, 18 mg of HOBt and 29 mg of DCCI and purified by flash chromatography on 30 g of silica gel (eluant M). R$_f$(N)=0.11; R$_f$(Y)=0.61; R$_f$(O)=0.30.

The starting material is manufactured in the following manner:
(a) 2(R)-benzyl-3-tert.-butylsulphonyl-propionic acid is obtained analogously to Example 9(a) by hydrolysis of the corresponding (polar) 1'(S)-benzyl-2'-hydroxyethylamide (Example 9(b)). [α]$_D^{22}$=−8.6° (c=1.01 in CH$_3$OH;; $^1$H-NMR and TLC elution behaviour identical with compounds of Examples 9(a) and 1(o).

EXAMPLE 11

N-(2(R,S)-benzyl-3-tert.-isopropylsulphonyl-propionyl)-His-Cha$^c$Val-n-methylamide Analogously to Example 1, the title compound is obtained from 56 mg of 2(R,S)-benzyl-3-isopropylsulphonyl-propionic acid, 80 mg of H-His-Cha$^c$Val-methylamide, 32 mg of HOBt and 51 mg of DCCI and is purified by flash chromatography with eluant N. $R_f(Q)=0.4$ and 0.35 (2 diastereoisomers).

The starting material 2-benzyl-3-isopropyl- sulphonyl-propionic acid is manufactured analogously to Example 1 (m), (n) and (o) from α-benzylacrylic acid ethyl ester and isopropylmercaptan.

EXAMPLE 12

N-(3-ethylsulphonyl-2(R,S)-benzyl-propionyl)-His-Cha$^c$Val-n-methyamide

Analogously to Example 1, the title compound is obtained from 67 mg of 3-ethylsulphonyl-2(R,S)-benzylpropionic acid, 100 mg of H-His-Cha$^c$Val-methylamide, 40 mg of HOBt and 63 mg of DCCI and is purified by flash chromatography with eluant N. $R_f(Q)=0.26$ and 0.20 (2 diastereoisomers).

The starting material 3-ethylsulphonyl-2-benzylpropionic acid is manufactured analogously to Example 1 (m), (n) and (o) from α-benzylacrylic acid ethyl ester and ethylmercaptan.

EXAMPLE 13

N-(2(R,S)-benzyl-3-[2-pyridyl]sulphonyl-propionyl)-His-Cha$^c$Val-n-methylamide

Analogously to Example 1, the title compound is obtained from 41.8 mg of 2(R,S)-benzyl-3-(2-pyridyl)-sulphonyl-propionic acid, 50 mg of H-His-Cha$^c$Val-methylamide, 19.9 mg of HOBt and 31.8 mg of DCCI and is purified by flash chromatography with eluant O. $R_f(R)=0.56$.

The starting material is manufactured in the following manner:

(a) 2-benzyl-3-(2-pyridyl)sulphonyl-propionic acid:

233 mg of 2-benzyl-3-(2-pyridyl)sulphonyl-propionic acid ethyl ester are boiled under reflux for 2 hours in 4 ml of 4N HCl. The reaction mixture is diluted with water and extracted with ethyl acetate. The organic phases are washed with water, dried and concentrated by evaporation. The residue is chromatographed on silica gel with eluant H and yields white crystals of the title compound of $R_f(I)=0.3$.

(b) 2-benzyl-3-(2-pyridyl)sulphonyl-propionic acid ethyl ester:

A solution of 724 mg of oxone ® (potassium peroxomonosulphate, 50% KHSO$_5$, Ventron) in 3.5 ml of water is added at room temperature to a solution of 239 mg of 2-benzyl-3-(2-pyridyl)thio-propionic acid ethyl ester in 2 ml of methanol and the whole is stirred at that temperature for 20 hours. The reaction mixture is subsequently extracted twice with ethyl acetate. The organic phases are washed with water, dried over sodium sulphate and concentrated by evaporation. Chromatography of the residue on silica gel with eluant A yields the title compound in the form of a colourless oil. $R_f(A)=0.57$.

(c) 2-benzyl-3-(2-pyridyl)thio-propionic acid ethyl ester:

106 mg of triethylamine are added at 0°, while stirring, to a solution of 1 g of α-benzylacrylic acid ethyl ester and 643 mg of 2-mercaptopyridine in 5 ml of abs. ethanol. The reaction mixture is stirred at room temperature for 5 days and then concentrated by evaporation in vacuo. Flash chromatography of the residue on silica gel with eluant G yields the title compound in the form of a colourless oil. $R_f(C)=0.44$.

EXAMPLE 14

N-(2(R,S)-benzyl-3-dimethylaminosulphonyl-propionyl)-His-Cha$^c$Val-n-methylamide Analogously to Example 1, the title compound is obtained from 21.8 mg of 2(R,S)-benzyl-3-dimethylaminosulphonyl-propionic acid, 36.3 mg of H-His-Cha$^c$Val-methylamide, 13.1 mg of HOBt and 21 mg of DCCI and is purified by flash chromatography with eluant Z. $R_f(Q)=0.42$.

The starting material is manufactured in the following manner:

(a) 2-benzyl-3-dimethylaminosulphonyl-propionic acid:

A mixture of 299 mg of 2-benzyl-3-dimethylaminosulphonyl-propionic acid ethyl ester, 1 ml of methanol, 2 ml of water and 0.42 ml of 1H NaOH is stirred for 16 hours at room temperature, then neutralised with 0.42 ml of 1N HCl and extracted with ethyl acetate. The organic extracts are washed with water, dried, concentrated by evaporation and purified by chromatography on silica gel with eluant I. $R_f(J)=0.48$.

(b) 2-benzyl-3-dimethylaminosulphonyl-propionic acid ethyl ester:

A solution of 359 mg of 2-benzyl-3-chlorosulphonyl-propionic acid ethyl ester in 2 ml of methylene chloride is cooled to −10° and 0.464 ml of a 5.6M solution of dimethylamine in ethanol is added thereto. The solution is stirred for 15 minutes at −15°, mixed with 2N HCl and extracted with methylene chloride. The extracts are washed with water, dried with magnesium sulphate and concentrated by evaporation. The residue is chromatographed on silica gel with eluant C. $R_f(A)=0.43$.

(c) 2-benzyl-3-chlorosulphonyl-propionic acid ethyl ester:

A stream of chlorine gas is passed into a suspension of 333 mg of 3-acetylthio-2-benzyl-propionic acid ethyl ester in 15 ml of water for 30 minutes at room temperature. The reaction mixture is then flushed with nitrogen and extracted with methylene chloride. The organic phase is washed with brine, dried with magnesium sulphate and concentrated by evaporation. The crude title compound is further processed directly. $R_f(C)=0.36$.

(d) 3-acetylthio-2-benzyl-propionic acid ethyl ester:

A mixture of 576 mg of α-benzylacrylic acid ethyl ester and 0.259 ml of thioacetic acid is stirred for 20 hours at 70° and then concentrated by evaporation in vacuo. The residue is purified by flash chromatography with eluant F. $R_f(C)=0.35$.

EXAMPLE 15

N-(2(R,S)-benzyl-3-diethylaminosulphonyl-propionyl)-His-Cha$^c$Val-n-methylamide Analogously to Example 1, the title compound is obtained from 94 mg of 2(R,S)-benzyl-3-diethylaminosulphonyl-propionic acid, 75 mg of H-His-Cha$^c$Val-methylamide, 49 mg of HOBt and 84 mg of DCCI and is purified by flash chromatography in system Z. $R_f(Q)=0.4$.

The starting material 2-benzyl-3-diethylaminosulphonyl-propionic acid is manufactured analogously to Example 14 (a) and (b).

EXAMPLE 16

N-(2(R,S)-benzyl-3-isopropylaminosulphonyl-propionyl)-His-Cha$^c$Val-n-methylamide Analogously to Example 1, the title compound is obtained from 13 mg of 2(R,S)-benzyl-3-isopropylaminosulphonyl-propionic acid, 21.2 mg of H-His-Cha$^c$Val-methylamide, 7.7 mg of HOBt and 12.2 mg of DCCI and is purified by flash chromatography with eluant O. $R_f(Q)=0.46$ and 0.35 (2 diastereoisomers).

The starting material 2-benzyl-3-isopropylaminosulphonyl-propionic acid is manufactured analogously to Example 14 (a) and (b).

EXAMPLE 17

N-3-phenyl-(2(R,S)-[2-thiazolinylthio-propionyl)-His-Cha$^c$Val-n-methylamide

Analogously to Example 1, the title compound is obtained from 15 mg of 2(R,S)-(2-thiazolinylthio)-hydrocinnamic acid, 23.6 mg of H-His-Cha$^c$Val-methylamide, 8.5 mg of HOBt and 15 mg of DCCI and is purified by flash chromatography with eluant W. $R_f(Q)=0.48$.

The starting material is manufactured in the following manner:

(a) 2-(2-thiazolinylthio)-hydrocinnamic acid:

A mixture of 250 mg of 2-(2-thiazolinylthio)-hydrocinnamic acid ethyl ester, 36 mg of lithium hydroxide monohydrate and 5 ml of THF/water 9:1 is stirred at room temperature for 5 days and then concentrated to dryness by evaporation. The residue is taken up in water, washed with ethyl acetate, adjusted to pH 5 with 0.5N HCl and extracted with ethyl acetate. The extracts are washed with water, dried with sodium sulphate, concentrated by evaporation and chromatographed on silica gel with eluant R. $R_f(R)=0.22$.

(b) 2-(2-thiazolinylthio)-hydrocinnamic acid ethyl ester:

1.4 ml of triethylamine are added dropwise to a solution of 1.8 g of 2-mercapto-1,3-thiazoline and 2.6 g of 2-bromo-hydrocinnamic acid ethyl ester in 15 ml of THF and the whole is stirred under reflux for 6 hours. The reaction mixture is filtered, the filtrate is concentrated by evaporation and the residue is partitioned between ethyl acetate and water. The organic phase is washed with water, dried, concentrated by evaporation and purified by chromatography on silica gel with eluant R. $R_f(W)=0.67$.

EXAMPLE 18

N-(2(R,S)-benzyl-3-tert.-butylsulphonylpropionyl)-His-Cha$^c$Val-2-(4-imidazolyl)-ethylamide Analogously to Example 1, the title compound is obtained from 38.6 mg of 2(R,S)-benzyl-3-tert.-butylsulphonyl-propionic acid, 61.9 mg of H-His-Cha$^c$Val-2-(4-imidazolyl)-ethylamide, 20.8 mg of HOBt and 33.1 mg of DCCI and is purified by flash chromatography with eluant O. $R_f(CC)=0.42$ and 0.32 (2 diastereoisomers).

The starting material is manufactured in the following manner:

(a)

H-His-Cha$^c$Val-2-(4-imidazolyl)-ethylamide:

A mixture of

N$^\alpha$,N$^{Im}$-ditrityl-His-Cha$^c$Val-4-imidazolyl)-ethylamide and 2 ml of trifluoroacetic acid is stirred at room temperature for 30 minutes, concentrated at 40° under a water-jet vacuum, 2 ml of a mixture of methylene chloride/methanol/conc. NH$_3$ 5:3:1 are added thereto and the whole is again concentrated by evaporation in vacuo. The title compound is obtained from the residue by chromatography with eluant CC. $R_f(R)=0.155$.

(b)

N$^\alpha$,N$^{Im}$-ditrityl-His-Cha$^c$Val-4-imidazolyl)-ethylamide

Analogously to Example 1(j), the title compound is obtained from 155 mg of N$^\alpha$,N$^{Im}$-ditrityl-histidine, 63 mg of H-Cha$^c$Val-2-(4-imidazolyl)-ethylamide, 37 mg of HOBt and 57 mg of DCCI and purified by chromatography with eluant N. $R_f(Q)=0.82$.

(c)

H-Cha$^c$Val-2-(4-imidazolyl)-ethylamide:

Analogously to Example 1(i), the title compound is obtained by hydrogenating 103 mg of Z-Cha$^{\alpha x}$Val-2-(4-imidazolyl)-ethylamide with 50 mg of Pd/C in 20 ml of methanol/water 19:1 at room temperature under normal pressure. Colourless oil, $R_f(BB)=0.25$.

(d)

Z-Cha<sup>α</sup>Val-2-(4-imidazolyl)-ethylamide:

Analogously to Example 1h, the title compound is obtained from 100 mg of

Z-Cha<sup>α</sup>Val-OH, 45.4 mg of histamine dihydrochloride, 60 mg of DCCI, 37.8 mg of HOBt and 63.8 mg of diisopropylethylamine and purified by chromatography with eluant AA. $R_f(BB)=0.62$.

EXAMPLE 19

N-(2(R,S)-benzyl-3-tert.-butylsulphonylpropionyl)-His-Cha<sup>c</sup>Val-((S)-5-tert.-butoxycarbonylamino-5-methoxycarbonylpentyl)-amide Analogously to Example 1, the title compound is obtained from 56.9 mg of 2-benzyl-3-tert.-butylsulphonyl-propionic acid, 118.3 of a H-His-Cha<sup>c</sup>Val-(S)-5-tert.-butoxycarbonyl-amino-5-methoxy-carbonyl-pentyl)-amide, 30.6 mg of HOBt and 49.4 mg of DCCI in 3.3 ml of DMF and is purified by flash chromatography with solvent system W. $R_f(X)=0.67$; $R_f(U)=0.09$.

The manufacture of the starting material

H-His-Cha<sup>c</sup>Val-(S)-5-tert.-butoxycarbonyl-amino-5-methoxy-carbonyl-pentyl)-amide is described in European Patent Application No. EP 184 560.

EXAMPLE 20

N-(2(R,S)-benzyl-3-tert.-butylsulphonyl-propionyl)-His-Cha<sup>c</sup>Val-((S)-5-amino-5-carboxy-pentyl)-amide 75.6 mg of N-(2(R,S)-benzyl-3-tert.-butylsulphonyl-propionyl)-His-Cha<sup>c</sup>Val-((S)-5-amino-5-carboxy-pentyl)-amide and 1.25 ml of 0.1N NaOH are stirred in 1.25 ml of methanol for 16 hours at room temperature. The reaction mixture is concentrated by evaporation, 1.5 ml of trifluoroacetic acid are added thereto and the whole is left to stand for 20 minutes at room temperature. The trifluoroacetic acid is evaporated off and the crude product is purified by flash chromatography (90 g of silica gel 40-63 μm, eluant DD). The residue is lyophilised from tert.-butanol to yield the title compound in the form of a white powder. $R_f(DD)=0.70$; $R_f(Y)=0.24$.

EXAMPLE 21

N-(2(S)-benzyl-3-tert.-butylsulphonyl-propionyl)-Ala-Cha<sup>c</sup>Val-n-butylamide Analogously to Example 2, the title compound is manufactured from 105 mg of H-Ala-Cha<sup>c</sup>Val-n-butylamide, 98 mg of 2(S)-benzyl-3-tert.-butylsulphonylpropionic acid (Example 9(a)), 53 mg of HOBt and 82 mg of DCCI and is purified by flash chromatography on 65 g of silica gel (eluant N). $R_f(P)=0.62$.

The starting materials are manufactured in the following manner:

(a)

H-Ala-Cha<sup>c</sup>Val-n-butylamide is obtained by hydrogenating 135 mg of

Z-Ala-Cha<sup>c</sup>Val-n-butylamide in the presence of 50 mg of palladium-on-carbon (10%) analogously to Example 1(k). $R_f(O)=0.33$.

(b)

H-Cha<sup>c</sup>Val-n-butylamide is obtained from 64 mg of Z-Ala-OH, 62 mg of

H-Cha<sup>c</sup>Val-n-butylamide (Example 2(c)), 38 mg of HOBt and 59 mg of DCCI analogously to Example 1(j) and is purified by flash chromatography with solvent system N. $R_f(N)=0.22$.

EXAMPLE 22

N-(2(S)-benzyl-3-tert.-butylsulphonyl-propionyl)-Ala-Cha<sup>c</sup>Val-methylamide Analogously to Example 1, the title compound is manufactured from 90 mg of H-Ala-Cha<sup>c</sup>Val-methylamide, 93 mg of 2(S)-benzyl-3-tert.-butylsulphonylpropionic acid, 46 mg of HOBt and 78 mg of DCCI and is purified by flash chromatography on 30 g of silica gel 60 (eluant N). $R_f(N)=0.19$; $R_f(P)=0.48$.

The starting material is manufactured in the following manner:

(a)

H-Ala-Cha<sup>c</sup>Val-methylamide is obtained by hydrogenating 390 mg of

Z-Ala-Cha<sup>c</sup>Val-methylamide in the presence of 40 mg of palladium-on-carbon (10%) analogously to Example 1(k). $R_f(P)=0.38$; $R_f(N)=0.15$.

(b)

Z-Ala-Cha<sup>c</sup>Val-methylamide, is obtained from 326 mg of Z-Ala-OH, 380 mg of H-Cha<sup>c</sup>Val-methylamide (Example 1(i)), 225 mg of HOBt and 358 mg of DCCI analogously to Example 1(j) and is purified by flash chromatography with solvent system N. R$_f$(N)=0.19.

EXAMPLE 23

N-(2(S)-benzyl-3-tert.-butylsulphonyl-propionyl)-
His-(S)-Gly(2-cyclohexylethyl)<sup>c</sup>Val-n-butylamide A mixture of 76 mg of H-His-(S)-Gly(2-cyclohexylethyl)<sup>c</sup>Val-n-butylamide, 50 mg of 2-(S)-benzyl-3-tert.-butylsulphonyl-propionic acid, 27 mg of HOBt, 43 mg of DCCI and 2.4 ml of DMF is stirred for 8 hours at 0° and then for 12 hours at room temperature. The crystalline DCU is filtered off and the filtrate is concentrated by evaporation. The residue is stirred in a mixture of methanol/water/glacial acetic acid 94:3:3 for 60 minutes at 60° and is then concentrated. The residue is purified by means of flash chromatography (90 g of silica gel Si 60, 40–63 µm, system U). The fractions containing the title compound are combined and lyophilised from tert.-butanol. R$_f$(W)=0.34.

The starting material is manufactured in the following manner:
(a)

H-His-(S)-Gly(2-cyclohexylethyl)<sup>c</sup>Val-n-butylamide is manufactured analogously to Examples 2 (a) to (d) and 1 (a) to (g) from 2(S)-amino-4-cyclohexylbutyric acid. R$_f$(R)=0.58.

(b) 2(S)-amino-4-cyclohexyl-butyric acid:
896 mg of L-homophenylalanine (2(S)-amino-4-phenylbutyric acid) are hydrogenated in 25 ml of water and 5.5 ml of 1N HCl in the presence of 18 mg of Nishimura catalyst (rhodium oxide/platinum oxide). The reaction mixture is filtered while warm. The title compound crystallises out of the filtrate in the form of white crystals after the addition of 5.5 ml of 1N NaOH. M.p. 265°–266°; R$_f$(R)=0.09.

EXAMPLE 24

N-(2(S)-benzyl-3-tert.-butylsulphonyl-propionyl)-
His-(S)-Gly(cyclopentylmethyl)<sup>c</sup>Val-n-butylamide A mixture of 72 mg of H-His-(S)-Gly(cyclopentylmethyl)<sup>c</sup>Val-n-butylamide, 50 mg of 2(S)-benzyl-3-tert.-butylsulphonyl-propionic acid, 27 mg of HOBt, 43 mg DCCI and 2.4 ml of DMF is stirred for 8 hours at 0° and then for 12 hours at room temperature. The crystalline DCU is filtered off and the filtrate is concentrated by evaporation. The residue is stirred in a mixture of methanol/water/glacial acetic acid 94:3:3 for 60 minutes at 60° and is subsequently concentrated. The residue is separated by means of flash chromatography (100 g of silica gel Si 60, 40–63 µm, system U.) The fractions containing the title compound are combined and lyophilised from tert.-butanol. R$_f$(W)=0.31; R$_f$(Y)=0.64.

The starting material is manufactured in the following manner:
(a)

H-His-(S)-Gly(cyclopentylmethyl)<sup>c</sup>Val-n-butylamide is obtained analogously to Examples 2 (a) to (d) and 1 (a) to (g) from 2-amino-3-cyclopentyl-propionic acid (P. R. Pal, Ch. G. Skinner, R. L. Dennis and W. Shive, J. Am. Chem. Soc. 78, 5116 (1956)). R$_f$(R)=0.42.

EXAMPLE 25

N-(2(S)-benzyl-3-tert.-butylsulphonyl-propionyl)-
His-(S)-Gly(cycloheptylmethyl)<sup>c</sup>Val-n-butylamide A mixture of 76 mg of H-His-(S)-Gly(cycloheptylmethyl)<sup>c</sup>Val-n-butylamide, 50 mg of 2(S)-benzyl-3-tert.-butylsulphonyl-propionic acid, 27 mg of HOBt, 43 mg of DCCI and 2.4 ml of DMF is stirred for 8 hours at 0° and then for 12 hours at room temperature. The crystalline DCU is filtered off and the filtrate is concentrated by evaporation. The residue is stirred in a mixture of methanol/water/glacial acetic acid 94:3:3 for 60 minutes at 60° and is subsequently concentrated. The residue is separated by means of flash chromatography (100 g of silica gel Si 60, 43–60 µm, system U). The fractions containing the title compound are combined and lyophilised from tert.-butanol. R$_f$(W)=0.58.

The starting material is manufactured in the following manner:
(a)

H-His-(S)-Gly(cycloheptylmethyl)<sup>c</sup>Val-n-butylamide is manufactured analogously to Examples 2 (a) to (d) and 1 (a) to (g) from 2-amino-3-cycloheptyl-propionic acid, R$_f$(R)=0.60. The amino acid used as starting material can be synthesised analogously to the corresponding cyclopentyl-substituted amino acid and separated into the enantiomers by fractional crystallisation of diastereoisomeric salts or chromatographic separation of diastereoisomeric amides.

EXAMPLE 26

N-(2(S)-benzyl-3-tert.-butylsulphonyl-propionyl)-
His-Cha<sup>c</sup>Gly(SCH$_3$)-n-butylamide Analogously to Example 1, the title compound is manufactured from 140 mg of H-His-Cha<sup>c</sup>Gly(SCH$_3$)-n-butylamide, 128 mg of 2-benzyl-3-tert.-butylsulphonylpropionic acid, 72 mg of HOBt and 92 mg of DCCI and is purified by flash chromatography on 30 g of silica gel 60 (eluant N). R$_f$(I)=0.32 and 0.28 (2 diastereoisomeric pairs).

The starting material is manufactured in the following manner:
(a)

H-His-Cha$^c$Gly(SCH$_3$)-n-butylamide:

A mixture of 132 mg of

H-Cha$^c$Gly(SCH$_3$)-n-butylamide, 260 mg of 1-benzotriazolyloxy-tris(dimethylamino)-phosphonium hexafluorophosphate, 384 mg of N$^\alpha$,N$^{Im}$-ditrityl-histidine, 3 ml of DMF and 0.1 ml of triethylamine is stirred for 14 hours at room temperature. The reaction mixture is concentrated and the residue is purified by flash chromatography (25 g of silica gel 60, eluant A). Subsequently, 3 ml of 90% trifluoroacetic acid are added to the N$^\alpha$,N$^{Im}$-ditrityl-His-Cha$^c$Gly(SCH$_3$)-n-butylamide and the whole is stirred for 30 minutes at room temperature. The reaction mixture is concentrated and the residue is partitioned between aqueous potassium carbonate solution and methylene chloride. The combined organic extracts are washed with brine and dried over sodium sulphate. After concentration by evaporation, a diastereoisomeric mixture of the title compound is obtained in the form of a white foam. $R_f(Y)=0.18$.

(b)

H-Cha$^c$Gly(SCH$_3$)-n-butylamide:

A mixture of 240 mg of

Z-Cha$^\alpha$Gly(SCH$_3$)-n-butylamide, 200 mg of 4-methylmercapto-phenol and 4 ml of trifluoroacetic acid is stirred for 30 hours at room temperature. The reaction mixture is concentrated, the residue is adjusted at 0°–5° to pH 9 with 0.2N aqueous NaOH and subsequently extracted repeatedly with methylene chloride. The combined extracts are dried and concentrated by evaporation. The residue is purified by flash chromatography on 25 g of silica gel 60 (eluant O). $R_f(P)=0.08$ (2 diastereoisomers).

(c)

Z-Cha$^\alpha$Gly(SCH$_3$)-n-butylamide is obtained from 950 mg of

Z-Cha$^\alpha$Gly(SCH$_3$)-OH:

460 mg of HOBt, 440 mg of n-butylamine and 700 mg of DCCI analogously to Example 2 (d) and is purified by flash chromatography with solvent system C, $R_f(A)=0.56$ and 0.50 (2 diastereoisomers).

(d)

Z-Cha$^\alpha$Gly(SCH$_3$)-methyl ester,

A mixture of 790 mg of

2(R,S)-(3-benzyloxycarbonyl-4(S)-cyclohexylmethyl-2,2-dimethyl-1,3-oxazolidinyl-5(S)-methyl)-2-methylthio-acteic acid methyl ester, Z-Cha$^\alpha$Gly(SCH$_3$)-methyl ester:

5 ml of 2N aqueous NaOH and 10 ml of 1,4-dioxan is stirred for 3 hours at room temperature. The reaction mixture is neutralised with 5 ml of 2N aqueous HCl and subsequently lyophilised. The title compound is obtained from the residue by flash chromatography (eluant system A). $R_f(A)=0.15$ and 0.10 (2 diastereoisomers).

(e)

Z-Cha$^\alpha$Gly(SCH$_3$)-OH,

Under nitrogen, 0.85 ml of diisopropylamine is dissolved in 15 ml of abs. THF and 10 ml of hexamethylphosphoric acid triamide and cooled to $-78°$. Subsequently, 4 ml of a 1.5M solution of n-butyllithium in hexane are added to the mixture and the whole is stirred for 30 minutes. Then, at $-70°$, 0.65 ml of methylthioacetic acid methyl ester is added dropwise and the whole is stirred for ½ hour at $-75°$. A solution of 1.3 g of the compound of Example 1 (e) in 5 ml of tetrahydrofuran and 5 ml of hexamethylphosphoric acid triamide is added to the reaction mixture and the whole is heated to 0° within a period of 2 hours. After the addition of 20 ml of saturated aqueous ammonium chloride solution, the product is extracted with ether. The combined organic phases are washed with brine, dried with sodium sulphate and concentrated by evaporation. The crude product is purified by flash chromatography (60 g of silica gel 60, 40–63 μm, eluant G). Concentration by evaporation of the combined product-containing fractions yields the two diastereoisomers of the title compound in the form of slightly yellowish oils. $R_f(C)=0.35$ and 0.32.

EXAMPLE 27

N-2(R,S)-benzyl3-tert.-butylsulphonyl-propionyl)-His-Cha$^c$Gly(SO$_2$CH$_3$)-n-butylamide 35 mg of N-2(R,S)-benzyl3-tert.-butylsulphonyl-propionyl)-His-Cha$^c$Gly(SCH$_3$)-n-butylamide are dissolved in 2 ml of methanol and 2 ml of 0.1N H$_2$SO$_4$, 55 mg of oxone ® (potassium peroxomonosulphate, 50% KHSO$_5$, Ventron) are added thereto and the whole is stirred overnight at room temperature. The mixture is diluted with saturated sodium bicarbonate solution and extracted with methylene chloride and the extracts are dried with sodium sulphate and concentrated to yield a diastereoisomeric mixture of the title compound. $R_f(I)=0.18$.

EXAMPLE 28

N-2(R,S)-benzyl3-tert.-butylsulphonyl-propionyl)-His-Cha$^c$Gly(OCH$_3$)-n-methylamide Analogously to Example 1, the title compound is manufactured from 102 mg of H-His-Cha$^c$Gly(OCH$_3$)-methylamide, 78 mg of 2-benzyl-3-tert.-butylsulphonylpropionic acid, 42 mg of HOBt and 67 mg of DCCI and is purified by flash chromatography on 30 g of silica gel 60 (eluant O). R$_f$(O)=0.24 and 0.20 (2 diastereoisomeric pairs).

The starting material is manufactured in the following manner:
(a)

H-His-Cha$^c$Gly(OCH$_3$)-methylamide is obtained by hydrogenating 130 mg of

Z-His-Cha$^c$Gly(OCH$_3$)-methylamide in the presence of 50 mg of palladium-on-carbon (10%) analogously to Example 1(k). R$_f$(R)=0.32 (diastereoisomeric mixture).
(b)

H-His-Cha$^c$Gly(OCH$_3$)-methylamide is obtained from 125 mg of Z-His-OH, 107 mg of H-Cha$^c$Gly(OCH$_3$)-methylamide, 66 mg of HOBt and 106 mg of DCCI analogously to Example 1(j) and is purified by flash chromatography with solvent system O. R$_f$(Q)=0.26.
(c)

H-Cha$^c$Gly(OCH$_3$)-methylamide is obtained by hydrogenating 184 mg of

H-Cha$^{\alpha}$Gly(OCH$_3$)-methylamide in the presence of 50 mg of palladium-on-carbon (10%) analogously to Example 1(i). R$_f$(R)=0.35.
(d)

Z-Cha$^{\alpha}$Gly(OCH$_3$)-methylamide:

258 mg of

Z-Cha$^{\alpha}$Gly(OCH$_3$)-ethyl ester are dissolved in 2 ml of methanol and 2 ml of 33% ethanolic methylamine solution are added thereto. The mixture is heated at 120°–130° C. for 20 hours in a bomb tube and is then concentrated. The residue is purified by flash chromatography on 50 g of silica gel 60 (eluant A). Yellow oil, R$_f$(A)=0.16.
(e)

Z-Cha$^{\alpha}$Gly(OCH$_3$)-ethyl ester is obtained analogously to Example 26 (e) from 601 mg of methoxyacetic acid ethyl ester, 0.72 ml of diisopropylamine, 3.2 ml of a 1.6M solution of n-butyllithium in hexane and 2 g of the compound of Example 1(e) and is purified by flash chromatography with solvent system G. R$_f$(C)=0.36 and 0.32 (diastereoisomeric mixture).

EXAMPLE 29

N-(2(R,S)-benzyl-3-[2-pyridylthio]-propionyl)-His-Cha$^c$Val-n-butylamide

Analogously to Example 1, the title compound is obtained from 85 mg of 2-benzyl-3-(2-pyridylthio)propionic acid, 115 mg of H-His-Cha$^c$Val-n-butylamide, 50 mg of HOBt and 102 mg of DCCI and is purified by flash chromatography with eluant V. R$_f$(X)=0.30 and 0.20 (2 diastereoisomers).

The starting material is manufactured in the following manner:
(a) 2-benzyl-3-(2-pyridylthio)-propionic acid:
903 mg of 2-benzyl-3-(2-pyridylthio)-propionic acid ethyl ester (Example 13(c)) are boiled under reflux for 10 hours in 10 ml of 4N HCl. The reaction mixture is extracted with methylene chloride/methanol 10:1. The extracts are adjusted to pH 6 with NaHCO$_3$ solution and subsequently washed with brine, dried with Na$_2$SO$_4$ and concentrated by evaporation. The residue is lyophilised from dioxan/water. R$_f$(I)=0.2.

EXAMPLE 30

N-(2(R)- and 2(S)-benzyl-3-[1-methyl-2-imidazolylthio]-propionyl)-His-Cha$^c$Val-n-butylamide Analogously to Example 1, the title compound is obtained from 277 mg of 2-benzyl-3-[1-methyl-2-imidazolylthio]-propionic acid, 560 mg of H-His-Cha$^c$Val-n-butylamide, 175 mg of HOBt and 310 mg of DCCI and is separated into the two diastereoisomers by flash chromatography with eluant O. Diastereoisomer I: R$_f$(I)=0.26. Diastereoisomer II: R$_f$(I)=0.19.

The starting material 2-benzyl-3-[1-methyl-2-imidazolylthio]-propionic acid is manufactured analogously to Examples 29 (a) and 1 (m) from α-benzylacrylic acid ethyl ester and 2-mercapto-1-methylimidazole.

EXAMPLE 31

N-(2(R,S)-benzyl-3-phenylsulphonyl-propionyl)-His-Cha$^c$Val-n-butylamide

Analogously to Example 1, the title compound is obtained from 150 mg of

H-His-Cha$^c$Val-n-butylamide, 151 mg of 2-benzyl-3-phenylsulphonyl-propionic acid, mg of HOBt and 103 mg of DCCI and is purified by flash chromatography (eluant H). R$_f$(I)=0.33 and 0.28 (2 diastereoisomers).

The starting material 2-benzyl-3-phenylsulphonyl-propionic acid is manufactured analogously to Example

EXAMPLE 32

N-(2(R,S)-benzyl-3-pyrrolidinosulphonyl-
propionyl)-His-Cha$^c$Val-n-butylamide

Analogously to Example 1, the title compound is obtained from 175 mg of 2-benzyl-3-pyrrolidinosulphonylpropionic acid, 139 mg of H-His-Cha$^c$Val-n-butylamide, 70 mg of HOBt and 120 mg of DCCI and is purified by flash chromatography with eluant N. $R_f(I)=0.24$ and 0.19 (2 diastereoisomers).

The starting material 2-benzyl-3-pyrrolidinosulphonyl-propionic acid is manufactured analogously to Example 14 (a) and (b).

EXAMPLE 33

N-(2(R,S)-benzyl-3-ethylthio-propionyl)-
His-Cha$^c$Val-n-butylamide

Analogously to Example 1, the title compound is obtained from 134 mg of 2-benzyl-3-ethylthio-propionic acid, 185 mg of H-His-Cha$^c$Val-n-butylamide, 70 mg of HOBt and 132 mg of DCCI and is purified by flash chromatography with eluant H. $R_f(I)=0.20$ and 0.15 (2 diastereoisomers).

The starting material 2-benzyl-3-ethylthiopropionic acid is manufactured analogously to Examples 4 (a) and 1 (m) from α-benzylacrylic acid ethyl ester and ethylmercaptan.

EXAMPLE 34

N-(2(R)- and 2(S)-benzyl-3-ethylsulphonyl-
propionyl)-His-Cha$^c$Val-n-butylamide A mixture of 81

N-(2(R,S)-benzyl-3-ethylthio-propionyl)-
His-Cha$^c$Val-n-butylamide (Example 33), 61 mg of 3-chloroperbenzoic acid and 5 ml of chloroform is stirred for 20 hours at 25° C. The reaction mixture is rendered basic with concentrated NaHCO$_3$ solution and subsequently extracted with 50 ml of chloroform. The organic phase is washed with 10 ml of brine, dried with Na$_2$SO$_4$, filtered and concentrated by evaporation. The residue is separated by means of flash chromatography (20 g of silica gel 60, eluant N). The product-containing fractions of the two diastereoisomers are combined, concentrated and subsequently lyophilised from dioxan/water 9:1. Diastereoisomer I: $R_f(Q)=0.38$. Diastereoisomer II: $R_f(Q)=0.43$.

EXAMPLE 35

N-(2(S)-benzyl-3-tert.-butylsulphonyl-
propionyl)-Ser-Cha$^c$Val-methylamide

Analogously to Example 1, the title compound is manufactured from 80 mg of 2(S)-benzyl-3-tert.-butylsulphonyl-propionic acid, 80 mg of H-Ser-Cha$^c$Val-methylamide, 40 mg of HOBt and 67 mg of DCCI and is purified by flash chromatography on 65 g of silica gel 60 (eluant O). $R_f(O)=0.28$.

The starting material is manufactured in the following manner:

(a)

H-Ser-Cha$^c$Val-methylamide is obtained by hydrogenating 230 mg of

Z-Ser-Cha$^c$Val-methylamide in the presence of 50 mg of palladium-on-carbon (10%) analogously to Example 1(k). $R_f(P)=0.21$.

(b)

Z-Ser-Cha$^c$Val-methylamide is obtained from 213 mg of Z-Ser-OH, 169 mg of

H-Cha$^c$Val-methylamide, 109 mg of HOBt and 184 mg of DCCI analogously to Example 1(j) and is purified by flash chromatography on 80 g of silica gel 60 (eluant O). $R_f(O)=0.37$.

EXAMPLE 36

N-(2(S)-benzyl-3-tert.-butylsulphonyl-
propionyl)-His-Cha$^c$Val-methylamide

Analogously to Example 1, the title compound is manufactured from 50 mg of

H-His-Cha$^c$Val-methylamide, 37 mg of 2(S)-benzyl-3-tert.-butylsulphonylpropionic acid (Example 9(a)), 20 mg of HOBt and 32 mg of DCCI and purified by medium-pressure chromatography (1 Lobar ® column size B, eluant N). $R_f(Q)=0.30$.

EXAMPLE 37

N-(2(S)-benzyl-3-tert.-butylsulphonyl-
propionyl)-His-Cha$^c$Ala-methylamide

Analogously to Example 1, the title compound is manufactured from 63 mg of

H-His-Cha$^c$Ala-methylamide, 60 mg of 2(S)-benzyl-3-tert.-butylsulphonylpropionic acid (Example 9(a)), 32 mg of HOBt and 46 mg of DCCI and is purified by flash chromatography on 50 g of silica gel 60 (eluant P). $R_f(P)=0.24$.

The starting material is manufactured in the following manner:

(a)

H-His-Cha<sup>c</sup>Ala-methylamide is obtained by hydrogenating 80 mg of

Z-His-Cha<sup>c</sup>Ala-methylamide in the presence of 30 mg of palladium-on-carbon (10%) analogously to Example 1(k). $R_f(P)=0.11$; $R_f(AA)=0.22$.

(b)

Z-His-Cha<sup>c</sup>Ala-methylamide is obtained from 72 mg of Z-His-OH, 53 mg of H-Cha<sup>c</sup>Ala-methylamide, 35 mg of HOBt and 60 mg of DCCI analogously to Example 1(j) and is purified by flash chromatography (eluant P). $R_f(P)=0.16$.

(c)

H-Cha<sup>c</sup>Ala-methylamide:

220 mg of

BOC-Cha<sup>α</sup>Ala-methylamide are dissolved in 5 ml of trifluoroacetic a water 95:5. After 30 minutes, the mixture is concentrated in a rotary evaporator and the residue is purified by flash chromatography (eluant AA). Concentration by evaporation of the product-containing fractions yields the title compound $R_f(AA)=0.33$.

(d)

BOC-Cha<sup>α</sup>Ala-methylamide:

185 mg of

BOC-Cha<sup>α</sup>Ala-OH:

are pre-activated for 2 hours at room temperature in a stirred solution in DMF with 111 mg of HOBt and 149 mg of DCCI and subsequently 1 ml of a 5N solution of methylamine in DMF is added thereto. After 2 hours at room temperature, the solvent is removed and the title compound is purified by flash chromatography in system A. $R_f(A)=0.25$.

(e)

BOC-Cha<sup>α</sup>Ala-OH 340 mg of 3-tert.-butoxycarbonyl-4(S)-cyclohexylmethyl-2,2-dimethyl-5(S)-(3-hydroxy-2(R)-methyl-propyl)-1,3-oxazolidine are dissolved in DMF and stirred with 1040 mg of pyridinium chromate in DMF for 16 hours. The mixture is concentrated in a rotary evaporator and the residue is purified by flash chromatography (eluant B). $R_f(B)=0.12$.

(f) 3-tert.-butoxycarbonyl-4(S)-cyclohexylmethyl-2,2-dimethyl-5(S)-(3-hydroxy-2(R)-methyl-propyl)-1,3-oxazolidine is obtained by hydrogenating 1.90 g of 5(S)-(3-benzyloxy-2(R)-methyl-propyl)-3-tert.-butoxycarbonyl-4(S)-cyclohexylmethyl-2,2-dimethyl-1,3-oxazolidine in methanol in the presence of 200 mg of Pd-on-carbon (10%). $R_f(C)=0.15$.

(g) 5(S)-(3-benzyloxy-2(R)-methyl-propyl)-3-tert.-butoxycarbonyl-4(S)-cyclohexylmethyl-2,2-dimethyl-1,3-oxazolidine is manufactured analogously to Example 1(e) from benzyl 5(S)-tert.-butoxycarbonylamino-6-cyclohexyl-4(S)-hydroxy-2(R)-methyl-1-hexyl ether and 2,2-dimethoxypropane in the presence of p-toluenesulphonic acid monohydrate in methylene chloride. $R_f(C)=0.45$.

(h) benzyl 5(S)-tert.-butoxycarbonylamino-6-cyclohexyl-4(S)-hydroxy-2(R)-methyl-1-hexyl ether:

A Grignard solution prepared from 3.6 g of (S)-(+)-3-benzyloxy-2-methyl-propyl bromide (A. Fischli et al., Helv. Chim. Acta 60, 925 (1977)) and 360 mg of magnesium in diethyl ether is added dropwise within 15 minutes at 0° to 1.50 g of 2(S)-tert.-butoxycarbonylamino-3-cyclohexyl-propionaldehyde (J. Boger et al., J. Med. Chem. 28, 1779 (1985)) in 15 ml of diethyl ether. After 30 minutes at 0°, the reaction solution is poured onto 50 ml of 1N HCl and the crude product (diastereoisomer ratio (4S):(4R)=4:1) is extracted with dichloromethane. The desired diastereoisomer having the 4(S)-configuration is isolated in pure form by flash chromatography on 250 g of silica gel 60 (eluant dichloromethane/ether 20:1). $R_f(L)=0.10$.

EXAMPLE 38

N-(2(S)-benzyl-3-tert.-butylsulphonyl-His-Cha<sup>c</sup>Val-n-butylamide

A mixture of 51 mg of

N-(2(S)-benzyl-3-[1-methyl-2-imidazolylthio]-propionyl)-His-Cha<sup>c</sup>Val-n-butylamide (Example 30), 64 mg of oxone ® (potassium peroxomonosulphate, 50% KHSO$_5$, Ventron), 2 ml of 0.1N H$_2$SO$_4$ and 2 ml of methanol is stirred at 25° for 20 hours. The reaction mixture is extracted with chloroform, and the extracts are washed with brine, dried and concentrated. The residue is lyophilised from dioxan/water 3:1. $R_f(EE)=0.2$.

EXAMPLE 39

5(S)-[N-(2(S)-benzyl-3-tert.-butylsulphonyl-propionyl)-histidinyl]-amino-6-cyclohexyl-4(R)- and 4(S)-hydroxy-2(S)-isopropylhexanoic acid n-butylamide A solution of 37 mg of 5(S)-[N-(2(S)-benzyl-3-tert.-butylsulphonyl-propionyl)-histidinyl]-amino-6-cyclohexyl-2(S)-isopropyl-4-oxo-hexanoic acid n-butylamide and 8 mg of sodium borohydride in 3 ml of methanol is stirred at 25° C. for 6 hours. Subsequently, the whole is acidified with 2N HCl and partitioned between 50 ml of CH$_2$Cl$_2$ and 10 ml of saturated NaHCO$_3$ solution. The organic extracts are dried and concentrated by evaporation. The residue is purified by flash chromatography on 10 g of silica gel 60 (eluant M). $R_f(O)=0.35$ (diastereoisomeric mixture). The diastereoisomeric mixture contains in addition to 3 parts of the 4(R)-compound 1 part of the 4(S)-compound which is identical with the compound of Example 9.

The starting material is manufactured in the following manner:

(a) 5(S)-[N-(2(S)-benzyl-3-tert.-butylsulphonylpropionyl)-histidinyl]-amino-6-cyclohexyl-2(S)-isopropyl-4-oxo-hexanoic acid n-butylamide:

A mixture of 253 mg of

N-(2(S)-benzyl-3-tert.-butylsulphonyl-
propionyl)-His-Cha$^c$Val-n-butylamide (Example 9), 130 mg of pyridinium chlorochromate and 5 ml of methylene chloride is stirred at room temperature for 10 hours. The reaction mixture is diluted with 100 ml of ethyl acetate and then washed with 20 ml of water. The organic phase is dried and concentrated by evaporation and the residue is purified by means of flash chromatography on 40 g of silica gel 60 (eluant H). $R_f(O)=0.43$.

EXAMPLE 40

N-(2(S)-benzyl-3-tert.-butylsulphonyl-
propionyl)-His-Cha$^c$Val-n-butylamide
by an alternate condensation reaction A mixture of 127 mg of N-(2(S)-benzyl-tert.-butylsulphonyl-propionyl)-His-OH, 65 mg of H-Cha$^c$Val-n-butylamide, 55 mg of N-hydroxy-norbornane-endo-2,3-dicarboxylic acid imide, 62 mg of DCCI and 2 ml of DMF is stirred at room temperature for 70 hours. The crystallised DCU is filtered off and the filtrate is concentrated by evaporation. The residue is stirred in a mixture of methanol/water/glacial acetic acid 94:3:3 for 30 minutes at 60° C. and is subsequently concentrated. The residue is purified by means of flash chromatography on 40 g of silica gel 60 (eluant M). The fractions containing the title compound are combined and lyophilised from dioxan/water 9:1. The product is identical with the compound of Example 9, $R_f(O)=0.35$.

The starting material is manufactured in the following manner:

(a) N-(2(R)- and 2(S)-benzyl-3-tert.-butylsulphonyl)-propionyl)-His-OH:

284 mg of 2-benzyl-3-tert.-butylsulphonyl-propionic acid (Example 1 (o)), 121 mg of N-hydroxysuccinimide and 227 mg of DCCI are dissolved in 4 ml of DMF and the solution is stirred at 25° C. for 1 hour. The crystallised DCU is filtered off and the filtrate is stirred with a solution of 245 mg of histidine sodium salt in 6 ml of DMF/water 2:1 for 3 hours at room temperature. The reaction mixture is diluted with 1 ml of 1N HCl and concentrated. The residue is separated by flash chromatography (30 g of silica gel 60, eluant J). The product-containing fractions of the separated diastereoisomers are combined and lyophilised from dioxan/water 5:1. 2(R)-compound: $R_f(EE)=0.27$. 2(S)-compound: $R_f(EE)=0.32$.

Alternative method of preparation:

(b) N-2(S)-benzyl-3-tert.-butylsulphonyl-propionyl)-His-OH is obtained analogously to Example (a) from 4.15 g of 2(S)-benzyl-3-tert.-butylsulphonyl-propionic acid, 1.77 g of N-hydroxysuccinimide, 3.62 g of DCCI and 3.55 g of histidine sodium salt. $R_f(EE)=0.32$.

EXAMPLE 41

N-(2(R,S)-benzyl-3-tert.-butylsulphonyl-
propionyl)-His-Cha$^c$Val-n-butylamide
by oxidation of the sulphinyl compound A mixture of 142 mg of N-(2(R,S)-benzyl-3-tert.-butylsulphinyl-
propionyl)-His-Cha$^c$Val-n-butylamide (Example 3), 64 mg of sodium (meta)periodate and 10 ml of methanol/water 1:1 is stirred at room temperature for 20 hours. The reaction mixture is diluted with 10 ml of NaHCO$_3$ solution and then extracted with 100 ml of methylene chloride. The methylene chloride extracts are washed with brine, dried with Na$_2$SO$_4$ and concentrated. The residue is purified by means of flash chromatography (50 g of silica gel 60, eluant M). The product is identical with the diastereoisomeric mixture of Example 2, $R_f(O)=0.30$ and 0.35 (2 diastereoisomers).

EXAMPLE 42

N-(2(R,S)-benzyl-3-tert.-butylsulphonyl-
propionyl)-His-Cha$^c$Val-n-butylamide
by sulphinate addition A mixture of 100 mg of N-(α-benzylacryloyl)-His-Cha$^c$Val-methylamide and 80 mg of sodium tert.-butylsulphinate is stirred in THF for 20 hours at 50° C. The reaction mixture is then partially concentrated and the title compound is purified by flash chromatography on 80 g of silica gel 60 (eluant O). The product is identical with the diastereoisomeric mixture of Example 1, $R_f(Q)=0.26$ and 0.30 (2 diastereoisomers).

The starting material is manufactured in the following manner:

(a)

N-(α-benzylacryloyl)-His-Cha$^c$Val-methylamide:

Analogously to Example 1, the title compound is obtained from 32 mg of α-benzylacrylic acid, 50 mg of H-His-Cha$^c$Val-methylamide, 20 mg of HOBt and 32 mg of DCCI and is purified by flash chromatography in system Q. $R_f(Q)=0.36$.

EXAMPLE 43

N-(2(R,S)-benzyl-3-tert.-butylsulphonyl-
propionyl)-His-Cha$^c$Val-n-butylamide
by removal of a silyl protecting group 840 mg of 5(S)-[N-(2(R,S)-benzyl-3-tert.-butylsulphonyl-propionyl)-histidinyl]-amino-4(S)-tert.-butyldimethylsilyloxy-6-cyclohexyl-2(S)-isopropyl-hexanoic acid n-butylamide are dissolved in 24 ml of acetonitrile and, at 25°, 1.25 ml of 48% hydrofluoric acid are added thereto. After 30 minutes, 2.0 g of sodium bicarbonate are added and the solvent is evaporated off. The residue is taken up in ethyl acetate, washed with water, dried with sodium sulphate, again concentrated by evaporation, and purified by flash chromatography on 100 g of silica gel (eluant M). The product is identical with the diastereoisomeric mixture of Example 2, $R_f(O)=0.30$ and 0.35 (2 diastereoisomers).

The starting material is manufactured in the following manner:

(a) 5(S)-[N-(2(R,S)-benzyl-3-tert.-butylsulphonylpropionyl)-histidinyl]-amino-4(S)-tert.-butyldimethyl-silyloxy-6-cyclohexyl-2(S)-isopropyl-hexanoic acid n-butylamide is manufactured analogously to Example 1 from 2-benzyl-3-tert.-butylsulphonyl-tropionic acid and the tert.-butyldimethylsilyl ether of H-His-Cha$^c$Val-n-butylamide which is obtained analogously to Example 2 (a), (b) and (c) from the corresponding ether of Z-Cha$^c$Val-n-butylamide (Example 43(b).

(b) 5(S)-benzyloxycarbonylamino-4(S)-tert.-butyldimethylsilyloxy-6-cyclohexyl-2(S)-isopropyl-hexanoic acid n-butylamide is formed from 4.6 g of Z-Cha$^c$Val-n-butylamide in the presence of 1.36 g of imidazole and 2.3 g of tert.-butyldimethylchlorosilane in 75 ml of DMF.

EXAMPLE 44

N-(2(R,S)-benzyl-3-tert.-butylsulphonyl-propionyl)-His-Cha$^c$Val-n-butylamide by removal of the 2-chloroethoxy-carbonyl protecting group 830 mg of 5(S)-[N-(2(R,S)-benzyl-3-tert.-butylsulphonyl-propionyl)-histidinyl]-amino-4(S)-(2-chloroethoxycarbonyloxy)-6-cyclohexyl-2(S)-isopropyl-hexanoic acid n-butylamide in 20 ml of DMF are added dropwise to a solution of 0.8 g of carbon disulphide and 2.5 g of sodium sulphide nonahydrate in DMF. The mixture is heated at 40° for 10 minutes, then concentrated by evaporation. The residue is taken up in ethyl acetate, washed with 20 ml of water, dried with sodium sulphate, again concentrated by evaporation, and purified by flash chromatography on 100 g of silica gel (eluant M). The product is identical with the diastereoisomeric mixture of Example 2, $R_f(O)=0.30$ and 0.35 (2 diastereoisomers).

The starting material is manufactured analogously to Example 43 (a) and (b) from Z-Cha$^c$Val-n-butylamide and 2-chloroethoxychloroformate and condensation with histidine and 2-benzyl-3-tert.-butylsulphonyl-propionic acid.

EXAMPLE 45

Alternate reaction conditions for the manufacture of N-(2(R,S)-benzyl-3-tert.-butylsulphonyl-propionyl)-His-Cha$^c$Val-n-butylamide by condensation (a) Using bis-(2-oxo-3-oxazolidinyl)-phosphinic acid chloride:

50 mg of 2-benzyl-3-tert.-butylsulphonylpropionic acid, 81 mg of

H-His-Cha$^c$Val-n-butylamide and 47 mg of bis-(2-oxo-α-oxazolidinyl)-phosphinic acid chloride are stirred for 20 hours at room temperature in 4 ml of acetonitrile. The reaction mixture is then concentrated and the residue is purified by flash chromatography on 70 g of silica gel 60 (system Q). $R_f(O)=0.30$ and 0.35 (2 diastereoisomers).

(b) Using 1-benzotriazolyloxy-tris-(dimethylamino)-phosphonium hexafluoroborate (Castro's reagent, BOP):

50 mg of 2-benzyl-3-tert -butylsulphonylpropionic acid, 81 mg of

H-His-Cha$^c$Val-n-butylamide and 78 mg of the title reagent BOP are stirred for 201 hours at room temperature in 5 ml of methylene chloride and worked up as described in (a).

(c) Using 2-ethoxy-1-ethoxycarbonyl-1,2-dihydroquinoline (EEDQ):

50 mg of α-benzyl-3-tert.-butylsulphonylpropionic acid, 81 mg of

H-His-Cha$^c$Val-n-butylamide and 44 mg of the title reagent EEDQ are stirred for 20 hours at room temperature in 4 ml of THF and worked up as described in (a).

EXAMPLE 46

The following are manufactured analogously to the Examples given above:

(a) N-(2(R,S)-benzyl-3-sulphamoyl-propionyl)-His-Cha$^c$Val-n-butylamide.

(b) N-(2(R,S)-benzyl-3-methylaminosulphonyl-propionyl)-His-Cha$^c$Val-n-butylamide.

(c) N-(2(R,S)-benzyl-3-tert.-butylsulphonyl-propionyl)-His-Cha$^c$Gly(OH)-methylamide.

(d) N-(2(R,S)-benzyl-3-tert.-butylsulphonyl-propionyl)-His-Cha$^c$Val-(2-sulphoethyl)-amide.

(d) N-(2(R,S)-benzyl-3-tert.-butylsulphonyl-propionyl)-His-Cha$^c$Val-(4-aminobutyl)-amide.

EXAMPLE 47

Gelatine solution

A sterile-filtered aqueous solution of

N-(2(R,S)-benzyl-3-tert.-butylsulphonyl-propionyl)-His-Cha$^c$Val-n-butylamide is mixed under aseptic conditions, while heating, with a sterile gelatine solution containing phenol as preservative, in such a manner that 1.0 ml of solution has the following composition:

| | |
|---|---|
| N-(2(S)-benzyl-3-tert.-butylsulphonyl-propionyl)-His-Cha$^c$Val-n-butylamide | 3 mg |
| gelatine | 150.0 mg |
| phenol | 4.7 mg |
| distilled water up to | 1.0 ml |

The mixture is introduced under aseptic conditions into 1.0 ml phials.

EXAMPLE 48

Sterile dry substance for injection 5 mg of

N-(2(R,S)-benzyl-3-tert.-butylsulphonyl-propionyl)-His-Cha$^c$Val-n-butylamide are dissolved in 1 ml of an aqueous solution containing 20 mg of mannitol. The solution is sterile-filtered and, under aseptic conditions, introduced into a 2 ml ampoule, deep-frozen and lyophilised. Before use, the lyophilisate is dissolved in 1 ml of distilled water or 1 ml of physiological saline solution. The solution is administered intramuscularly or intravenously. This formulation can also be placed in double-chamber syringe ampoules.

EXAMPLE 49

Nasal spray 500 mg of finely ground (<5.0 μm)

N-(2(R,S)-benzyl-3-tert.-butylsulphonyl-propionyl)-His-Cha$^c$Val-n-butylamide are suspended in a mixture of 3.5 ml of Myglyol 812 ® and 0.08 g of benzyl alcohol. This suspension is introduced into a container having a metering valve. 5.0 g of Freon ® 12 are introduced under pressure into the container through the valve. The Freon ® is dissolved in the Myglyol/benzyl alcohol mixture by shaking. This spray container contains approximately 100 single doses which may be administered individually.

EXAMPLE 50

Lacquer-coated tablets

For the manufacture of 10,000 tablets each containing 100 mg of active ingredient the following constituents are processed:

| | |
|---|---|
| N-(2(S)-butyl-3-tert.-butylsulphonyl-propionyl)-His-Cha$^c$Val-n-butylamide | 1000 g |
| corn starch | 680 g |
| colloidal silica | 200 g |
| magnesium stearate | 20 g |
| stearic acid | 50 g |
| sodium carboxymethyl starch | 250 g |
| water | q.s. |

A mixture of the

N-(2(R,S)-benzyl-3-tert.-butylsulphonyl-propionyl)-His-Cha$^c$Val-n-butylamide, 50 g of corn starch and the colloidal silica is worked with starch paste consisting of 250 g of corn starch and 2.2 kg of demineralised water to form a moist mass. The latter is forced through a sieve of 3 mm mesh width and dried for 30 minutes at 45° in a fluidised bed drier. The dry granulate is pressed through a sieve of 1 mm mesh width, mixed with a previously sieved mixture (1 mm sieve) of 330 g of corn starch, the magnesium stearate, the stearic acid and the sodium carboxymethyl starch and pressed to form slightly convex tablets.

The compacts are coated in a coating vessel of 45 cm diameter by uniform spraying for 30 minutes with a solution of 20 g of shellac and 40 g of hydroxypropylmethylcellulose (low viscosity) in 110 g of methanol and 1350 g of methylene chloride; during this process, drying is carried out by simultaneously blowing in air at 60°.

Instead of the above-mentioned active ingredient, it is also possible to use the same amount of another active ingredient of the preceding Examples.

We claim:

1. A compound of the formula

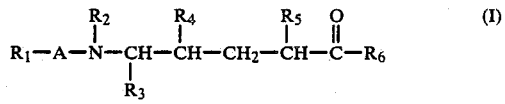

wherein A is alanyl or seryl; $R_1$ is of the formula

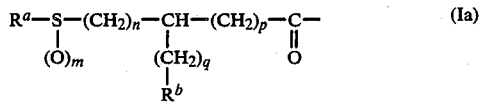

in which $R_a$ is lower alkyl which is unsubstituted or substituted by hydroxy, lower alkoxy, lower alkanoyloxy, halogen, amino, lower alkylamino, dilower alkylamino, or by lower alkoxycarbonylamino; m is 0, 1 or 2; n is 0 or 1; p is 0; q is 1 or 2; and $R^b$ is phenyl which is unsubsituted or substituted by at last one substituent selected from lower alkyl, hydroxy, lower alkoxy, lower alkanoyloxy amino, lower alkylamino, dilower alkylamino, t-butoxycarbonylamino, and halogen; $R_2$ is hydrogen or lower alkyl; $R_3$ is cyclo lower alkyl-lower alkyl; $R_4$ is (a) hydroxy, (b) hydrxy etherified by an organic radical that can be removed under physiological conditions and the cleavage products of which are physiologically tolerable in the resulting concentration, or (c) hydroxy etherified by lower alkanoyl, cyclo lower alkylcarbonyl, or benzoyl; $R_5$ is lower alkyl; and $R_6$ is alkylamino having 1–10 carbon atoms or dilower alkylamino; or a pharmaceutically acceptable salt thereof.

2. A compound of claim 1 wherein $R_4$ is hydroxy, straight chain or branched lower alkanoyloxy-lower alkoxy, straight chain or branched lower alkoxycarbonyloxy-lower alkoxy, lower alkoxy, phenoxy, phenyl-lower alkoxy, lower alkanoyloxy, cyclo lower alkylcarbonyloxy, or benzoyloxy; or a pharmaceutically acceptable salt thereof.

3. A compound of claim 1 wherein $R_4$ is hydroxy, acetoxymethoxy, 1-acetoxyethoxy, pivaloyloxymethoxy, 1-pivaloyloxyethoxy, ethoxycarbonyloxymethoxy, 1-ethoxycarbonyloxyethoxy, t-butoxycarbonyloxymethoxy, 1-t-butoxycarbonyloxyethoxy, methoxy, ethoxy, phenoxy, benzyloxy, acetoxy, pivaloyoxy, cyclohexylcarbonyloxy, or benzoyloxy; or a pharmaceutically acceptable salt thereof.

4. A compound of claim 1 wherein $R^a$ is lower alkyl; or a pharmaceutical acceptable salt thereof;

5. A compound of claim 1 wherein A is bound N-terminally to $R_1$ and C-terminally to the group —$NR_2$—; $R_4$ is hydroxy; and $R_5$ is lower alkyl of at least 2 carbon atoms; or a pharmaceutically acceptable salt thereof.

6. A compound of claim 1 wherein A is bound N-termially to R; and C-terminally to the group —$NR_2$—; $R_2$ is hydrogen; $R_4$ is hydroxy; $R_5$ is lower alkyl of at least 2 carbon atoms; and $R_6$ is lower alkylamino or dilower alkylamino; or a pharmaceutically acceptable salt thereof.

7. A compound of claim 1 wherein A is bound N-terminally to $R_1$; and C-terminally to the group —$NR_2$—; $R^a$ is lower alkyl; $R^b$ is phenyl; n is one; $R_2$ is hydrogen; $R_3$ is cyclohexylmethyl; $R_4$ is hydroxy; $R_5$ is isopropyl; and $R_6$ is lower alkylamino or dimethylamino; or a pharmaceutically acceptable salt thereof.

8. The compound of claim 1 wherein A is alanyl and is bound N-terminally to $R_1$ and C-terminally to the group —$NR_2$—; $R_a$ is t-butyl; $R_b$ is phenyl; m is 2; n is one; q is one; $R_2$ is hydrogen; $R_3$ is cyclohexylmethyl; $R_4$ is hydroxy; $R_5$ is isopropyl; and $R_6$ is n-butylamino; and the carbon atoms carrying the radicals $R_3$, $R_4$ and $R_5$ and the methine carbon atom in formula Ia have the S-configuration; or a pharmaceutically acceptable salt thereof.

9. A pharmaceutical preparation for treating renin-associated hyperaldosteronism and cardiac insufficiency containing an effective amount of a compound or a pharmaceutically acceptable salt thereof according to claim 1 together with a pharmaceutical carrier.

10. A method of treating a warm-blooded animal suffering from renin-associated hyperaldosteronism, hypertension or cardiac insufficiency by administering to said animal a therapeutically effective amount of a compound or a pharmaceutically acceptable salt thereof according to claim 1.

* * * * *